(12) United States Patent
Yayon et al.

(10) Patent No.: US 6,265,632 B1
(45) Date of Patent: Jul. 24, 2001

(54) ANIMAL MODEL FOR FIBROBLAST GROWTH FACTOR RECEPTOR ASSOCIATED CHONDRODYSPLASIA

(75) Inventors: Avner Yayon, Moshav Sitria; Orit Segev, Rehovot, both of (IL)

(73) Assignees: Yeda Research and Development Co. Ltd.; Prochon Biotech Ltd., both of Rehovot (IL)

( * ) Notice: Subject to any disclaimer, the term of this patent is extended or adjusted under 35 U.S.C. 154(b) by 0 days.

(21) Appl. No.: 09/383,630

(22) Filed: Aug. 26, 1999

(30) Foreign Application Priority Data

Aug. 27, 1998 (IL) ........................................................ 125958

(51) Int. Cl.⁷ ......................... A01K 67/027; A01K 67/00
(52) U.S. Cl. .................................... 800/18; 800/8; 800/9
(58) Field of Search ................................ 800/8, 2, 18, 9; 536/23.5, 24.1

(56) References Cited

U.S. PATENT DOCUMENTS 5,650,550 * 7/1997 Korach et al. ............................ 800/2

OTHER PUBLICATIONS

Wang et al. Proc. Natl. Acad Sci. USA 96:4455–4460, 1999.*
Monsonego–Ornan et al. Mol Cell Biol, 20: 516–22, 2000.*
Garofalo et al. J Bone and Mineral Res 14: 1909–15, 1999.*
Mullins JJ et al. Hypertension 22:630–633, 1993.*
Cameron ER. Molecular Biotechnology 7:253–265, 1997.*
Hammer RE et al. Cell 63:1099–1112. 1990.*
Seidel GE. J. Anim. Sci. 71(Suppl. 3):26–33, 1993.*
Mullins LJ and Mullins JJ. J. Clin. Invest.97:1557–1560, 1996.*
McEwen DG et al. The Journal of Biological Chemistry 273:5349–5357, 1998.*
Deng C et al. Cell 84:911–921, 1996.*
Naski MC et al. Nature Genetics 13:233–237, 1999.*
Webster M et al. The EMBO J 15:520–527, 1996.*
Wilke AOM et al. Current Biology 5:500–507, 1995.*

* cited by examiner

*Primary Examiner*—Karen M. Hauda
*Assistant Examiner*—Ram R. Shukla

(57) ABSTRACT

A genetically modified animal is disclosed. The animal has a genetically modified fibroblast growth factor receptor gene integrated in at least one locus in its genome. The genetically modified fibroblast growth factor receptor gene encodes a modified fibroblast growth factor receptor protein, that, when expressed, results in an integral membrane protein having a gain of function.

9 Claims, 10 Drawing Sheets

(5 of 10 Drawing Sheet(s) Filed in Color)

a. Southern b. Western

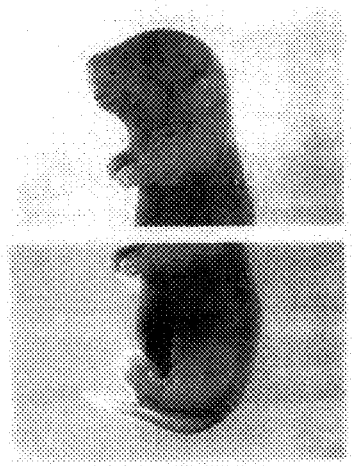
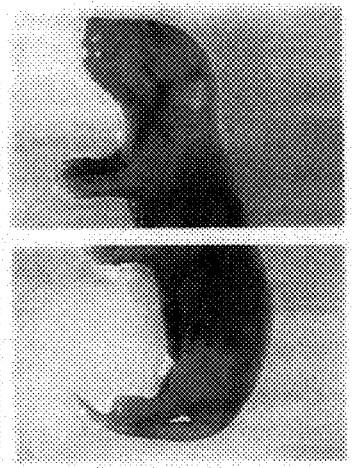
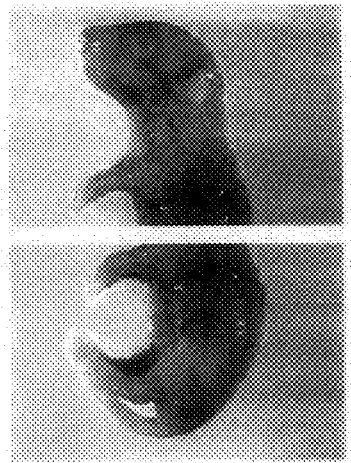
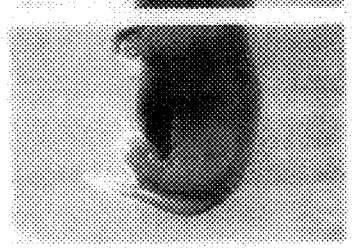
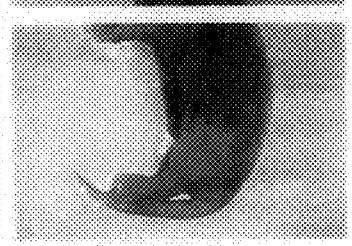
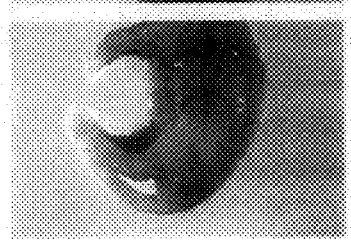
Fig. 5a  Fig. 5c  Fig. 5e
Fig. 5b  Fig. 5d  Fig. 5f

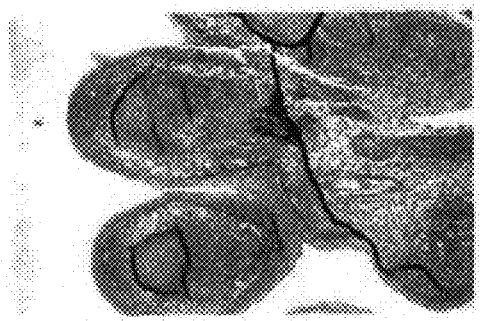 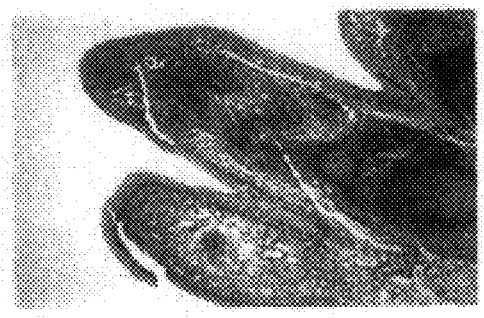
Fig. 9a　　　　Fig. 9b
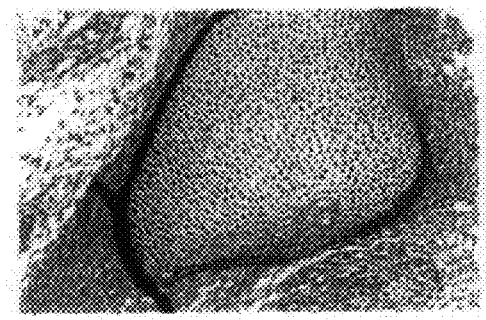 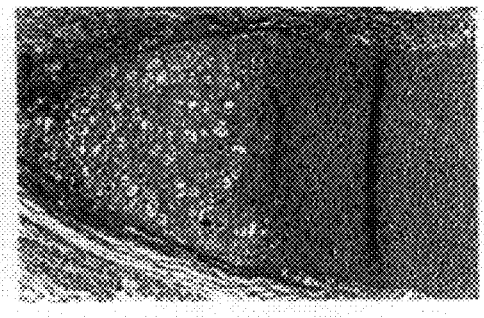
Fig. 9c　　　　Fig. 9d
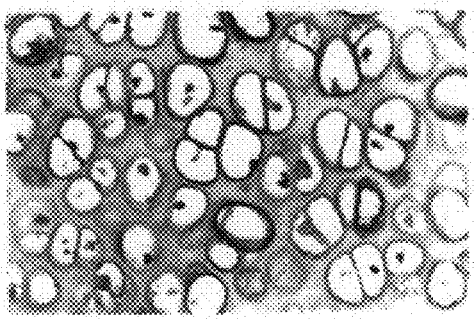 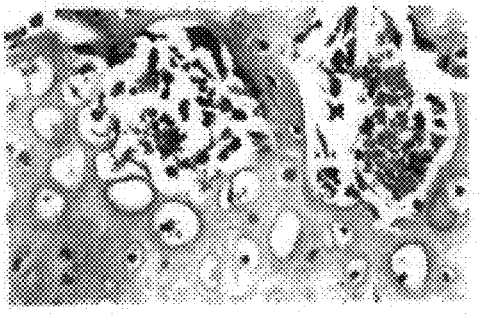
Fig. 9e　　　　Fig. 9f

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
        (A) LENGTH: 5993
        (B) TYPE: nucleic acid
        (C) STRANDEDNESS: double
        (D) TOPOLOGY: linear (xi) SEQUENCE DESCRIPTION: SEQ ID NO: 1:

| | | | |
|---|---|---|---|
| GGATCCACAA ATGTGACCTT ATTTGGAAAA AGAGTCTTGC AAGCATAACG | 50 |
| ATGGGAAGAG GCTTGAGGTG AGACCATCTT CACTTTATGA ACAACTCTAA | 100 |
| ATCCAACCAC AAGTGTCCTT ATGCAGGACA GGAGACGTGG GGAGGATAGA | 150 |
| AAAGGGCACA GAAGCCATGG GAAGGGAGAG GCAGAGACTA GACTGAGATG | 200 |
| ACCCGTAAGC CATTGGATGC CTGCAGGCCC CAGAGTTATA CAGGCAGGA | 250 |
| AGAAGCCTAT TCAGGGCCCC CAGCCCAACT TGACCTCAGA CTTCTGTTGT | 300 |
| CCTGAATTGA AAAGTAAAT TTAAGACAAC CAGATTTTAA TCTGGAAGTC | 350 |
| GGCTCAATAC AGGTAATACA AGTTGTAGCC GGGCGTGGTA GCCCACGCCT | 400 |
| TTAATCCCAG CACTCGGGAG GCAGAGGCAG GCGGATTTCT GAGTTCAAGG | 450 |
| TCTGCCTGGT TTACAAAGTG AGTTTCAGGA CAGCCAGGGC TACAGAGAAA | 500 |
| CCCTGTTTCG AAAACCAAA AAAAAAAAAA AAAAAAAAA AGGAATACAA | 550 |
| GTTGTGAATA GTTGTGAACA CCACACAGCT CATTTTTAAT GAAGGGCTG | 600 |
| ATTCCCCCCC CCCCACTGCT GCAGTTGAGC AGGGGTCTAC AAAAGCTGGC | 650 |
| CATTGTAAGG CCACAGGGTT GGGGGAGGAT CAGAGGAATG GGAGTACCCT | 700 |
| GGCTTAGAGT CCTCTTTCCT GCATGTGTTA GCCCATTGGA AAACAAGGTA | 750 |
| GCTTGAAAAG AGATGGTCTG TTGGGCCATG GGGTTCAAAA AACAACCAAC | 800 |
| ACCATGGCCT GAGATTCCTG ACTGGGTATT TCTAACAAGG AGGTCATCTC | 850 |
| AAAAATAAAT AATTATTGCT GTTTGGATGG ATGCTCAGCT CCCAGTTACA | 900 |
| GAGTGTGGAG GGTTCTGATA AATCCTCCAG ACGAAGGGCG TGGAAATAGG | 950 |
| GGTCAGAGCT CACATTCTGG TTCATTTACT GATAAACTAA TCTGCCAATA | 1000 |
| GATTAGGGGA GAATGTCTGC TATGACCCCC TGGGGTGGCA TCCTGGGAGA | 1050 |
| GGACCTGTGG GCAGCTGCCT GGGGGTGCCA TGGGAACCCA GGACTGGATT | 1100 |
| CTAGCCAGTC TGCAGGGAGG GGTCCTTGGC CAGAGCAGGA GTAACAGTAG | 1150 |
| GCAGAGCTGC CCAGCTCTAG GGTGGACACA CAGGGATGAG AGCATGAGGG | 1200 |
| TTCTGGGGCC AGGGCTTTCC CTGCTCAGCT ATCTGGGAAA GATAAGGGTG | 1250 |
| ATGAGTAAGC CAGTGAAAGG TGTTGGTAAC CCACGAGCCA TTCCCCCCCC | 1300 |
| CACCCCCCCC ATGAGCAGTT TAGTTCTTCA AGCCACATAC AGCCAGACTG | 1350 |
| GGCAGAAGCA CTGAGCCAGG TCCCCATGTA TCTGGCTCCC ATAGGCTTCA | 1400 |
| TCAGACCTTG TGGAACTTGT CTGAAAGTGA GACAAGGTTC CCTGCCTTGT | 1450 |
| GAGGGTAGAG AGGCCATCAG TCACAGGGTG GTTGCTGTTA CAGAAGTTCT | 1500 |
| GCCAGGCAGG ACCTACAGCT TGCCAGCATG ATGGGGTGAC CACGCTGATC | 1550 |
| CTCCAGGGAC CAACTGTCAT TGTGACACTC CCCAGATGGA ATGTGTCCCA | 1600 |
| CATGATGGGC GTGCTGTGCT AGGACATCCA TAGGTTGGAG TTCAGGCAGC | 1650 |
| CTTAGGGTTA TGGCAGGCTC CCCTGCTTTG TATCCCCAAC CTCTTCTCGC | 1700 |
| TATTCCGAAA GGCTGGGTAA GTTTCTTTCC AAAACCTGTG TGTTCTTGGG | 1750 |
| GAAGTGTGGA CATCGTTCCC TGAGCAGGAT GCAGGCAGCT GGTTAGTCCG | 1800 |

| | |
|---|---|
| ATAAATACAT CAGCGTGTCC GTCTTTTCTA GGGTGCAATC CCTGGGTCTT | 1850 |
| TCATCATGTA AACTCTGCTC CATCCTTCAC TGGAAGACCT GTTCACACGT | 1900 |
| ATTTGTATTT GTCTTCCTGG AACTGTCAGG CTTTGTACCT GAGGATTTAG | 1950 |
| TGCTCTTTGC ACAGGGTTCA TTCAGCTCAG GGGGCCAGTT CACTGTGAAG | 2000 |
| ACGCCCTAAC ACCTAGACCC CCACCGAAGT CAACCTTCTG AGCCCTTGAG | 2050 |
| CACAGCTTTA TTGGAGGGAG AAGCGTGCTG GTAGACAGTC CTGAGCTCGG | 2100 |
| CATTGCTTCA AGGGTCGAGC GTGCGACCCT TGCCTCGCCT GCTCCGCCCC | 2150 |
| AGCTGGGCTC CCACGCCCTC TGGGACCGCC CGGCGCCCCC GCCTGACCAC | 2200 |
| GCCTCTTCGG ATCTCCCGCC CCCTGGCCGC CGGGGAAGGG GAGTGTTCGG | 2250 |
| GGCGTGGCGG GAGCACCCCC CAACCCCCGC CCGGGCTGCT GCGCGCCGGG | 2300 |
| CAGCCCCAGT TCAGTGCACT GTGGCAGCGG GGGTGGCGGG AGCAGCTGGC | 2350 |
| GCCGTGCGAT CCACTCCGGC GGGGGACTC AGTGGTGGGC GGCCGGCCAC | 2400 |
| TGGGACAGAG GAGACCCTGG AAAAGCGGGC CGAGAGACGA AGCCGCGCGT | 2450 |
| GGTGAGTTGG GCTCTAGCGG CCGGATCCCC CGGGCTGCAG GAATTCGATA | 2500 |
| TCAAGCTTGC ATGCCCGCGC GCGCTGCCTG AGGACGCCGC GGCCCCCGCC | 2550 |
| CCCGCCATGG GCGCCCCTGC CTGCGCCCTC GCGCTCTGCG TGGCCGTGGC | 2600 |
| CATCGTGGCC GGCGCCTCCT CGGAGTCCTT GGGGACGGAG CAGCGCGTCG | 2650 |
| TGGGGCGAGC GGCAGAAGTC CCGGGCCCAG AGCCCGGCCA GCAGGAGCAG | 2700 |
| TTGGTCTTCG GCAGCGGGGA TGCTGTGGAG CTGAGCTGTC CCCCGCCCGG | 2750 |
| GGGTGGTCCC ATGGGGCCCA CTGTCTGGGT CAAGGATGGC ACAGGGCTGG | 2800 |
| TGCCCTCGGA GCGTGTCCTG GTGGGGCCCC AGCGGCTGCA GGTGCTGAAT | 2850 |
| GCCTCCCACG AGGACTCCGG GGCCTACAGC TGCCGGCAGC GGCTCACGCA | 2900 |
| GCGCGTACTG TGCCACTTCA GTGTGCGGGT GACAGACGCT CCATCCTCGG | 2950 |
| GAGATGACGA AGACGGGGAG GACGAGGCTG AGGACACAGG TGTGGACACA | 3000 |
| GGGGCCCCTT ACTGGACACG GCCCGAGCGG ATGGACAAGA AGCTGCTGGC | 3050 |
| CGTGCCGGCC GCCAACACCG TCCGCTTCCG CTGCCCAGCC GCTGGCAACC | 3100 |
| CCACTCCCTC CATCTCCTGG CTGAAGAACG GCAGGGAGTT CCGCGGCGAG | 3150 |
| CACCGCATTG GAGGCATCAA GCTGCGGCAT CAGCAGTGGA GCCTGGTCAT | 3200 |
| GGAAAGCGTG GTGCCCTCGG ACCGCGGCAA CTACACCTGC GTCGTGGAGA | 3250 |
| ACAAGTTTGG CAGCATCCGG CAGACGTACA CGCTGGACGT GCTGGAGCGC | 3300 |
| TCCCCGCACC GGCCCATCCT GCAGGCGGGG CTGCCGGCCA ACCAGACGGC | 3350 |
| GGTGCTGGGC AGCGACGTGG AGTTCCACTG CAAGGTGTAC AGTGACGCAC | 3400 |
| AGCCCCACAT CCAGTGGCTC AAGCACGTGG AGGTGAACGG CAGCAAGGTG | 3450 |
| GGCCCGGACG GCACACCCTA CGTTACCGTG CTCAAGACGC GGGCGCTAA | 3500 |
| CACCACCGAC AAGGAGCTAG AGGTTCTCTC CTTGCACAAC GTCACCTTTG | 3550 |
| AGGACGCCGG GGAGTACACC TGCCTGGCGG GCAATTCTAT TGGGTTTTCT | 3600 |
| CATCACTCTG CGTGGCTGGT GGTGCTGCCA GCCGAGGAGG AGCTGGTGGA | 3650 |
| GGCTGACGAG GCGGGCAGTG TGTATGCAGG AATTCTCAGC TACAGGGTGG | 3700 |
| GCTTCTTCCT GTTCATCCTG GTGGTGGCGG CTGTGACGCT CTGCCGCCTG | 3750 |

| | |
|---|---|
| CGCAGCCCCC CCAAGAAAGG CCTGGGCTCC CCCACCGTGC ACAAGATCTC | 3800 |
| CCGCTTCCCG CTCAAGCGAC AGGTGTCCCT GGAGTCCAAC GCGTCCATGA | 3850 |
| GCTCCAACAC ACCACTGGTG CGCATCGCAA GGCTGTCCTC AGGGGAGGGC | 3900 |
| CCCACGCTGG CCAATGTCTC CGAGCTCGAG CTGCCTGCCG ACCCCAAATG | 3950 |
| GGAGCTGTCT CGGGCCCGGC TGACCCTGGG CAAGCCCCTT GGGGAGGGCT | 4000 |
| GCTTCGGCCA GGTGGTCATG GCGGAGGCCA TCGGCATTGA CAAGGACCGG | 4050 |
| GCCGCCAAGC CTGTCACCGT AGCCGTGAAG ATGCTGAAAG ACGATGCCAC | 4100 |
| TGACAAGGAC CTGTCGGACC TGGTGTCTGA GATGGAGATG ATGAAGATGA | 4150 |
| TCGGGAAACA CAAAAACATC ATCAACCTGC TGGGCGCCTG CACGCAGGGC | 4200 |
| GGGCCCCTGT ACGTGCTGGT GGAGTACGCG GCCAAGGGTA ACCTGCGGGA | 4250 |
| GTTTCTGCGG GCGCGGCGGC CCCCGGGCCT GGACTACTCC TTCGACACCT | 4300 |
| GCAAGCCGCC CGAGGAGCAG CTCACCTTCA AGGACCTGGT GTCCTGTGCC | 4350 |
| TACCAGGTGG CCCGGGGCAT GGAGTACTTG GCCTCCCAGA AGTGCATCCA | 4400 |
| CAGGGACCTG GCTGCCCGCA ATGTGCTGGT GACCGAGGAC AACGTGATGA | 4450 |
| AGATCGCAGA CTTCGGGCTG GCCCGGGACG TGCACAACCT CGACTACTAC | 4500 |
| AAGAAGACAA CCAACGGCCG GCTGCCCGTG AAGTGGATGG CGCCTGAGGC | 4550 |
| CTTGTTTGAC CGAGTCTACA CTCACCAGAG TGACGTCTGG TCCTTTGGGG | 4600 |
| TCCTGCTCTG GGAGATCTTC ACGCTGGGGG CTCCCCGTA CCCCGGCATC | 4650 |
| CCTGTGGAGG AGCTCTTCAA GCTGCTGAAG GAGGGCCACC GCATGGACAA | 4700 |
| GCCCGCCAAC TGCACACACG ACCTGTACAT GATCATGCGG GAGTGCTGGC | 4750 |
| ATGCCGCGCC CTCCCAGAGG CCCACCTTCA AGCAGCTGGT GGAGGACCTG | 4800 |
| GACCGTGTCC TTACCGTGAC GTCCACCGAC GAGTACCTGG ACCTGTCGGC | 4850 |
| GCCTTTCGAG CAGTACTCCC CGGGTGGCCA GGACACCCCC AGCTCCAGCT | 4900 |
| CCTCAGGGGA CGACTCCGTG TTTGCCCACG ACCTGCTGCC CCCGGCCCCA | 4950 |
| CCCAGCAGTG GGGGCTCGCG GACGTGAAGG GCCACTGGTC CCCAACAATG | 5000 |
| TGAGGGGTCC CTAGCAGCCC TCCCTGCTGC TGGTGCACAG CCACTCCCCG | 5050 |
| GCATGAGACT CAGTGCAGAT GGAGAGACAG CTACACAGAG CTTTGGTCTG | 5100 |
| TGTGTGTGTG TGTGCGTGTG TGTGTGTGTG TGCACATCCG CGTGTGCCTG | 5150 |
| TGTGCGTGCG CATCTTGCCT CCAGGTGCAG AGGTACCCTG GGTGTCCCCG | 5200 |
| CTGCTGTGCA ACGGTCTCCT GACTGGTGCT GCAGCACCGA GGGGCCTTTG | 5250 |
| TTCTGGGGGG ACCCAGTGCA GAATGTAAGT GGGCCCACCC GGTGGGACCC | 5300 |
| CGTGGGGCAG GGAGCTGGGC CCGACATGGC TCGGCCTCTG CCTTTGCACC | 5350 |
| ACGGGACATC ACAGGGTGCG CTCGGCCCCT CCCACACCCA AGCTGAGCC | 5400 |
| TGCAGGGAAG CCCCACATGT CCAGCACCTT GTGCCTGGGG TGTTAGTGGC | 5450 |
| ACCGCCTCCC CACCTCCAGG CTTTCCCACT TCCCACCCTG CCCCTCAGAG | 5500 |
| ACTGAAATTA CGGGTACCTG AAGATGGGAG CCTTTACCTT TTATGCAAAA | 5550 |
| GGTTTATTCC GGAAACTAGT GTACATTTCT ATAAATAGAT GCTGTGTATA | 5600 |
| TGGTATATAT ACATATATAT ATATAACATA TATGGAAGAG GAAAAGGCTG | 5650 |
| GTACAACGGA GGCCTGCGAC CCTGGGGGCA CAGGAGGCAG GCATGGCCCT | 5700 |
| GGGCGGGGCG TGGGGGGGCG TGGAGGGAGG CCCCAGGGGT CTCACCCATG | 5750 |

| | |
|---|---|
| CAAGCAGAGG ACCAGGGCTT TTTCTGGCAC CGCAGTTTTG TTTTAAAACT | 5800 |
| GGACCTGTAT ATTTGTAAAG CTATTTATGG GCCCCTGGCA CTCTTGTTCC | 5850 |
| CACACCCCAA CACTTCCAGC ATTTAGCTGG CCACATGGCG GAGAGTTTTA | 5900 |
| ATTTTTAACT TATTGACAAC CGAGAAGGTT TATCCCGCCG ATAGAGGGAC | 5950 |
| GGCCAAGAAT GTACGTCCAG CCTGCCCCGG AGCTGGAGGA TCC | 5993 |

(2) INFORMATION FOR SEQ ID NO: 2:

(i) SEQUENCE CHARACTERISTICS:
        (A) LENGTH: 5993
        (B) TYPE: nucleic acid
        (C) STRANDEDNESS: double
        (D) TOPOLOGY: linear (xi) SEQUENCE DESCRIPTION: SEQ ID NO: 2:

| | |
|---|---|
|         GGA TCC ACA AAT GTG ACC TTA TTT GGA AAA AGA GTC | 36 |
| TTG CAA GCA TAA CGA TGG GAA GAG GCT TGA GGT GAG ACC ATC TTC | 81 |
| ACT TTA TGA ACA ACT CTA AAT CCA ACC ACA AGT GTC CTT ATG CAG | 126 |
| GAC AGG AGA CGT GGG GAG GAT AGA AAA GGG CAC AGA AGC CAT GGG | 171 |
| AAG GGA GAG GCA GAG ACT AGA CTG AGA TGA CCC GTA AGC CAT TGG | 216 |
| ATG CCT GCA GGC CCC AGA GTT ATA ACA GGC AGG AAG AAG CCT ATT | 261 |
| CAG GGC CCC CAG CCC AAC TTG ACC TCA GAC TTC TGT TGT CCT GAA | 306 |
| TTG AAA AAG TAA ATT TAA GAC AAC CAG ATT TTA ATC TGG AAG TCG | 351 |
| GCT CAA TAC AGG TAA TAC AAG TTG TAG CCG GGC GTG GTA GCC CAC | 396 |
| GCC TTT AAT CCC AGC ACT CGG GAG GCA GAG GCA GGC GGA TTT CTG | 441 |
| AGT TCA AGG TCT GCC TGG TTT ACA AAG TGA GTT CAG GAC AGC CA | 486 |
| GGG CTA CAG AGA AAC CCT GTT TCG AAA AAC CAA AAA AAA AAA AAA | 531 |
| AAA AAA AAA AGG AAT ACA AGT TGT GAA TAG TTG TGA ACA CCA CAC | 576 |
| AGC TCA TTT TTA ATG AAG GGG CTG ATT CCC CCC CCC CCA CTG CTG | 621 |
| CAG TTG AGC AGG GGT CTA CAA AAG CTG GCC ATT GTA AGG CCA CAG | 666 |
| GGT TGG GGG AGG ATC AGA GGA ATG GGA GTA CCC TGG CTT AGA GTC | 711 |
| CTC TTT CCT GCA TGT GTT AGC CCA TTG GAA AAC AAG GTA GCT TGA | 756 |
| AAA GAG ATG GTC TGT TGG GCC ATG GGG TTC AAA AAA CAA CCA ACA | 801 |
| CCA TGG CCT GAG ATT CCT GAC TGG GTA TTT CTA ACA AGG AGG TCA | 846 |
| TCT CAA AAA TAA ATA ATT ATT GCT GTT TGG ATG GAT GCT CAG CTC | 891 |
| CCA GTT ACA GAG TGT GGA GGG TTC TGA TAA ATC CTC CAG ACG AAG | 936 |
| GGC GTG GAA ATA GGG TCA GAG CTC ACA TTC TGG TTC ATT TAC TG | 981 |
| ATA AAC TAA TCT GCC AAT AGA TTA GGG GAG AAT GTC TGC TAT GAC | 1026 |
| CCC CTG GGG TGG CAT CCT GGG AGA GGA CCT GTG GGC AGC TGC CTG | 1071 |
| GGG GTG CCA TGG GAA CCC AGG ACT GGA TTC TAG CCA GTC TGC AGG | 1116 |
| GAG GGG TCC TTG GCC AGA GCA GGA GTA ACA GTA GGC AGA GCT GCC | 1161 |
| CAG CTC TAG GGT GGA CAC ACA GGG ATG AGA GCA TGA GGG TTC TGG | 1206 |
| GGC CAG GGC TTT CCC TGC TCA GCT ATC TGG GAA AGA TAA GGG TGA | 1251 |
| TGA GTA AGC AGT GAA AGG TGT TGG TAA CCA CGA GCC ATT CCC | 1296 |

-continued

```
CCC CCA CCC CCC CCA TGA GCA GTT TAG TTC TTC AAG CCA CAT ACA       1341

GCC AGA CTG GGC AGA AGC ACT GAG CCA GGT CCC CAT GTA TCT GGC       1386

TCC CAT AGG CTT CAT CAG ACC TTG TGG AAC TTG TCT GAA AGT GAG       1431

ACA AGG TTC CCT GCC TTG TGA GGG TAG AGA GGC CAT CAG TCA CAG       1476

GGT GGT TGC TGT TAC AGA AGT TCT GCC AGG CAG GAC CTA CAG CTT       1521

GCC AGC ATG ATG GGG TGA CCA CGC TGA TCC TCC AGG GAC CAA CTG       1566

TCA TTG TGA CAC TCC CCA GAT GGA ATG TGT CCC ACA TGA TGG GCG       1611

TGC TGT GCT AGG ACA TCC ATA GGT TGG AGT TCA GGC AGC CTT AGG       1656

GTT ATG GCA GGC TCC CCT GCT TTG TAT CCC CAA CCT CTT CTC GCT       1701

ATT CCG AAA GGC TGG GTA AGT TTC TTT CCA AAA CCT GTG TGT TCT       1746

TGG GGA AGT GTG GAC ATC GTT CCC TGA GCA GGA TGC AGG CAG CTG       1791

GTT AGT CCG ATA AAT ACA TCA GCG TGT CCG TCT TTT CTA GGG TGC       1836

AAT CCC TGG GTC TTT CAT CAT GTA AAC TCT GCT CCA TCC TTC ACT       1881

GGA AGA CCT GTT CAC ACG TAT TTG TAT TTG TCT TCC TGG AAC TGT       1926

CAG GCT TTG TAC CTG AGG ATT TAG TGC TCT TTG CAC AGG GTT CAT       1971

TCA GCT CAG GGG GCC AGT TCA CTG TGA AGA CGC CCT AAC ACC TAG       2016

ACC CCC ACC GAA GTC AAC CTT CTG AGC CCT TGA GCA CAG CTT TAT       2061

TGG AGG GAG AAG CGT GCT GGT AGA CAG TCC TGA GCT CGG CAT TGC       2106

TTC AAG GGT CGA GCG TGC GAC CCT TGC CTC GCC TGC TCC GCC CCA       2151

GCT GGG CTC CCA CGC CCT CTG GGA CCG CCC GGC GCC CCC GCC TGA       2196

CCA CGC CTC TTC GGA TCT CCC GCC CCC TGG CCG CCG GGG AAG GGG       2241

AGT GTT CGG GGC GTG GCG GGA GCA CCC CCC AAC CCC CGC CGG GGC       2286

TGC TGC GCG CCG GGC AGC CCC AGT TCA GTG CAC TGT GGC AGC GGG       2331

GGT GGC GGG AGC AGC TGG CGC CGT GCG ATC CAC TCC GGC GGG GGG       2376

ACT CAG TGG TGG GCG GCC GGC CAC TGG GAC AGA GGA GAC CCT GGA       2421

AAA GCG GGC CGA GAG ACG GAG CCG CGC GTG GTG AGT TGG GCT CTA       2466

GCG GCC GGA TCC CCC GGG CTG CAG GAA TTC GAT ATC AAG CTT GCA       2511

TGC CGC GCG CTG CCT GAG GAC GCC GCG GCC CCC GCC CCC GCC       2556

ATG GGC GCC CCT GCC TGC GCC CTC GCG CTC TGC GTG GCC GTG GCC       2601
Met Gly Ala Pro Ala Cys Ala Leu Ala Leu Cys Val Ala Val Ala
          5              10              15

ATC GTG GCC GGC GCC TCC TCG GAG TCC TTG GGG ACG GAG CAG CGC       2646
Ile Val Ala Gly Ala Ser Ser Glu Ser Leu Gly Thr Glu Gln Arg
         20              25              30

GTC GTG GGG CGA GCG GCA GAA GTC CCG GGC CCA GAG CCC GGC CAG       2691
Val Val Gly Arg Ala Ala Glu Val Pro Gly Pro Glu Pro Gly Gln
         35              40              45

CAG GAG CAG TTG GTC TTC GGC AGC GGG GAT GCT GTG GAG CTG AGC       2736
Gln Glu Gln Leu Val Phe Gly Ser Gly Asp Ala Val Glu Leu Ser
         50              55              60

TGT CCC CCG CCC GGG GGT GGT CCC ATG GGG CCC ACT GTC TGG GTC       2781
Cys Pro Pro Pro Gly Gly Gly Pro Met Gly Pro Thr Val Trp Val
         65              70              75

AAG GAT GGC ACA GGG CTG GTG CCC TCG GAG CGT GTC CTG GTG GGG       2826
```

```
-continued

Lys Asp Gly Thr Gly Leu Val Pro Ser Glu Arg Val Leu Val Gly
            80                  85                  90

CCC CAG CGG CTG CAG GTG CTG AAT GCC TCC CAC GAG GAC TCC GGG                2871
Pro Gln Arg Leu Gln Val Leu Asn Ala Ser His Glu Asp Ser Gly
            95                 100                 105

GCC TAC AGC TGC CGG CAG CGG CTC ACG CAG CGC GTA CTG TGC CAC                2916
Ala Tyr Ser Cys Arg Gln Arg Leu Thr Gln Arg Val Leu Cys His
           110                 115                 120

TTC AGT GTG CGG GTG ACA GAC GCT CCA TCC TCG GGA GAT GAC GAA                2961
Phe Ser Val Arg Val Thr Asp Ala Pro Ser Ser Gly Asp Asp Glu
           125                 130                 135

GAC GGG GAG GAC GAG GCT GAG GAC ACA GGT GTG GAC ACA GGG GCC                3006
Asp Gly Glu Asp Glu Ala Glu Asp Thr Gly Val Asp Thr Gly Ala
           140                 145                 150

CCT TAC TGG ACA CGG CCC GAG CGG ATG GAC AAG AAG CTG CTG GCC                3051
Pro Tyr Trp Thr Arg Pro Glu Arg Met Asp Lys Lys Leu Leu Ala
           155                 160                 165

GTG CCG GCC GCC AAC ACC GTC CGC TTC CGC TGC CCA GCC GCT GGC                3096
Val Pro Ala Ala Asn Thr Val Arg Phe Arg Cys Pro Ala Ala Gly
           170                 175                 180

AAC CCC ACT CCC TCC ATC TCC TGG CTG AAG AAC GGC AGG GAG TTC                3141
Asn Pro Thr Pro Ser Ile Ser Trp Leu Lys Asn Gly Arg Glu Phe
           185                 190                 195

CGC GGC GAG CAC CGC ATT GGA GGC ATC AAG CTG CGG CAT CAG CAG                3186
Arg Gly Glu His Arg Ile Gly Gly Ile Lys Leu Arg His Gln Gln
           200                 205                 210

TGG AGC CTG GTC ATG GAA AGC GTG GTG CCC TCG GAC CGC GGC AAC                3231
Trp Ser Leu Val Met Glu Ser Val Val Pro Ser Asp Arg Gly Asn
           215                 220                 225

TAC ACC TGC GTC GTG GAG AAC AAG TTT GGC AGC ATC CGG CAG ACG                3276
Tyr Thr Cys Val Val Glu Asn Lys Phe Gly Ser Ile Arg Gln Thr
           230                 235                 240

TAC ACG CTG GAC GTG CTG GAG CGC TCC CCG CAC CGG CCC ATC CTG                3321
Tyr Thr Leu Asp Val Leu Glu Arg Ser Pro His Arg Pro Ile Leu
           245                 250                 255

CAG GCG GGG CTG CCG GCC AAC CAG ACG GCG GTG CTG GGC AGC GAC                3366
Gln Ala Gly Leu Pro Ala Asn Gln Thr Ala Val Leu Gly Ser Asp
           260                 265                 270

GTG GAG TTC CAC TGC AAG GTG TAC AGT GAC GCA CAG CCC CAC ATC                3411
Val Glu Phe His Cys Lys Val Tyr Ser Asp Ala Gln Pro His Ile
           275                 280                 285

CAG TGG CTC AAG CAC GTG GAG GTG AAC GGC AGC AAG GTG GGC CCG                3456
Gln Trp Leu Lys His Val Glu Val Asn Gly Ser Lys Val Gly Pro
           290                 295                 300

GAC GGC ACA CCC TAC GTT ACC GTG CTC AAG ACG GCG GGC GCT AAC                3501
Asp Gly Thr Pro Tyr Val Thr Val Leu Lys Thr Ala Gly Ala Asn
           305                 310                 315

ACC ACC GAC AAG GAG CTA GAG GTT CTC TCC TTG CAC AAC GTC ACC                3546
Thr Thr Asp Lys Glu Leu Glu Val Leu Ser Leu His Asn Val Thr
           320                 325                 330

TTT GAG GAC GCC GGG GAG TAC ACC TGC CTG GCG GGC AAT TCT ATT                3591
Phe Glu Asp Ala Gly Glu Tyr Thr Cys Leu Ala Gly Asn Ser Ile
           335                 340                 345

GGG TTT TCT CAT CAC TCT GCG TGG CTG GTG GTG CTG CCA GCC GAG                3636
Gly Phe Ser His His Ser Ala Trp Leu Val Val Leu Pro Ala Glu
           350                 355                 360

GAG GAG CTG GTG GAG GCT GAC GAG GCG GGC AGT GTG TAT GCA GGA                3681
Glu Glu Leu Val Glu Ala Asp Glu Ala Gly Ser Val Tyr Ala Gly
           365                 370                 375
```

```
ATT CTC AGC TAC AGG GTG GGC TTC TTC CTG TTC ATC CTG GTG GTG       3726
Ile Leu Ser Tyr Arg Val Gly Phe Phe Leu Phe Ile Leu Val Val
            380                 385                 390

GCG GCT GTG ACG CTC TGC CGC CTG CGC AGC CCC CCC AAG AAA GGC       3771
Ala Ala Val Thr Leu Cys Arg Leu Arg Ser Pro Pro Lys Lys Gly
            395                 400                 405

CTG GGC TCC CCC ACC GTG CAC AAG ATC TCC CGC TTC CCG CTC AAG       3816
Leu Gly Ser Pro Thr Val His Lys Ile Ser Arg Phe Pro Leu Lys
            410                 415                 420

CGA CAG GTG TCC CTG GAG TCC AAC GCG TCC ATG AGC TCC AAC ACA       3861
Arg Gln Val Ser Leu Glu Ser Asn Ala Ser Met Ser Ser Asn Thr
            425                 430                 435

CCA CTG GTG CGC ATC GCA AGG CTG TCC TCA GGG GAG GGC CCC ACG       3906
Pro Leu Val Arg Ile Ala Arg Leu Ser Ser Gly Glu Gly Pro Thr
            440                 445                 450

CTG GCC AAT GTC TCC GAG CTC GAG CTG CCT GCC GAC CCC AAA TGG       3951
Leu Ala Asn Val Ser Glu Leu Glu Leu Pro Ala Asp Pro Lys Trp
            455                 460                 465

GAG CTG TCT CGG GCC CGG CTG ACC CTG GGC AAG CCC CTT GGG GAG       3996
Glu Leu Ser Arg Ala Arg Leu Thr Leu Gly Lys Pro Leu Gly Glu
            470                 475                 480

GGC TGC TTC GGC CAG GTG GTC ATG GCG GAG GCC ATC GGC ATT GAC       4041
Gly Cys Phe Gly Gln Val Val Met Ala Glu Ala Ile Gly Ile Asp
            485                 490                 495

AAG GAC CGG GCC GCC AAG CCT GTC ACC GTA GCC GTG AAG ATG CTG       4086
Lys Asp Arg Ala Ala Lys Pro Val Thr Val Ala Val Lys Met Leu
            500                 505                 510

AAA GAC GAT GCC ACT GAC AAG GAC CTG TCG GAC CTG GTG TCT GAG       4131
Lys Asp Asp Ala Thr Asp Lys Asp Leu Ser Asp Leu Val Ser Glu
            515                 520                 525

ATG GAG ATG ATG AAG ATG ATC GGG AAA CAC AAA AAC ATC ATC AAC       4176
Met Glu Met Met Lys Met Ile Gly Lys His Lys Asn Ile Ile Asn
            530                 535                 540

CTG CTG GGC GCC TGC ACG CAG GGC GGG CCC CTG TAC GTG CTG GTG       4221
Leu Leu Gly Ala Cys Thr Gln Gly Gly Pro Leu Tyr Val Leu Val
            545                 550                 555

GAG TAC GCG GCC AAG GGT AAC CTG CGG GAG TTT CTG CGG GCG CGG       4266
Glu Tyr Ala Ala Lys Gly Asn Leu Arg Glu Phe Leu Arg Ala Arg
            560                 565                 570

CGG CCC CCG GGC CTG GAC TAC TCC TTC GAC ACC TGC AAG CCG CCC       4311
Arg Pro Pro Gly Leu Asp Tyr Ser Phe Asp Thr Cys Lys Pro Pro
            575                 580                 585

GAG GAG CAG CTC ACC TTC AAG GAC CTG GTG TCC TGT GCC TAC CAG       4356
Glu Glu Gln Leu Thr Phe Lys Asp Leu Val Ser Cys Ala Tyr Gln
            590                 595                 600

GTG GCC CGG GGC ATG GAG TAC TTG GCC TCC CAG AAG TGC ATC CAC       4401
Val Ala Arg Gly Met Glu Tyr Leu Ala Ser Gln Lys Cys Ile His
            605                 610                 615

AGG GAC CTG GCT GCC CGC AAT GTG CTG GTG ACC GAG GAC AAC GTG       4446
Arg Asp Leu Ala Ala Arg Asn Val Leu Val Thr Glu Asp Asn Val
            620                 625                 630

ATG AAG ATC GCA GAC TTC GGG CTG GCC CGG GAC GTG CAC AAC CTC       4491
Met Lys Ile Ala Asp Phe Gly Leu Ala Arg Asp Val His Asn Leu
            635                 640                 645

GAC TAC TAC AAG AAG ACA ACC AAC GGC CGG CTG CCC GTG AAG TGG       4536
Asp Tyr Tyr Lys Lys Thr Thr Asn Gly Arg Leu Pro Val Lys Trp
            650                 655                 660

ATG GCG CCT GAG GCC TTG TTT GAC CGA GTC TAC ACT CAC CAG AGT       4581
Met Ala Pro Glu Ala Leu Phe Asp Arg Val Tyr Thr His Gln Ser
            665                 670                 675
```

```
GAC GTC TGG TCC TTT GGG GTC CTG CTC TGG GAG ATC TTC ACG CTG        4626
Asp Val Trp Ser Phe Gly Val Leu Leu Trp Glu Ile Phe Thr Leu
                680                 685                 690
GGG GGC TCC CCG TAC CCC GGC ATC CCT GTG GAG GAG CTC TTC AAG        4671
Gly Gly Ser Pro Tyr Pro Gly Ile Pro Val Glu Glu Leu Phe Lys
                695                 700                 705
CTG CTG AAG GAG GGC CAC CGC ATG GAC AAG CCC GCC AAC TGC ACA        4716
Leu Leu Lys Glu Gly His Arg Met Asp Lys Pro Ala Asn Cys Thr
                710                 715                 720
CAC GAC CTG TAC ATG ATC ATG CGG GAG TGC TGG CAT GCC GCG CCC        4761
His Asp Leu Tyr Met Ile Met Arg Glu Cys Trp His Ala Ala Pro
                725                 730                 735
TCC CAG AGG CCC ACC TTC AAG CAG CTG GTG GAG GAC CTG GAC CGT        4806
Ser Gln Arg Pro Thr Phe Lys Gln Leu Val Glu Asp Leu Asp Arg
                740                 745                 750
GTC CTT ACC GTG ACG TCC ACC GAC GAG TAC CTG GAC CTG TCG GCG        4851
Val Leu Thr Val Thr Ser Thr Asp Glu Tyr Leu Asp Leu Ser Ala
                755                 760                 765
CCT TTC GAG CAG TAC TCC CCG GGT GGC CAG GAC ACC CCC AGC TCC        4896
Pro Phe Glu Gln Tyr Ser Pro Gly Gly Gln Asp Thr Pro Ser Ser
                770                 775                 780
AGC TCC TCA GGG GAC GAC TCC GTG TTT GCC CAC GAC CTG CTG CCC        4941
Ser Ser Ser Gly Asp Asp Ser Val Phe Ala His Asp Leu Leu Pro
                785                 790                 795
CCG GCC CCA CCC AGC AGT GGG GGC TCG CGG ACG TGA AGG GCC ACT        4986
Pro Ala Pro Pro Ser Ser Gly Gly Ser Arg Thr
                800                     805 806
GGT CCC CAA CAA TGT GAG GGG TCC CTA GCA GCC CTC CCT GCT GCT        5031
GGT GCA CAG CCA CTC CCC GGC ATG AGA CTC AGT GCA GAT GGA GAG        5076
ACA GCT ACA CAG AGC TTT GGT CTG TGT GTG TGT GTG TGC GTG TGT        5121
GTG TGT GTG TGC ACA TCC GCG TGT GCC TGT GTG CGT GCG CAT CTT        5166
GCC TCC AGG TGC AGA GGT ACC CTG GGT GTC CCC GCT GCT GTG CAA        5211
CGG TCT CCT GAC TGG TGC TGC AGC ACC GAG GGG CCT TTG TTC TGG        5256
GGG GAC CCA GTG CAG AAT GTA AGT GGG CCC ACC CGG TGG GAC CCC        5301
GTG GGG CAG GGA GCT GGG CCC GAC ATG GCT CGG CCT CTG CCT TTG        5346
CAC CAC GGG ACA TCA CAG GGT GCG CTC GGC CCC TCC CAC ACC CAA        5391
AGC TGA GCC TGC AGG GAA GCC CCA CAT GTC CAG CAC CTT GTG CCT        5436
GGG GTG TTA GTG GCA CCG CCT CCC CAC CTC CAG GCT TTC CCA CTT        5481
CCC ACC CTG CCC CTC AGA GAC TGA AAT TAC GGG TAC CTG AAG ATG        5526
GGA GCC TTT ACC TTT TAT GCA AAA GGT TTA TTC CGG AAA CTA GTG        5571
TAC ATT TCT ATA AAT AGA TGC TGT GTA TAT GGT ATA TAT ACA TAT        5616
ATA TAT ATA ACA TAT ATG GAA GAG GAA AAG GCT GGT ACA ACG GAG        5661
GCC TGC GAC CCT GGG GGC ACA GGA GGC AGG CAT GGC CCT GGG CGG        5706
GGC GTG GGG GGG CGT GGA GGG AGG CCC CAG GGG TCT CAC CCA TGC        5751
AAG CAG AGG ACC AGG GCT TTT TCT GGC ACC GCA GTT TTG TTT TAA        5796
AAC TGG ACC TGT ATA TTT GTA AAG CTA TTT ATG GGC CCC TGG CAC        5841
TCT TGT TCC CAC ACC CCA ACA CTT CCA GCA TTT AGC TGG CCA CAT        5886
GGC GGA GAG TTT TAA TTT TTA ACT TAT TGA CAA CCG AGA AGG TTT        5931
```

```
ATC CCG CCG ATA GAG GGA CGG CCA AGA ATG TAC GTC CAG CCT GCC      5976

CCG GAG CTG GAG GAT CC                                           5993
```

(2) INFORMATION FOR SEQ ID NO: 3:

(i) SEQUENCE CHARACTERISTICS:
        (A) LENGTH: 806
        (B) TYPE: amino acid
        (C) STRANDEDNESS: single
        (D) TOPOLOGY: linear (xi) SEQUENCE DESCRIPTION: SEQ ID NO: 3:

```
Met Gly Ala Pro Ala Cys Ala Leu Ala Leu Cys Val Ala Val Ala
                 5                  10                  15

Ile Val Ala Gly Ala Ser Ser Glu Ser Leu Gly Thr Glu Gln Arg
                20                  25                  30

Val Val Gly Arg Ala Ala Glu Val Pro Gly Pro Glu Pro Gly Gln
                35                  40                  45

Gln Glu Gln Leu Val Phe Gly Ser Gly Asp Ala Val Glu Leu Ser
                50                  55                  60

Cys Pro Pro Pro Gly Gly Gly Pro Met Gly Pro Thr Val Trp Val
                65                  70                  75

Lys Asp Gly Thr Gly Leu Val Pro Ser Glu Arg Val Leu Val Gly
                80                  85                  90

Pro Gln Arg Leu Gln Val Leu Asn Ala Ser His Glu Asp Ser Gly
                95                  100                 105

Ala Tyr Ser Cys Arg Gln Arg Leu Thr Gln Arg Val Leu Cys His
                110                 115                 120

Phe Ser Val Arg Val Thr Asp Ala Pro Ser Ser Gly Asp Asp Glu
                125                 130                 135

Asp Gly Glu Asp Glu Ala Glu Asp Thr Gly Val Asp Thr Gly Ala
                140                 145                 150

Pro Tyr Trp Thr Arg Pro Glu Arg Met Asp Lys Lys Leu Leu Ala
                155                 160                 165

Val Pro Ala Ala Asn Thr Val Arg Phe Arg Cys Pro Ala Ala Gly
                170                 175                 180

Asn Pro Thr Pro Ser Ile Ser Trp Leu Lys Asn Gly Arg Glu Phe
                185                 190                 195

Arg Gly Glu His Arg Ile Gly Gly Ile Lys Leu Arg His Gln Gln
                200                 205                 210

Trp Ser Leu Val Met Glu Ser Val Val Pro Ser Asp Arg Gly Asn
                215                 220                 225

Tyr Thr Cys Val Val Glu Asn Lys Phe Gly Ser Ile Arg Gln Thr
                230                 235                 240

Tyr Thr Leu Asp Val Leu Glu Arg Ser Pro His Arg Pro Ile Leu
                245                 250                 255

Gln Ala Gly Leu Pro Ala Asn Gln Thr Ala Val Leu Gly Ser Asp
                260                 265                 270

Val Glu Phe His Cys Lys Val Tyr Ser Asp Ala Gln Pro His Ile
                275                 280                 285

Gln Trp Leu Lys His Val Glu Val Asn Gly Ser Lys Val Gly Pro
                290                 295                 300

Asp Gly Thr Pro Tyr Val Thr Val Leu Lys Thr Ala Gly Ala Asn
                305                 310                 315

Thr Thr Asp Lys Glu Leu Glu Val Leu Ser Leu His Asn Val Thr
```

-continued

```
            320                 325                 330
Phe Glu Asp Ala Gly Glu Tyr Thr Cys Leu Ala Gly Asn Ser Ile
            335                 340                 345
Gly Phe Ser His His Ser Ala Trp Leu Val Val Leu Pro Ala Glu
            350                 355                 360
Glu Glu Leu Val Glu Ala Asp Glu Ala Gly Ser Val Tyr Ala Gly
            365                 370                 375
Ile Leu Ser Tyr Arg Val Gly Phe Phe Leu Phe Ile Leu Val Val
            380                 385                 390
Ala Ala Val Thr Leu Cys Arg Leu Arg Ser Pro Lys Lys Gly
            395                 400                 405
Leu Gly Ser Pro Thr Val His Lys Ile Ser Arg Phe Pro Leu Lys
            410                 415                 420
Arg Gln Val Ser Leu Glu Ser Asn Ala Ser Met Ser Ser Asn Thr
            425                 430                 435
Pro Leu Val Arg Ile Ala Arg Leu Ser Ser Gly Glu Gly Pro Thr
            440                 445                 450
Leu Ala Asn Val Ser Glu Leu Glu Leu Pro Ala Asp Pro Lys Trp
            455                 460                 465
Glu Leu Ser Arg Ala Arg Leu Thr Leu Gly Lys Pro Leu Gly Glu
            470                 475                 480
Gly Cys Phe Gly Gln Val Val Met Ala Glu Ala Ile Gly Ile Asp
            485                 490                 495
Lys Asp Arg Ala Ala Lys Pro Val Thr Val Ala Val Lys Met Leu
            500                 505                 510
Lys Asp Asp Ala Thr Asp Lys Asp Leu Ser Asp Leu Val Ser Glu
            515                 520                 525
Met Glu Met Met Lys Met Ile Gly Lys His Lys Asn Ile Ile Asn
            530                 535                 540
Leu Leu Gly Ala Cys Thr Gln Gly Gly Pro Leu Tyr Val Leu Val
            545                 550                 555
Glu Tyr Ala Ala Lys Gly Asn Leu Arg Glu Phe Leu Arg Ala Arg
            560                 565                 570
Arg Pro Pro Gly Leu Asp Tyr Ser Phe Asp Thr Cys Lys Pro Pro
            575                 580                 585
Glu Glu Gln Leu Thr Phe Lys Asp Leu Val Ser Cys Ala Tyr Gln
            590                 595                 600
Val Ala Arg Gly Met Glu Tyr Leu Ala Ser Gln Lys Cys Ile His
            605                 610                 615
Arg Asp Leu Ala Ala Arg Asn Val Leu Val Thr Glu Asp Asn Val
            620                 625                 630
Met Lys Ile Ala Asp Phe Gly Leu Ala Arg Asp Val His Asn Leu
            635                 640                 645
Asp Tyr Tyr Lys Lys Thr Thr Asn Gly Arg Leu Pro Val Lys Trp
            650                 655                 660
Met Ala Pro Glu Ala Leu Phe Asp Arg Val Tyr Thr His Gln Ser
            665                 670                 675
Asp Val Trp Ser Phe Gly Val Leu Leu Trp Glu Ile Phe Thr Leu
            680                 685                 690
Gly Gly Ser Pro Tyr Pro Gly Ile Pro Val Glu Glu Leu Phe Lys
            695                 700                 705
Leu Leu Lys Glu Gly His Arg Met Asp Lys Pro Ala Asn Cys Thr
            710                 715                 720
```

```
His Asp Leu Tyr Met Ile Met Arg Glu Cys Trp His Ala Ala Pro
            725                 730                 735

Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala
            755                 760                 765

Pro Phe Glu Gln Tyr Ser Pro Gly Gly Gln Asp Thr Pro Ser Ser
            770                 775                 780

Ser Ser Ser Gly Asp Asp Ser Val Phe Ala His Asp Leu Leu Pro
            785                 790                 795

Pro Ala Pro Pro Ser Ser Gly Gly Ser Arg Thr
            800                 805 806
```

(2) INFORMATION FOR SEQ ID NO: 4:

(i) SEQUENCE CHARACTERISTICS:
        (A) LENGTH: 8083
        (B) TYPE: nucleic acid
        (C) STRANDEDNESS: double
        (D) TOPOLOGY: linear (xi) SEQUENCE DESCRIPTION: SEQ ID NO: 4:

```
GGATCCACAA ATGTGACCTT ATTTGGAAAA AGAGTCTTGC AAGCATAACG           50

ATGGGAAGAG GCTTGAGGTG AGACCATCTT CACTTTATGA ACAACTCTAA          100

ATCCAACCAC AAGTGTCCTT ATGCAGGACA GGAGACGTGG GGAGGATAGA          150

AAAGGGCACA GAAGCCATGG GAAGGGAGAG GCAGAGACTA GACTGAGATG          200

ACCCGTAAGC CATTGGATGC CTGCAGGCCC CAGAGTTATA CAGGCAGGA           250

AGAAGCCTAT TCAGGGCCCC CAGCCCAACT TGACCTCAGA CTTCTGTTGT          300

CCTGAATTGA AAAGTAAAT TTAAGACAAC CAGATTTTAA TCTGGAAGTC           350

GGCTCAATAC AGGTAATACA AGTTGTAGCC GGGCGTGGTA GCCCACGCCT          400

TTAATCCCAG CACTCGGGAG GCAGAGGCAG GCGGATTTCT GAGTTCAAGG          450

TCTGCCTGGT TTACAAAGTG AGTTTCAGGA CAGCCAGGGC TACAGAGAAA          500

CCCTGTTTCG AAAAACCAAA AAAAAAAAAA AAAAAAAAAA AGGAATACAA          550

GTTGTGAATA GTTGTGAACA CCACACAGCT CATTTTTAAT GAAGGGGCTG          600

ATTCCCCCCC CCCCACTGCT GCAGTTGAGC AGGGGTCTAC AAAAGCTGGC          650

CATTGTAAGG CCACAGGGTT GGGGGAGGAT CAGAGGAATG GGAGTACCCT          700

GGCTTAGAGT CCTCTTTCCT GCATGTGTTA GCCCATTGGA AAACAAGGTA          750

GCTTGAAAAG AGATGGTCTG TTGGGCCATG GGGTTCAAAA AACAACCAAC          800

ACCATGGCCT GAGATTCCTG ACTGGGTATT TCTAACAAGG AGGTCATCTC          850

AAAAATAAAT AATTATTGCT GTTTGGATGG ATGCTCAGCT CCCAGTTACA          900

GAGTGTGGAG GGTTCTGATA AATCCTCCAG ACGAAGGGCG TGGAAATAGG          950

GGTCAGAGCT CACATTCTGG TTCATTTACT GATAAACTAA TCTGCCAATA         1000

GATTAGGGGA GAATGTCTGC TATGACCCCC TGGGGTGGCA TCCTGGGAGA         1050

GGACCTGTGG GCAGCTGCCT GGGGGTGCCA TGGGAACCCA GGACTGGATT         1100

CTAGCCAGTC TGCAGGGAGG GGTCCTTGGC CAGAGCAGGA GTAACAGTAG         1150

GCAGAGCTGC CCAGCTCTAG GGTGGACACA CAGGGATGAG AGCATGAGGG         1200

TTCTGGGGCC AGGGCTTTCC CTGCTCAGCT ATCTGGGAAA GATAAGGGTG         1250
```

```
ATGAGTAAGC CAGTGAAAGG TGTTGGTAAC CCACGAGCCA TTCCCCCCCC        1300

CACCCCCCCC ATGAGCAGTT TAGTTCTTCA AGCCACATAC AGCCAGACTG        1350

GGCAGAAGCA CTGAGCCAGG TCCCCATGTA TCTGGCTCCC ATAGGCTTCA        1400

TCAGACCTTG TGGAACTTGT CTGAAAGTGA GACAAGGTTC CCTGCCTTGT        1450

GAGGGTAGAG AGGCCATCAG TCACAGGGTG GTTGCTGTTA CAGAAGTTCT        1500

GCCAGGCAGG ACCTACAGCT TGCCAGCATG ATGGGGTGAC CACGCTGATC        1550

CTCCAGGGAC CAACTGTCAT TGTGACACTC CCCAGATGGA ATGTGTCCCA        1600

CATGATGGGC GTGCTGTGCT AGGACATCCA TAGGTTGGAG TTCAGGCAGC        1650

CTTAGGGTTA TGGCAGGCTC CCCTGCTTTG TATCCCCAAC CTCTTCTCGC        1700

TATTCCGAAA GGCTGGGTAA GTTTCTTTCC AAAACCTGTG TGTTCTTGGG        1750

GAAGTGTGGA CATCGTTCCC TGAGCAGGAT GCAGGCAGCT GGTTAGTCCG        1800

ATAAATACAT CAGCGTGTCC GTCTTTTCTA GGGTGCAATC CCTGGGTCTT        1850

TCATCATGTA AACTCTGCTC CATCCTTCAC TGGAAGACCT GTTCACACGT        1900

ATTTGTATTT GTCTTCCTGG AACTGTCAGG CTTTGTACCT GAGGATTTAG        1950

TGCTCTTTGC ACAGGGTTCA TTCAGCTCAG GGGGCCAGTT CACTGTGAAG        2000

ACGCCCTAAC ACCTAGACCC CCACCGAAGT CAACCTTCTG AGCCCTTGAG        2050

CACAGCTTTA TTGGAGGGAG AAGCGTGCTG GTAGACAGTC CTGAGCTCGG        2100

CATTGCTTCA AGGGTCGAGC GTGCGACCCT TGCCTCGCCT GCTCCGCCCC        2150

AGCTGGGCTC CCACGCCCTC TGGGACCGCC CGGCGCCCCC GCCTGACCAC        2200

GCCTCTTCGG ATCTCCCGCC CCCTGGCCGC CGGGGAAGGG GAGTGTTCGG        2250

GGCGTGGCGG GAGCACCCCC CAACCCCCGC CCGGGCTGCT GCGCGCCGGG        2300

CAGCCCCAGT TCAGTGCACT GTGGCAGCGG GGGTGGCGGG AGCAGCTGGC        2350

GCCGTGCGAT CCACTCCGGC GGGGGGACTC AGTGGTGGGC GGCCGGCCAC        2400

TGGGACAGAG GAGACCCTGG AAAAGCGGGC CGAGAGACGG AGCCGCGCGT        2450

GGTGAGTTGG GCTCTAGCGG CCGCCAGTGC ACTGTGGCAG CGGGGGTGGC        2500

GGGAGCAGCT GGCGCCGTGC GATCCACTCC GGCGGGGGGA CTCAGTGGTG        2550

GGCGGCCGGC CACTGGGACA GAGGAGACCC TGGAAAAGCG GTCCGAGAGA        2600

CGGAGCCGCG CGTGGTGAGT TGGGCTCTAG CGGCCGCCAG GTTAGTGTGA        2650

AGGACTCGCC TGGCACTCGG AGGTTCCGGG CGGGCTCAGA AGCAGTCAGG        2700

GGGTGAGATA TGCGGGAAGT GGAGCGGTTC GTAAGTGCGG CGAGGCCGGG        2750

GCAAGGCGCG GGCTTCCCGC TCTGGAAAGT TTGCGGCTAC TGCCTCCGTC        2800

CTGGGAGGGC TCTGCGGCAA CCAGGGAGGG AAGGAGGAGG GAGGAACCGC        2850

GGCTGGGAGG AGGCGGCCGG CGCCAGGCAG CCCGGGAGAG AGCTAGGAGT        2900

CGGCGGGCGG GGCGGCCGGG GGTCGGGGTT CAGGAGCGAG GCCGCGCTTC        2950

CCCGCTGCCC TCCGGAGTAA CTCAGTGCTC TCCTCCTGTA GTCTCCACAG        3000

AGGCGTTCTC CCACCGGCGC GGAGCCGCG TGGGGGGTTG CAGCATGCCC         3050

GCGCGCGCTG CTTGAGGACG CCGCGGCCCC CGCTCTGGAG CCATGGTAGT        3100

CCCGGCCTGC GTGCTAGTGT TCTGCGTGGC GGTCGTGGCT GGAGCTACTT        3150

CCGAGCCTCC TGGTCCAGAG CAGCGAGTTG TGCGGAGAGC GGCAGGTAAG        3200
```

| | |
|---|---|
| GACTGACCCA AGGTGTTCTT CTGGGGGCCG GCCCTGAATC ACAGGGGCTT | 3250 |
| TGGCAATGGT GAACAGCCCT TGGGTGAGGA AGGGGCGTCG GGTTGATTAG | 3300 |
| CACCACAGGG GCTAGTGCGC CGAGGTTTGT CCCCTGCCCC GCAGATCGCT | 3350 |
| GTCAGCTCGG ACGCGGCAGT TTATAGGGGT GTCTGTAGGC TGGGAGCCAC | 3400 |
| CACCCAAGTG CGAGGCGTCA CGTGGACCGG TGCCCGTGAC GGTGGTCCCA | 3450 |
| GGCAGAGGGG CGTTGGGAAG GCGCGCGAGC TGACTTCCCA CGATTCCTAT | 3500 |
| TGTTGCTTCT CGAATTTGAG AGGAGGAAAA ATGCCTGTTA TTGATTCAGC | 3550 |
| CGTTCTCCCG GAACAGTTCT TCCTCTGCTT CAGCTAAAGG AAGGCTGGAC | 3600 |
| GTTGCGGGGT GGATAGTAGT ATCCCAGCCA AAGCTCAGCT TCAGGGTTTC | 3650 |
| GCATGACAAG GTGACAGCTT CAGTGCGGCT GCTCCCCTCT TATCCTGTAG | 3700 |
| GCGGCCTGAG GGGTCGGTTC CCAGGGGCGC GCACAGACTG CCCTTCAGGC | 3750 |
| CGCACGCTGG GAGATGAGGG GCGGTTGTCC CAGGATCTTG GCGCCGCCTA | 3800 |
| GGTAGTCCCG CTGGCCACCA AAGTCCGATG GGACACTTGA ATGCCCTCAA | 3850 |
| ACGGGGCCCG GAGGCCAAGG ATGCGAAAGG GAGCCACGGT CCGCTCTGCG | 3900 |
| TCCCTTGGTT GTCCGGAGGT GCGACGCGCG CCGGCCCCGG CTGTGCCCGG | 3950 |
| TGGCAGCGTG GCAAAGCAGA GCAGCGGTCT GGCGGGAGGC CGCGCGAAGG | 4000 |
| GAGGCTTTCG CTCGGTAAGT TGTCGCCCCA CCCGAGCTGA GGCCCGAACA | 4050 |
| GCCGCTCCTT TGTACCTCGG CGGACACAAA CCGCGTATTG ATGGCGGCGC | 4100 |
| GGTCTCTCGG GGAGGTGCGA GTGCGGCGGG CGCAGCGGGA GGAGGCAGAT | 4150 |
| GGCGGTGTGC CCCTCCCGGC GCCCCGAGC CCCTCTCTCC AGCGGCTGCA | 4200 |
| GCCTCCTGGA ACAATGTCAT TTTCTTTCTT TCTTTCTTTC TTTCTTTTTT | 4250 |
| TTTATGAATG AAAGTGGGCC GGGAACTTGA ATGTGCGTGT CTTTCAGCGG | 4300 |
| CGTGACAGAG GCGGTCGGGA GGTCAGCGCG CGCTTTTAGC GCCTGCTAGG | 4350 |
| ACTGCCCTGC TTCCCGGGTG CCGAATGGCC CGCGAGGAGA CCACATTAGC | 4400 |
| ATGTGTATTC AGATGAAGAT ATTACTTCTT GCGTCGGGTG TCAGTGAGCT | 4450 |
| CGGGTAGGGG CGGCGGGGCG GAGCGCACAC CCTCTCTGTG CCTCAGGCAG | 4500 |
| TGACGGTGGC CTCCTGGCAC GACCCTGCTG CGGGAACCGA AGCTGAGCCG | 4550 |
| GCCCGCCCGG GATCGGTGGG ATCGCCCGCC CCTCGCTTCT GCGTTTGAGC | 4600 |
| TTGTGAGACA GGTAGGGAAT TGATAGGCCA ATAAACTTAA TCCGGTTCCT | 4650 |
| TAACGAGATG GGCCGGGCTG TAAAAATACA AAGACCTGGT GAAGTTTACA | 4700 |
| GAGGTCCGGG CTGGCGCTTT CCCTAGGAAC ATAAATTACC AAGCAGGAGC | 4750 |
| TGGCTGGGGT CAAGGGCTGT GCGGCGGGGC TAGGTACCGG CCTAACCTGG | 4800 |
| CCACCCTTGG TGAGGCAAGC CCTGCTGGTG TGCTTAGTGT GGGAGACAGT | 4850 |
| AACCCTTAGG GGATCTTAGT GGATCCCCCG GGCTGCAGAT CCCCCGGGCG | 4900 |
| CAGTAGTCCA GGGTTTCCTT GATGATGTCA TACTTATCCT GTCCCTTTTT | 4950 |
| TTTCCACAGC TCGCGGTTGA GGACAAACTC TTCGCGGTCT TTCCAGTGGG | 5000 |
| GATCGACGGT ATCGATCATG GTAGTCCCGG CCTGCGTGCT AGTGTTCTGC | 5050 |
| GTGGCGGTCG TGGCTGGAGC TACTTCCGAG CCTCCTGGTC CAGAGCAGCG | 5100 |
| AGTTGTGCGG AGAGCGGCAG AGGTTCCAGG GCCTGAACCT AGCCAGCAGG | 5150 |
| AGCAGGTGGC CTTCGGCAGT GGGGACACCG TGGAGCTGAG CTGCCATCCT | 5200 |

-continued

| | |
|---|---|
| CCTGGAGGTG CCCCCACAGG GCCCACGGTC TGGGCTAAGG ATGGTACAGG | 5250 |
| TCTGGTGGCC TCCCACCGCA TCCTGGTGGG GCCTCAGAGG CTGCAAGTGC | 5300 |
| TAAATGCCTC CCACGAAGAT GCAGGGGTCT ACAGCTGCCA GCACCGGCTC | 5350 |
| ACTCGGCGTG TGCTGTGCCA CTTCAGTGTG CGTGTAACAG ATGCTCCATC | 5400 |
| CTCAGGAGAT GACGAAGATG GGGAGGACGT GGCTGAAGAC ACAGGGGCTC | 5450 |
| CTTATTGGAC TCGCCCGGAG CGAATGGATA AGAAACTGCT TGCTGTGCCA | 5500 |
| GCCGCAAACA CTGTCCGCTT CCGCTGCCCA GCTGCTGGCA ACCCTACCCC | 5550 |
| CTCCATCTCC TGGCTGAAGA ATGGCAAAGA ATTCCGAGGG GAGCATCGCA | 5600 |
| TTGGGGGCAT CAAGCTCCGG CACCAGCAGT GGAGCTTGGT CATGGAAAGT | 5650 |
| GTGGTACCCT CCGATCGTGG CAACTATACC TGTGTAGTTG AGAACAAGTT | 5700 |
| TGGCAGCATC CGGCAGACAT ACACACTGGA TGTGCTGGAC GCTCCCCAC | 5750 |
| ACCGGCCCAT CCTGCAGGCT GGGCTGCCGG CCAACCAGAC AGCCATTCTA | 5800 |
| GGCAGTGACG TGGAGTTCCA CTGCAAGGTG TACAGCGATG CACAGCCACA | 5850 |
| CATCCAGTGG CTGAAGCACG TGGAAGTGAA CGGCAGCAAG GTGGGCCCTG | 5900 |
| ACGGCACGCC CTACGTCACT GTACTCAAGA CTGCAGGCGC TAACACCACC | 5950 |
| GACAAGGAGC TAGAGGTTCT GTCCTTGCAC AATGTCACCT TTGAGGACGC | 6000 |
| GGGGGAGTAC ACCTGCCTGG CGGGCAATTC TATTGGGTTT TCCCATCACT | 6050 |
| CTGCGTGGCT GGTGGTGCTG CCAGCTGAGG AGGAGCTGAT GGAAACTGAT | 6100 |
| GAGGCTGGCA GCGTGTACGC AGGCGTCCTC AGCTACAGGG TGGTCTTCTT | 6150 |
| CCTCTTCATC CTGGTGGTGG CAGCTGTGAT ACTCTGCCGC CTGCGCAGTC | 6200 |
| CCCCAAAGAA GGGCTTGGGC TCGCCCACCG TGCACAAGGT CTCTCGCTTC | 6250 |
| CCGCTTAAGC GACAGGTGTC CTTGGAATCT AACTCCTCTA TGAACTCCAA | 6300 |
| CACACCCCTT GTCCGGATTG CCCGGCTGTC CTCAGGAGAA GGTCCTGTTC | 6350 |
| TGGCCAATGT TTCTGAACTT GAGCTGCCTG CTGACCCCAA GTGGGAGCTA | 6400 |
| TCCAGGACCC GGCTGACACT TGGTAAGCCT CTTGGAGAAG GCTGCTTTGG | 6450 |
| ACAGGTGGTC ATGGCAGAAG CTATTGGCAT CGACAAGGAC CGTACTGCCA | 6500 |
| AGCCTGTCAC CGTGGCCGTG AAGATGCTGA AAGATGATGC GACTGACAAG | 6550 |
| GACCTGTCGG ACCTGGTATC TGAGATGGAG ATGATGAAAA TGATTGGCAA | 6600 |
| GCACAAGAAC ATCATTAACC TGCTGGGGGC GTGCACACAG GGTGGGCCCC | 6650 |
| TGTATGTGCT GGTGGAGTAC GCAGCCAAGG GCAATCTCCG GGAGTTCCTT | 6700 |
| CGGGCGCGGC GGCCTCCAGG CATGGACTAC TCCTTTGATG CCTGCAGGCT | 6750 |
| GCCAGAGGAA CAGCTCACCT GCAAGGATCT AGTGTCCTGT GCCTACCAGG | 6800 |
| TGGCACGGGG CATGGAATAC TTGGCTTCTC AGAAGTGTAT TCACAGAGAC | 6850 |
| TTGGCTGCCA GAAACGTCCT GGTGACCGAG GACAATGTGA TGAAGATTGC | 6900 |
| GGACTTTGGC CTGGCTCGAG ATGTGCACAA CCTGGACTAC TACAAGAAGA | 6950 |
| CCACAAATGG CCGGCTACCT GTGAAGTGGA TGGCACCAGA GGCCCTTTTT | 7000 |
| GACCGAGTCT ACACCCACCA GAGTGATGTT TGGTCTTTTG GTGTCCTCCT | 7050 |
| CTGGGAGATC TTTACGCCTG GGGGGCCATC ACCGTATCCT GGCATCCCAG | 7100 |
| TGGAAGAGCT TTTCAAGCTG TTGAAAGAGG GCCACCGCAT GGACAAGCCA | 7150 |

-continued

```
GCCAGCTGCA CACATGACCT GTACATGATC ATGCGGGAAT GTTGGCATGC        7200

GGTGCCTTCA CAGAGGCCCA CCTTCAAGCA GTTGGTAGAG GATTTAGACC        7250

GCATCCTCAC TGTGACATCA ACCGACGAGT ACTTGGACCT CTCCGTGCCG        7300

TTTGAGCAGT ACTCGCCAGG TGGCCAGGAC ACGCCTAGCT CCAGCTCGTC        7350

CGGAGATGAC TCGGTGTTCA CCCATGACCT GCTACCCCCA GGTCCACCCA        7400

GTAACGGGGG ACCTCGGACG TGAAGGGCCA ACAGTCCCAC AGACCAAGCC        7450

CCAGGCAATG TTTACGCGGA CCCTAGCCCG CCCTGCTACT GCTGGTGTGC        7500

AGTGGACCCT AGCCAGCCCA GTGCAATGGG CCAACAGTAG ACAAGACTTC        7550

CTGCGTGTTT ATCCTTGGCT CCTGGGTGCA GAGGCCCCTT GGGAACATGC        7600

ACTGCTGTAG AGTAATCTCC TGACTGGCCA GGGCCAGGAG CACCAAACAA        7650

GAATGTAAGA GGCCCACCCT TGCAACCCTG GGGTTCTGGC CCTCTCATTT        7700

CCCACTGCTA CCTTCCAGGG ACCATTGTGG AGAGGGCTAG ACTCCATGTC        7750

CAGAGTGGGC CTTGGCTTCT TGTTGCCCCA AGCCTGAGCC TACAGGGAGG        7800

CTCTGCTCTG TGTGGCAAAC CTCTCTCCTA CATGGCACCT TGCGCTGGGG        7850

GTGTCATAGC TCGACATCTC CAGGCTGCCT GCTTTCCACC CTGCCCCTCA        7900

GAGACAAATT ACGGGTACCT GAAGGGGGGG CATAATGTCT ATCAGAAAGG        7950

TTTATTCCAG AGGAAAATGT ACATTTATAT AAATAGATGT TGTGTATGAT        8000

ATAAATATAT ACATACATAT ATATAAGAAT ATCTATATGG AAAAAGGCAA        8050

AGTTGAGGCC CAAGGGAGCA AGATACTCCA TGG                          8083
```

(2) INFORMATION FOR SEQ ID NO: 5:

(i) SEQUENCE CHARACTERISTICS:
        (A) LENGTH: 8083
        (B) TYPE: nucleic acid
        (C) STRANDEDNESS: double
        (D) TOPOLOGY: linear (xi) SEQUENCE DESCRIPTION: SEQ ID NO: 5:

```
                G GAT CCA CAA ATG TGA CCT TAT            22

TTG GAA AAA GAG TCT TGC AAG CAT AAC GAT GGG AAG AGG CTT GAG    67

GTG AGA CCA TCT TCA CTT TAT GAA CAA CTC TAA ATC CAA CCA CAA   112

GTG TCC TTA TGC AGG ACA GGA GAC GTG GGG AGG ATA GAA AAG GGC   157

ACA GAA GCC ATG GGA AGG GAG AGG CAG AGA CTA GAC TGA GAT GAC   202

CCG TAA GCC ATT GGA TGC CTG CAG GCC CCA GAG TTA TAA CAG GCA   247

GGA AGA AGC CTA TTC AGG GCC CCC AGC CCA ACT TGA CCT CAG ACT   292

TCT GTT GTC CTG AAT TGA AAA AGT AAA TTT AAG ACA ACC AGA TTT   337

TAA TCT GGA AGT CGG CTC AAT ACA GGT AAT ACA AGT TGT AGC CGG   382

GCG TGG TAG CCC ACG CCT TTA ATC CCA GCA CTC GGG AGG CAG AGG   427

CAG GCG GAT TTC TGA GTT CAA GGT CTG CCT GGT TTA CAA AGT GAG   472

TTT CAG GAC AGC CAG GGC TAC AGA GAA ACC CTG TTT CGA AAA ACC   517

AAA AAA AAA AAA AAA AAA AAA GGA ATA CAA GTT GTG AAT AGT       562

TGT GAA CAC CAC ACA GCT CAT TTT AAT GAA GGG GCT GAT TCC CC    607

CCC CCC CAC TGC TGC AGT TGA GCA GGG GTC TAC AAA AGC TGG CCA   652
```

| | |
|---|---|
| TTG TAA GGC CAC AGG GTT GGG GGA GGA TCA GAG GAA TGG GAG TAC | 697 |
| CCT GGC TTA GAG TCC TCT TTC CTG CAT GTG TTA GCC CAT TGG AAA | 742 |
| ACA AGG TAG CTT GAA AAG AGA TGG TCT GTT GGG CCA TGG GGT TCA | 787 |
| AAA AAC AAC CAA CAC CAT GGC CTG AGA TTC CTG ACT GGG TAT TTC | 832 |
| TAA CAA GGA GGT CAT CTC AAA AAT AAA TAA TTA TTG CTG TTT GGA | 877 |
| TGG ATG CTC AGC TCC CAG TTA CAG AGT GTG GAG GGT TCT GAT AAA | 922 |
| TCC TCC AGA CGA AGG GCG TGG AAA TAG GGG TCA GAG CTC ACA TTC | 967 |
| TGG TTC ATT TAC TGA TAA ACT AAT CTG CCA ATA GAT TAG GGG AGA | 1012 |
| ATG TCT GCT ATG ACC CCC TGG GGT GGC ATC CTG GGA GAG GAC CTG | 1057 |
| TGG GCA GCT GCC TGG GGG TGC CAT GGG AAC CCA GGA CTG GAT TCT | 1102 |
| AGC CAG TCT GCA GGG AGG GGT CCT TGG CCA GAG CAG GAG TAA CAG | 1147 |
| TAG GCA GAG CTG CCC AGC TCT AGG GTG GAC ACA CAG GGA TGA GAG | 1192 |
| CAT GAG GGT TCT GGG GCC AGG GCT TTC CCT GCT CAG CTA TCT GGG | 1237 |
| AAA GAT AAG GGT GAT GAG TAA GCC AGT GAA AGG TGT TGG TAA CCC | 1282 |
| ACG AGC CAT TCC CCC CCA CCC CCC CAT GAG CAG TTT AGT TCT | 1327 |
| TCA AGC CAC ATA CAG CCA GAC TGG GCA GAA GCA CTG AGC CAG GTC | 1372 |
| CCC ATG TAT CTG GCT CCC ATA GGC TTC ATC AGA CCT TGT GGA ACT | 1417 |
| TGT CTG AAA GTG AGA CAA GGT TCC CTG CCT TGT GAG GGT AGA GAG | 1462 |
| GCC ATC AGT CAC AGG GTG GTT GCT GTT ACA GAA GTT CTG CCA GGC | 1507 |
| AGG ACC TAC AGC TTG CCA GCA TGA TGG GGT GAC CAC GCT GAT CCT | 1552 |
| CCA GGG ACC AAC TGT CAT TGT GAC ACT CCC CAG ATG GAA TGT GTC | 1597 |
| CCA CAT GAT GGG CGT GCT GTG CTA GGA CAT CCA TAG GTT GGA GTT | 1642 |
| CAG GCA GCC TTA GGG TTA TGG CAG GCT CCC CTG CTT TGT ATC CCC | 1687 |
| AAC CTC TTC TCG CTA TTC CGA AAG GCT GGG TAA GTT TCT TTC CAA | 1732 |
| AAC CTG TGT GTT CTT GGG GAA GTG TGG ACA TCG TTC CCT GAG CAG | 1777 |
| GAT GCA GGC AGC TGG TTA GTC CGA TAA ATA CAT CAG CGT GTC CGT | 1822 |
| CTT TTC TAG GGT GCA ATC CCT GGG TCT TTC ATC ATG TAA ACT CTG | 1867 |
| CTC CAT CCT TCA CTG GAA GAC CTG TTC ACA CGT ATT TGT ATT TGT | 1912 |
| CTT CCT GGA ACT GTC AGG CTT TGT ACC TGA GGA TTT AGT GCT CTT | 1957 |
| TGC ACA GGG TTC ATT CAG CTC AGG GGG CCA GTT CAC TGT GAA GAC | 2002 |
| GCC CTA ACA CCT AGA CCC CCA CCG AAG TCA ACC TTC TGA GCC CTT | 2047 |
| GAG CAC AGC TTT ATT GGA GGG AGA AGC GTG CTG GTA GAC AGT CCT | 2092 |
| GAG CTC GGC ATT GCT TCA AGG GTC GAG CGT GCG ACC CTT GCC TCG | 2137 |
| CCT GCT CCG CCC CAG CTG GCT CCA CGC CTC TGG GAC CGC CCG | 2182 |
| GCG CCC CCG CCT GAC CAC GCC TCT TCG GAT CTC CGC CCC CTG GCC | 2227 |
| CGC CGG GGA AGG GGA GTG TTC GGG GCG TGG CGG GAG CAC CCC CCA | 2272 |
| ACC CCC GCC CGG GCT GCT GCG CGC CGG GCA GCC CCA GTT CAG TGC | 2317 |
| ACT GTG GCA GCG GGG GTG GCG GGA GCA GCT GGC GCC GTG CGA TCC | 2362 |
| ACT CCG GCG GGG GGA CTC AGT GGT GGG CGG CCG GCC ACT GGG ACA | 2407 |
| GAG GAG ACC CTG GAA AAG CGG GCC GAG AGA CGG AGC CGC GCG TGG | 2452 |

-continued

```
TGA GTT GGG CTC TAG CGG CCG CCA GTG CAC TGT GGC AGC GGG GGT        2497

GGC GGG AGC AGC TGG CGC CGT GCG ATC CAC TCC GGC GGG GGG ACT        2542

CAG TGG TGG GCG GCC GGC CAC TGG GAC AGA GGA GAC CCT GGA AAA        2587

GCG GTC CGA GAG ACG GAG CCG CGC GTG GTG AGT TGG GCT CTA GCG        2632

GCC GCC AGG TTA GTG TGA AGG ACT CGC CTG GCA CTC GGA GGT TCC        2677

GGG CGG GCT CAG AAG CAG TCA GGG GGT GAG ATA TGC GGG AAG TGG        2722

AGC GGT TCG TAA GTG CGG CGA GGC CGG GGC AAG GCG CGG GCT TCC        2767

CGC TCT GGA AAG TTT GCG GCT ACT GCC TCC GTC CTG GGA GGG CTC        2812

TGC GGC AAC CAG GGA GGG AAG GAG GAG GGA GGA ACC GCG GCT GGG        2857

AGG AGG CGG CCG GCG CCA GGC AGC CCG GGA GAG AGC TAG GAG TCG        2902

GCG GGC GGG GCG GCC GGG GGT CGG GGT TCA GGA GCG AGG CCG CGC        2947

TTC CCC GCT GCC CTC CGG AGT AAC TCA GTG CTC TCC TCC TGT AGT        2992

CTC CAC AGA GGC GTT CTC CCA CCG GCG CCG GAG CCG CGT GGG GGG        3037

TTG CAG CAT GCC CGC GCG CGC TGC TTG AGG ACG CCG CGG CCC CCG        3082

CTC TGG AGC CAT GGT AGT CCC GGC CTG CGT GCT AGT GTT CTG CGT        3127

GGC GGT CGT GGC TGG AGC TAC TTC CGA GCC TCC TGG TCC AGA GCA        3172

GCG AGT TGT GCG GAG AGC GGC AGG TAA GGA CTG ACC CAA GGT GTT        3217

CTT CTG GGG GCC GGC CCT GAA TCA CAG GGG CTT TGG CAA TGG TGA        3262

ACA GCC CTT GGG TGA GGA AGG GGC GTC GGG TTG ATT AGC ACC ACA        3307

GGG GCT AGT GCG CCG AGG TTT GTC CCC TGC CCC GCA GAT CGC TGT        3352

CAG CTC GGA CGC GGC AGT TTA TAG GGG TGT CTG TAG GCT GGG AGC        3397

CAC CAC CCA AGT GCG AGG CGT CAC GTG GAC CGG TGC CCG TGA CGG        3442

TGG TCC CAG GCA GAG GGG CGT TGG GAA GGC GCG CGA GCT GAC TTC        3487

CCA CGA TTC CTA TTG TTG CTT CTC GAA TTT GAG AGG AGG AAA AAT        3532

GCC TGT TAT TGA TTC AGC CGT TCT CCC GGA ACA GTT CTT CCT CTG        3577

CTT CAG CTA AAG GAA GGC TGG ACG TTG CGG GGT GGA TAG TAG TAT        3622

CCC AGC CAA AGC TCA GCT TCA GGG TTT CGC ATG ACA AGG TGA CAG        3667

CTT CAG TGC GGC TGC TCC CCT CTT ATC CTG TAG GCG GCC TGA GGG        3712

GTC GGT TCC CAG GGG CGC GCA CAG ACT GCC CTT CAG GCC GCA CGC        3757

TGG GAG ATG AGG GGC GGT TGT CCC AGG ATC TTG GCG CCG CCT AGG        3802

TAG TCC CGC TGG CCA CCA AAG TCC GAT GGG ACA CTT GAA TGC CCT        3847

CAA ACG GGG CCC GGA GGC CAA GGA TGC GAA AGG GAG CCA CGG TCC        3892

GCT CTG CGT CCC TTG GTT GTC CGG AGG TGC GAC GCG CGC CGG CCC        3937

CGG CTG TGC CCG GTG GCA GCG TGG CAA AGC AGA GCA GCG GTC TGG        3982

CGG GAG GCC GCG CGA AGG GAG GCT TTC GCT CGG TAA GTT GTC GCC        4027

CCA CCC GAG CTG AGG CCC GAA CAG CCG CTC CTT TGT ACC TCG GCG        4072

GAC ACA AAC CGC GTA TTG ATG GCG GCG CGG TCT CTC GGG GAG GTG        4117

CGA GTG CGG CGG GCG CAG CGG GAG GAG GCA GAT GGC GGT GTG CCC        4162

CTC CCG GCG CCC CCG AGC CCC TCT CTC CAG CGG CTG CAG CCT CCT        4207
```

```
GGA ACA ATG TCA TTT TCT TTC TTT CTT TCT TTC TTT CTT TTT TTT        4252

TAT GAA TGA AAG TGG GCC GGG AAC TTG AAT GTG CGT GTC TTT CAG        4297

CGG CGT GAC AGA GGC GGT CGG GAG GTC AGC GCG CGC TTT TAG CGC        4342

CTG CTA GGA CTG CCC TGC TTC CCG GGT GCC GAA TGG CCC GCG AGG        4387

AGA CCA CAT TAG CAT GTG TAT TCA GAT GAA GAT ATT ACT TCT TGC        4432

GTC GGG TGT CAG TGA GCT CGG GTA GGG GCG GCG GGG CGG AGC GCA        4477

CAC CCT CTC TGT GCC TCA GGC AGT GAC GGT GGC CTC CTG GCA CGA        4522

CCC TGC TGC GGG AAC CGA AGC TGA GCC GGC CCG CCC GGG ATC GGT        4567

GGG ATC GCC CGC CCC TCG CTT CTG CGT TTG AGC TTG TGA GAC AGG        4612

TAG GGA ATT GAT AGG CCA ATA AAC TTA ATC CGG TTC CTT AAC GAG        4657

ATG GGC CGG GCT GTA AAA ATA CAA AGA CCT GGT GAA GTT TAC AGA        4702

GGT CCG GGC TGG CGC TTT CCC TAG GAA CAT AAA TTA CCA AGC AGG        4747

AGC TGG CTG GGG TCA AGG GCT GTG CGG CGG GGC TAG GTA CCG GCC        4792

TAA CCT GGC CAC CCT TGG TGA GGC AAG CCC TGC TGG TGT GCT TAG        4837

TGT GGG AGA CAG TAA CCC TTA GGG GAT CTT AGT GGA TCC CCC GGG        4882

CTG CAG ATC CCC CGG GCG CAG TAG TCC AGG GTT TCC TTG ATG ATG        4927

TCA TAC TTA TCC TGT CCC TTT TTT TTC CAC AGC TCG CGG TTG AGG        4972

ACA AAC TCT TCG CGG TCT TTC CAG TGG GGA TCG ACG GTA TCG ATC        5017

ATG GTA GTC CCG GCC TGC GTG CTA GTG TTC TGC GTG GCG GTC GTG        5062
Met Val Val Pro Ala Cys Val Leu Val Phe Cys Val Ala Val Val
              5                  10                  15

GCT GGA GCT ACT TCC GAG CCT CCT GGT CCA GAG CAG CGA GTT GTG        5107
Ala Gly Ala Thr Ser Glu Pro Pro Gly Pro Glu Gln Arg Val Val
             20                  25                  30

CGG AGA GCG GCA GAG GTT CCA GGG CCT GAA CCT AGC CAG CAG GAG        5152
Arg Arg Ala Ala Glu Val Pro Gly Pro Glu Pro Ser Gln Gln Glu
             35                  40                  45

CAG GTG GCC TTC GGC AGT GGG GAC ACC GTG GAG CTG AGC TGC CAT        5197
Gln Val Ala Phe Gly Ser Gly Asp Thr Val Glu Leu Ser Cys His
             50                  55                  60

CCT CCT GGA GGT GCC CCC ACA GGG CCC ACG GTC TGG GCT AAG GAT        5242
Pro Pro Gly Gly Ala Pro Thr Gly Pro Thr Val Trp Ala Lys Asp
             65                  70                  75

GGT ACA GGT CTG GTG GCC TCC CAC CGC ATC CTG GTG GGG CCT CAG        5287
Gly Thr Gly Leu Val Ala Ser His Arg Ile Leu Val Gly Pro Gln
             80                  85                  90

AGG CTG CAA GTG CTA AAT GCC TCC CAC GAA GAT GCA GGG GTC TAC        5332
Arg Leu Gln Val Leu Asn Ala Ser His Glu Asp Ala Gly Val Tyr
             95                 100                 105

AGC TGC CAG CAC CGG CTC ACT CGG CGT GTG CTG TGC CAC TTC AGT        5377
Ser Cys Gln His Arg Leu Thr Arg Arg Val Leu Cys His Phe Ser
            110                 115                 120

GTG CGT GTA ACA GAT GCT CCA TCC TCA GGA GAT GAC GAA GAT GGG        5422
Val Arg Val Thr Asp Ala Pro Ser Ser Gly Asp Asp Glu Asp Gly
            125                 130                 135

GAG GAC GTG GCT GAA GAC ACA GGG GCT CCT TAT TGG ACT CGC CCG        5467
Glu Asp Val Ala Glu Asp Thr Gly Ala Pro Tyr Trp Thr Arg Pro
            140                 145                 150

GAG CGA ATG GAT AAG AAA CTG CTT GCT GTG CCA GCC GCA AAC ACT        5512
Glu Arg Met Asp Lys Lys Leu Leu Ala Val Pro Ala Ala Asn Thr
            155                 160                 165
```

```
GTC CGC TTC CGC TGC CCA GCT GCT GGC AAC CCT ACC CCC TCC ATC       5557
Val Arg Phe Arg Cys Pro Ala Ala Gly Asn Pro Thr Pro Ser Ile
                170                 175                 180

TCC TGG CTG AAG AAT GGC AAA GAA TTC CGA GGG GAG CAT CGC ATT       5602
Ser Trp Leu Lys Asn Gly Lys Glu Phe Arg Gly Glu His Arg Ile
                185                 190                 195

GGG GGC ATC AAG CTC CGG CAC CAG CAG TGG AGC TTG GTC ATG GAA       5647
Gly Gly Ile Lys Leu Arg His Gln Gln Trp Ser Leu Val Met Glu
                200                 205                 210

AGT GTG GTA CCC TCC GAT CGT GGC AAC TAT ACC TGT GTA GTT GAG       5692
Ser Val Val Pro Ser Asp Arg Gly Asn Tyr Thr Cys Val Val Glu
                215                 220                 225

AAC AAG TTT GGC AGC ATC CGG CAG ACA TAC ACA CTG GAT GTG CTG       5737
Asn Lys Phe Gly Ser Ile Arg Gln Thr Tyr Thr Leu Asp Val Leu
                230                 235                 240

GAG CGC TCC CCA CAC CGG CCC ATC CTG CAG GCT GGG CTG CCG GCC       5782
Glu Arg Ser Pro His Arg Pro Ile Leu Gln Ala Gly Leu Pro Ala
                245                 250                 255

AAC CAG ACA GCC ATT CTA GGC AGT GAC GTG GAG TTC CAC TGC AAG       5827
Asn Gln Thr Ala Ile Leu Gly Ser Asp Val Glu Phe His Cys Lys
                260                 265                 270

GTG TAC AGC GAT GCA CAG CCA CAC ATC CAG TGG CTG AAG CAC GTG       5872
Val Tyr Ser Asp Ala Gln Pro His Ile Gln Trp Leu Lys His Val
                275                 280                 285

GAA GTG AAC GGC AGC AAG GTG GGC CCT GAC GGC ACG CCC TAC GTC       5917
Glu Val Asn Gly Ser Lys Val Gly Pro Asp Gly Thr Pro Tyr Val
                290                 295                 300

ACT GTA CTC AAG ACT GCA GGC GCT AAC ACC ACC GAC AAG GAG CTA       5962
Thr Val Leu Lys Thr Ala Gly Ala Asn Thr Thr Asp Lys Glu Leu
                305                 310                 315

GAG GTT CTG TCC TTG CAC AAT GTC ACC TTT GAG GAC GCG GGG GAG       6007
Glu Val Leu Ser Leu His Asn Val Thr Phe Glu Asp Ala Gly Glu
                320                 325                 330

TAC ACC TGC CTG GCG GGC AAT TCT ATT GGG TTT TCC CAT CAC TCT       6052
Tyr Thr Cys Leu Ala Gly Asn Ser Ile Gly Phe Ser His His Ser
                335                 340                 345

GCG TGG CTG GTG GTG CTG CCA GCT GAG GAG GAG CTG ATG GAA ACT       6097
Ala Trp Leu Val Val Leu Pro Ala Glu Glu Glu Leu Met Glu Thr
                350                 355                 360

GAT GAG GCT GGC AGC GTG TAC GCA GGC GTC CTC AGC TAC AGG GTG       6142
Asp Glu Ala Gly Ser Val Tyr Ala Gly Val Leu Ser Tyr Arg Val
                365                 370                 375

GTC TTC TTC CTC TTC ATC CTG GTG GTG GCA GCT GTG ATA CTC TGC       6187
Val Phe Phe Leu Phe Ile Leu Val Val Ala Ala Val Ile Leu Cys
                380                 385                 390

CGC CTG CGC AGT CCC CCA AAG AAG GGC TTG GGC TCG CCC ACC GTG       6232
Arg Leu Arg Ser Pro Pro Lys Lys Gly Leu Gly Ser Pro Thr Val
                395                 400                 405

CAC AAG GTC TCT CGC TTC CCG CTT AAG CGA CAG GTG TCC TTG GAA       6277
His Lys Val Ser Arg Phe Pro Leu Lys Arg Gln Val Ser Leu Glu
                410                 415                 420

TCT AAC TCC TCT ATG AAC TCC AAC ACA CCC CTT GTC CGG ATT GCC       6322
Ser Asn Ser Ser Met Asn Ser Asn Thr Pro Leu Val Arg Ile Ala
                425                 430                 435

CGG CTG TCC TCA GGA GAA GGT CCT GTT CTG GCC AAT GTT TCT GAA       6367
Arg Leu Ser Ser Gly Glu Gly Pro Val Leu Ala Asn Val Ser Glu
                440                 445                 450

CTT GAG CTG CCT GCT GAC CCC AAG TGG GAG CTA TCC AGG ACC CGG       6412
Leu Glu Leu Pro Ala Asp Pro Lys Trp Glu Leu Ser Arg Thr Arg
```

```
                  455                 460                 465
CTG ACA CTT GGT AAG CCT CTT GGA GAA GGC TGC TTT GGA CAG GTG     6457
Leu Thr Leu Gly Lys Pro Leu Gly Glu Gly Cys Phe Gly Gln Val
                  470                 475                 480

GTC ATG GCA GAA GCT ATT GGC ATC GAC AAG GAC CGT ACT GCC AAG     6502
Val Met Ala Glu Ala Ile Gly Ile Asp Lys Asp Arg Thr Ala Lys
                  485                 490                 495

CCT GTC ACC GTG GCC GTG AAG ATG CTG AAA GAT GAT GCG ACT GAC     6547
Pro Val Thr Val Ala Val Lys Met Leu Lys Asp Asp Ala Thr Asp
                  500                 505                 510

AAG GAC CTG TCG GAC CTG GTA TCT GAG ATG GAG ATG ATG AAA ATG     6592
Lys Asp Leu Ser Asp Leu Val Ser Glu Met Glu Met Met Lys Met
                  515                 520                 525

ATT GGC AAG CAC AAG AAC ATC ATT AAC CTG CTG GGG GCG TGC ACA     6637
Ile Gly Lys His Lys Asn Ile Ile Asn Leu Leu Gly Ala Cys Thr
                  530                 535                 540

CAG GGT GGG CCC CTG TAT GTG CTG GTG GAG TAC GCA GCC AAG GGC     6682
Gln Gly Gly Pro Leu Tyr Val Leu Val Glu Tyr Ala Ala Lys Gly
                  545                 550                 555

AAT CTC CGG GAG TTC CTT CGG GCG CGG CGG CCT CCA GGC ATG GAC     6727
Asn Leu Arg Glu Phe Leu Arg Ala Arg Arg Pro Pro Gly Met Asp
                  560                 565                 570

TAC TCC TTT GAT GCC TGC AGG CTG CCA GAG GAA CAG CTC ACC TGC     6772
Tyr Ser Phe Asp Ala Cys Arg Leu Pro Glu Glu Gln Leu Thr Cys
                  575                 580                 585

AAG GAT CTA GTG TCC TGT GCC TAC CAG GTG GCA CGG GGC ATG GAA     6817
Lys Asp Leu Val Ser Cys Ala Tyr Gln Val Ala Arg Gly Met Glu
                  590                 595                 600

TAC TTG GCT TCT CAG AAG TGT ATT CAC AGA GAC TTG GCT GCC AGA     6862
Tyr Leu Ala Ser Gln Lys Cys Ile His Arg Asp Leu Ala Ala Arg
                  605                 610                 615

AAC GTC CTG GTG ACC GAG GAC AAT GTG ATG AAG ATT GCG GAC TTT     6907
Asn Val Leu Val Thr Glu Asp Asn Val Met Lys Ile Ala Asp Phe
                  620                 625                 630

GGC CTG GCT CGA GAT GTG CAC AAC CTG GAC TAC TAC AAG AAG ACC     6952
Gly Leu Ala Arg Asp Val His Asn Leu Asp Tyr Tyr Lys Lys Thr
                  635                 640                 645

ACA AAT GGC CGG CTA CCT GTG AAG TGG ATG GCA CCA GAG GCC CTT     6997
Thr Asn Gly Arg Leu Pro Val Lys Trp Met Ala Pro Glu Ala Leu
                  650                 655                 660

TTT GAC CGA GTC TAC ACC CAC CAG AGT GAT GTT TGG TCT TTT GGT     7042
Phe Asp Arg Val Tyr Thr His Gln Ser Asp Val Trp Ser Phe Gly
                  665                 670                 675

GTC CTC CTC TGG GAG ATC TTT ACG CCT GGG GGG CCA TCA CCG TAT     7087
Val Leu Leu Trp Glu Ile Phe Thr Pro Gly Gly Pro Ser Pro Tyr
                  680                 685                 690

CCT GGC ATC CCA GTG GAA GAG CTT TTC AAG CTG TTG AAA GAG GGC     7132
Pro Gly Ile Pro Val Glu Glu Leu Phe Lys Leu Leu Lys Glu Gly
                  695                 700                 705

CAC CGC ATG GAC AAG CCA GCC AGC TGC ACA CAT GAC CTG TAC ATG     7177
His Arg Met Asp Lys Pro Ala Ser Cys Thr His Asp Leu Tyr Met
                  710                 715                 720

ATC ATG CGG GAA TGT TGG CAT GCG GTG CCT TCA CAG AGG CCC ACC     7222
Ile Met Arg Glu Cys Trp His Ala Val Pro Ser Gln Arg Pro Thr
                  725                 730                 735

TTC AAG CAG TTG GTA GAG GAT TTA GAC CGC ATC CTC ACT GTG ACA     7267
Phe Lys Gln Leu Val Glu Asp Leu Asp Arg Ile Leu Thr Val Thr
                  740                 745                 750

TCA ACC GAC GAG TAC TTG GAC CTC TCC GTG CCG TTT GAG CAG TAC     7312
```

```
Ser Thr Asp Glu Tyr Leu Asp Leu Ser Val Pro Phe Glu Gln Tyr
            755                 760                 765

TCG CCA GGT GGC CAG GAC ACG CCT AGC TCC AGC TCG TCC GGA GAT      7357
Ser Pro Gly Gly Gln Asp Thr Pro Ser Ser Ser Ser Ser Gly Asp
            770                 775                 780

GAC TCG GTG TTC ACC CAT GAC CTG CTA CCC CCA GGT CCA CCC AGT      7402
Asp Ser Val Phe Thr His Asp Leu Leu Pro Pro Gly Pro Pro Ser
            785                 790                 795

AAC GGG GGA CCT CGG ACG TGA AGG GCC AAC AGT CCC ACA GAC CAA      7447
Asn Gly Gly Pro Arg Thr
            800

GCC CCA GGC AAT GTT TAC GCG GAC CCT AGC CCG CCC TGC TAC TGC      7492

TGG TGT GCA GTG GAC CCT AGC CAG CCC AGT GCA ATG GGC CAA CAG      7537

TAG ACA AGA CTT CCT GCG TGT TTA TCC TTG GCT CCT GGG TGC AGA      7582

GGC CCC TTG GGA ACA TGC ACT GCT GTA GAG TAA TCT CCT GAC TGG      7627

CCA GGG CCA GGA GCA CCA AAC AAG AAT GTA AGA GGC CCA CCC TTG      7672

CAA CCC TGG GGT TCT GGC CCT CTC ATT TCC CAC TGC TAC CTT CCA      7717

GGG ACC ATT GTG GAG AGG GCT AGA CTC CAT GTC CAG AGT GGG CCT      7762

TGG CTT CTT GTT GCC CCA AGC CTG AGC CTA CAG GGA GGC TCT GCT      7807

CTG TGT GGC AAA CCT CTC TCC TAC ATG GCA CCT GCG CTG GGG GT       7852

GTC ATA GCT CGA CAT CTC CAG GCT GCC TGC TTT CCA CCC TGC CCC      7897

TCA GAG ACA AAT TAC GGG TAC CTG AAG GGG GGG CAT AAT GTC TAT      7942

CAG AAA GGT TTA TTC CAG AGG AAA ATG TAC ATT TAT ATA AAT AGA      7987

TGT TGT GTA TGA TAT AAA TAT ATA CAT ACA TAT ATA TAA GAA TAT      8032

CTA TAT GGA AAA AGG CAA AGT TGA GGC CCA AGG GAG CAA GAT ACT      8077

CCA TGG                                                          8083

(2) INFORMATION FOR SEQ ID NO: 6:

(i) SEQUENCE CHARACTERISTICS:
        (A) LENGTH: 801
        (B) TYPE: amino acid
        (C) STRANDEDNESS: single
        (D) TOPOLOGY: linear (xi) SEQUENCE DESCRIPTION: SEQ ID NO: 6:

Met Val Val Pro Ala Cys Val Leu Val Phe Cys Val Ala Val
             5                  10                  15

Ala Gly Ala Thr Ser Glu Pro Pro Gly Pro Glu Gln Arg Val Val
            20                  25                  30

Arg Arg Ala Ala Glu Val Pro Gly Pro Glu Pro Ser Gln Gln Glu
            35                  40                  45

Gln Val Ala Phe Gly Ser Gly Asp Thr Val Glu Leu Ser Cys His
            50                  55                  60

Pro Pro Gly Gly Ala Pro Thr Gly Pro Thr Val Trp Ala Lys Asp
            65                  70                  75

Gly Thr Gly Leu Val Ala Ser His Arg Ile Leu Val Gly Pro Gln
            80                  85                  90

Arg Leu Gln Val Leu Asn Ala Ser His Glu Asp Ala Gly Val Tyr
            95                  100                 105

Ser Cys Gln His Arg Leu Thr Arg Arg Val Leu Cys His Phe Ser
            110                 115                 120
```

```
Val Arg Val Thr Asp Ala Pro Ser Ser Gly Asp Asp Glu Asp Gly
            125                 130                 135

Glu Asp Val Ala Glu Asp Thr Gly Ala Pro Tyr Trp Thr Arg Pro
            140                 145                 150

Glu Arg Met Asp Lys Lys Leu Leu Ala Val Pro Ala Ala Asn Thr
            155                 160                 165

Val Arg Phe Arg Cys Pro Ala Ala Gly Asn Pro Thr Pro Ser Ile
            170                 175                 180

Ser Trp Leu Lys Asn Gly Lys Glu Phe Arg Gly Glu His Arg Ile
            185                 190                 195

Gly Gly Ile Lys Leu Arg His Gln Gln Trp Ser Leu Val Met Glu
            200                 205                 210

Ser Val Val Pro Ser Asp Arg Gly Asn Tyr Thr Cys Val Val Glu
            215                 220                 225

Asn Lys Phe Gly Ser Ile Arg Gln Thr Tyr Thr Leu Asp Val Leu
            230                 235                 240

Glu Arg Ser Pro His Arg Pro Ile Leu Gln Ala Gly Leu Pro Ala
            245                 250                 255

Asn Gln Thr Ala Ile Leu Gly Ser Asp Val Glu Phe His Cys Lys
            260                 265                 270

Val Tyr Ser Asp Ala Gln Pro His Ile Gln Trp Leu Lys His Val
            275                 280                 285

Glu Val Asn Gly Ser Lys Val Gly Pro Asp Gly Thr Pro Tyr Val
            290                 295                 300

Thr Val Leu Lys Thr Ala Gly Ala Asn Thr Thr Asp Lys Glu Leu
            305                 310                 315

Glu Val Leu Ser Leu His Asn Val Thr Phe Glu Asp Ala Gly Glu
            320                 325                 330

Tyr Thr Cys Leu Ala Gly Asn Ser Ile Gly Phe Ser His His Ser
            335                 340                 345

Ala Trp Leu Val Val Leu Pro Ala Glu Glu Leu Met Glu Thr
            350                 355                 360

Asp Glu Ala Gly Ser Val Tyr Ala Gly Val Leu Ser Tyr Arg Val
            365                 370                 375

Val Phe Phe Leu Phe Ile Leu Val Val Ala Ala Val Ile Leu Cys
            380                 385                 390

Arg Leu Arg Ser Pro Pro Lys Lys Gly Leu Gly Ser Pro Thr Val
            395                 400                 405

His Lys Val Ser Arg Phe Pro Leu Lys Arg Gln Val Ser Leu Glu
            410                 415                 420

Ser Asn Ser Ser Met Asn Ser Asn Thr Pro Leu Val Arg Ile Ala
            425                 430                 435

Arg Leu Ser Ser Gly Glu Gly Pro Val Leu Ala Asn Val Ser Glu
            440                 445                 450

Leu Glu Leu Pro Ala Asp Pro Lys Trp Glu Leu Ser Arg Thr Arg
            455                 460                 465

Leu Thr Leu Gly Lys Pro Leu Gly Glu Gly Cys Phe Gly Gln Val
            470                 475                 480

Val Met Ala Glu Ala Ile Gly Ile Asp Lys Asp Arg Thr Ala Lys
            485                 490                 495

Pro Val Thr Val Ala Val Lys Met Leu Lys Asp Asp Ala Thr Asp
            500                 505                 510
```

```
Lys Asp Leu Ser Asp Leu Val Ser Glu Met Glu Met Met Lys Met
                515                 520                 525

Ile Gly Lys His Lys Asn Ile Ile Asn Leu Leu Gly Ala Cys Thr
                530                 535                 540

Gln Gly Gly Pro Leu Tyr Val Leu Val Glu Tyr Ala Ala Lys Gly
                545                 550                 555

Asn Leu Arg Glu Phe Leu Arg Ala Arg Arg Pro Pro Gly Met Asp
                560                 565                 570

Tyr Ser Phe Asp Ala Cys Arg Leu Pro Glu Glu Gln Leu Thr Cys
                575                 580                 585

Lys Asp Leu Val Ser Cys Ala Tyr Gln Val Ala Arg Gly Met Glu
                590                 595                 600

Tyr Leu Ala Ser Gln Lys Cys Ile His Arg Asp Leu Ala Ala Arg
                605                 610                 615

Asn Val Leu Val Thr Glu Asp Asn Val Met Lys Ile Ala Asp Phe
                620                 625                 630

Gly Leu Ala Arg Asp Val His Asn Leu Asp Tyr Tyr Lys Lys Thr
                635                 640                 645

Thr Asn Gly Arg Leu Pro Val Lys Trp Met Ala Pro Glu Ala Leu
                650                 655                 660

Phe Asp Arg Val Tyr Thr His Gln Ser Asp Val Trp Ser Phe Gly
                665                 670                 675

Val Leu Leu Trp Glu Ile Phe Thr Pro Gly Gly Pro Ser Pro Tyr
                680                 685                 690

Pro Gly Ile Pro Val Glu Glu Leu Phe Lys Leu Leu Lys Glu Gly
                695                 700                 705

His Arg Met Asp Lys Pro Ala Ser Cys Thr His Asp Leu Tyr Met
                710                 715                 720

Ile Met Arg Glu Cys Trp His Ala Val Pro Ser Gln Arg Pro Thr
                725                 730                 735

Phe Lys Gln Leu Val Glu Asp Leu Asp Arg Ile Leu Thr Val Thr
                740                 745                 750

Ser Thr Asp Glu Tyr Leu Asp Leu Ser Val Pro Phe Glu Gln Tyr
                755                 760                 765

Ser Pro Gly Gly Gln Asp Thr Pro Ser Ser Ser Ser Ser Gly Asp
                770                 775                 780

Asp Ser Val Phe Thr His Asp Leu Leu Pro Pro Gly Pro Pro Ser
                785                 790                 795

Asn Gly Gly Pro Arg Thr
                800
```

(2) INFORMATION FOR SEQ ID NO: 7:

(i) SEQUENCE CHARACTERISTICS:
        (A) LENGTH: 9
        (B) TYPE: nucleic acid
        (C) STRANDEDNESS: double
        (D) TOPOLOGY: linear (xi) SEQUENCE DESCRIPTION: SEQ ID NO: 7:

GGAATTCTC                                                                           9

(2) INFORMATION FOR SEQ ID NO: 8:

(i) SEQUENCE CHARACTERISTICS:
        (A) LENGTH: 6
        (B) TYPE: nucleic acid

```
        (C) STRANDEDNESS: double
        (D) TOPOLOGY: linear (xi) SEQUENCE DESCRIPTION: SEQ ID NO: 8:

GAATTC                                                                  6

(2) INFORMATION FOR SEQ ID NO: 9:

(i) SEQUENCE CHARACTERISTICS:
        (A) LENGTH: 3
        (B) TYPE: amino acid
        (C) STRANDEDNESS: single
        (D) TOPOLOGY: linear (xi) SEQUENCE DESCRIPTION: SEQ ID NO: 9:

Gly Ile Leu
    3

(2) INFORMATION FOR SEQ ID NO: 10:

(i) SEQUENCE CHARACTERISTICS:
        (A) LENGTH: 17
        (B) TYPE: nucleic acid
        (C) STRANDEDNESS: single
        (D) TOPOLOGY: linear (xi) SEQUENCE DESCRIPTION: SEQ ID NO: 10:

CCTGCGTCGT GGAGAAC                                                     17

(2) INFORMATION FOR SEQ ID NO: 11:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 11:

GGACGCGTTG GACTCCAG                                                    18

(2) INFORMATION FOR SEQ ID NO: 12:

(i) SEQUENCE CHARACTERISTICS:
        (A) LENGTH: 32
        (B) TYPE: nucleic acid
        (C) STRANDEDNESS: single
        (D) TOPOLOGY: linear (xi) SEQUENCE DESCRIPTION: SEQ ID NO: 12:

GGCTCCTTAT TGGACTCGCC CGGAGCGAAT GG                                    32

(2) INFORMATION FOR SEQ ID NO: 13:

(i) SEQUENCE CHARACTERISTICS:
        (A) LENGTH: 33
        (B) TYPE: nucleic acid
        (C) STRANDEDNESS: single
        (D) TOPOLOGY: linear (xi) SEQUENCE DESCRIPTION: SEQ ID NO: 13:

CTGGCAGCAC CACCAGCCAC GCAGAGTGAT GGG                                   33

(2) INFORMATION FOR SEQ ID NO: 14:

(i) SEQUENCE CHARACTERISTICS:
        (A) LENGTH: 20
        (B) TYPE: nucleic acid
```

-continued

```
        (C) STRANDEDNESS: single
        (D) TOPOLOGY: linear (xi) SEQUENCE DESCRIPTION: SEQ ID NO: 14:

GCGTTGGCAA TTTAACCGCC                                              20

(2) INFORMATION FOR SEQ ID NO: 15:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 15:

CAGTTTACCC GCTCTGCTAC                                              20

(2) INFORMATION FOR SEQ ID NO: 16:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO: 16:

AGAGGCTATT CGGCTATGAC TG                                           22

(2) INFORMATION FOR SEQ ID NO: 17:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 17:

TTCGTCCAGA TCATCCTGAT C                                            21

(2) INFORMATION FOR SEQ ID NO: 18:

(i) SEQUENCE CHARACTERISTICS:
        (A) LENGTH: 9
        (B) TYPE: nucleic acid
        (C) STRANDEDNESS: double
        (D) TOPOLOGY: linear (xi) SEQUENCE DESCRIPTION: SEQ ID NO: 18:

GGCATCCTC                                                           9
```

ANIMAL MODEL FOR FIBROBLAST GROWTH FACTOR RECEPTOR ASSOCIATED CHONDRODYSPLASIA

FIELD AND BACKGROUND OF THE INVENTION

The present invention relates, in general, to an animal model for chondrodysplasia, and more particularly, to a transgenic mouse model for achondroplasia in which a fibroblast growth factor receptor 3 gene including a G to A point mutation changing Gly to Arg in codon 380 thereof (numbered according to the human sequence) is introduced into the mouse genome.

Achondroplasia is the most common genetic form of osteochondrodysplasia, with an estimated frequency of 1/15000 to 1/77000 births, Achondroplasia is transmitted in an autosomal dominant fashion with complete penetrance, although 80–90% of cases arise from spontaneous mutations (Andersen, 1989, Iannotti, 1994). The clinical features of heterozygous achondroplasia are very consistent among patients, and include proximal shortening of the extremities, midface hypoplasia, narrowing of the spinal column and relative macrocephaly (Rousseau, 1994, Shiang, 1994, Prinos, 1995). Final achondroplasia adult height ranges between 112 to 145 cm.

Histologically, the epiphyseal and growth plate cartilage of achondroplasia patients have a normal appearance (Rimoin, 1970). However, morphometric examinations of such patients revealed that the growth plate is shorter than normal and that the shortening is greater in homozygous than in heterozygous achondroplasia, suggesting a gene dosage effect (Horton, 1988). The intercolumnar matrix of achondroplasia patients is more abundant than normal, and focus of vascularization and transverse tunneling of the cartilage (ingrowth of blood vessels) was observed in some cases. In addition, marked periosteal bone formation was observed (Rimoin, 1970). The underlying mechanism of achondroplasia is believed to be a defect in the maturation of long bones growth plate chondrocytes (Ponseti, 1970, Maynard, 1981, Iannotti, 1994).

Achondroplasia was recently shown to be caused by point mutations in the transmembrane domain of fibroblast growth factor receptor 3 (FGFR3, Shiang, 1994). Virtually all patients show either a G to A or a G to C conversion, changing the codon for Gly 380 to Arg. This guanosine 1138 nucleotide has been described as the most mutable nucleotide to date in the human genome (Bellus, 1995). Other mutations that have been described so far lie within the transmembrane domain (Gly 375 to Cys, Superti-Furga, 1995, Ikegawa, 1995) and within the Ig3-TM linker region (Gly 346 to Glu, Prinos, 1995).

FGFR3 is a high-affinity membrane-spanning receptor for fibroblast growth factors (FGFs). The binding of FGF to the extracellular domain of FGFR3, in the presence of heparan sulfate proteoglycans, induces the dimerization of two receptor molecules, allowing transphosphorylation of tyrosines (and possibly threonine and serine residues) within the activation loop of the intracellular tyrosine kinase domains.

Activation loop phosphorylation greatly enhances the ability of FGFR3 to autophosphrylate as well as to phosphorylate substrates which transmit biological signals into the cell leading to cell proliferation, differentiation, angiogenesis, or embryogenesis (Basilico, 1992, Friesel, 1995, Jaye, 1992, Johnson, 1993).

The role of FGFR3 in the growth plate appears to be one of negative regulation of intrinsic growth rates, since mice that are homozygous for FGFR3 null alleles (e.g., by gene knock-out) show kyphosis, scoliosis, overgrowth of long bones and enlargement of the hypertrophic zone of growth plates (Deng, 1996, Colvin, 1996). This phenotype is consistent with a normal role for FGFR3 in restraining chondrocyte proliferation (upper-hypertrophic cells) and final differentiation (lower-hypertrophic cells) at the growth plates of tubular long bones and at the sutures of the skull.

Mutations in FGFR3 and in other fibroblast growth factor receptor genes can also result in other abnormalities, including skeletal and cranial malformation syndromes (Bonaventure, 1996, Muenke, 1995, Park, 1995, Webster, 1997, Lewanda, 1996). Some of the more frequent mutations of FGFRs associated with craniosynostosis and dwarfism syndromes are listed in Table 1, below.

TABLE 1

Some FGFR mutations associated wth craniosynostosis and dwarfism syndromes

| Mutation | Syndrome |
| --- | --- |
| FGFR 1 | |
| Pro252Arg | Pfeiffer |
| FGFR2 | |
| Tyr105Cys | Crouzon |
| Ser252Trp | Apert |
| Ser252Phe(CG→TT) | Apert |
| Ser252Leu | Normal type crouzon |
| 934CGC→TCT(SP→FS) | Pfeiffer |
| Pro253Arg | Apert |
| Ser267Pro | Crouzon |
| Insertion Gly269 | Crouzon |
| 982insTGG [insG] | Crouzon |
| Cys278Phe | Pfeiffer; Crouzon |
| 1037del9 [delHIQ] | Crouzon |
| Deletion His287-Gln289 | Crouzon |
| Gln289Pro | Crouzon |
| Trp290Gly | Crouzon |
| Trp290Arg | Crouzon |
| Trp290Cys(G→C) | Pfeiffer |
| Trp290Cys(G→T) | Pfeiffer |
| Lys292Glu | Crouzon |
| 1119-3T→G[f] | Pfeiffer |
| 1119-2A→G[f] | Pfeiffer; Apert |
| 1119-1G→C[f] | Pfeiffer |
| Exon III acceptor splice site | Pfeiffer |
| Ala314Ser | Pfeiffer |
| Asp321Ala | Pfeiffer |
| Tyr328Cys | Crouzon |
| Asn331Ile | Crouzon |
| 1190ins6 [insDA] | Crouzon |
| Gly338Arg | Crouzon |
| Gly338Glu | Crouzon |
| Tyr340His | Crouzon |
| Thr341Pro | Pfeiffer |
| Cys342Arg | Pfeiffer; Crouzon; Jackson-Weiss |
| Cys342Ser(G→C) | Pfeiffer; Crouzon |
| Cys342Ser(T→A) | Pfeiffer; Crouzon |
| Cys342Tyr | Pfeiffer; Crouzon |
| Cys342Trp | Crouzon |
| Cys342Phe | Crouzon |
| Ala344Ala(G→A)[f] | Crouzon; unclassified |
| Ala344Pro | Pfeiffer |
| Ala344Gly | Crouzon; Jackson-Weiss |
| Ser347Cys | Crouzon |
| Deletion Gly345-Pro361[a] | Pfeiffer; Crouzon |
| Ser351Cys | Unclassified |
| Ser354Cys | Crouzon |
| 1245del9[delWLT] | Crouzon |
| Val359Phe | Pfeiffer |
| 1263ins6[f] | Pfeiffer |

TABLE 1-continued

Some FGFR mutations associated wth craniosynostosis and dwarfism syndromes

| Mutation | Syndrome |
| --- | --- |
| Ser372Cys | Beare-Stevenson cutis gyrata |
| Tyr375Cys | Beare-Stevenson cutis gyrata |
| Gly384Arg | Unclassified |

| FGFR 3 | |
| --- | --- |
| Arg248Cys | Thanatophoric dysplasia type I |
| Ser249Cys | Thanatophoric dysplasia type I |
| Pro250Arg | Non-syndromic craniosynostosis |
| Gly346Glu | Achondroplasia |
| Gly370Cys | Thanatophoric dysplasia type I |
| Ser371Cys | Thanatophoric dysplasia type I |
| Tyr373Cys | Thanatophoric dysplasia type I |
| Gly375Cys | Achondroplasia |
| Gly 380 to Arg | Achondroplasia |
| Ala391Glu | Crouzon with acantbosis; nigricans |
| Asn540Lys | Hypochondroplasia |
| Lys650Glu | Thanatophoric dysplasia type II |
| Lys650Met | Novel skeletal dysplasia |
| Stop807Gly | Thanatophoric dysplasia type I |
| Stop807Arg | Thanatophoric dysplasia type I |
| Stop807Cys | Thanatophoric dysplasia type I |

Clinical similarities had already suggested that achondroplasia is part of a continuous spectrum of diseases that are all due to mutations in FGFR3 and share a common defect (McKusick, 1973). the underlying defect in these disorders is a disruption of the normal, regulated proliferation and differentiation of chondrocytes, which takes place at the epiphyseal plates of long bones and base of skull during osteogenesis. They are characterized clinically by skeletal deformities and varying degrees of dwarfism apparent before birth, typically with disproportion between the lengths of the trunk and the limbs (Horton, 1993).

On the mild side of the spectrum is hypochondroplasia, a condition associated with moderate, but variable disproportionate shortness of limbs. The trunk is normal and the face is otherwise unremarkable. The head may be normal or slightly enlarged with mild frontal bossing. The hands and feet tend to be broad and stubby. Radiographically, changes typically seen in achondroplasia are present in very mild degree. Mild shortening of the long bones with slight metaphyseal flaring are observed. The femoral necks are short and broad. The fibulae are disproportionately long, and the ilia are short and square. Shortening of the lumbar pedicles is mild to moderate and the interpediculate distance from L1 to L5 may narrow slightly.

Histologically, the growth plates of hypochondroplasia patients show no consistent microscopic abnormalities (Sillence, 1979). Some patients with hypochondroplasia have been shown to be linked to chromosome 4p, the locus where FGFR3 resides, and to have a mutation within the intracellular kinase domain of the receptor (Asn 540 to Lys, Bellus, 1995). However, other patients were shown not to be linked to chromosome 4p, and thus hypochondroplasia may be determined by mutations in genes other than FGFR3 (Stoilov, 1995).

On the lethal side of the spectrum is thanatophoric dysplasia, a condition that clinically resembles the lethal phenotype of homozygous achondroplasia patients (Stanescu, 1990). Thanatophoric dwarfs exhibit extreme shortening of the limbs, long narrow trunk, markedly narrow thorax, large abdomen, redundancy of skin folds of arms and legs, large head, extreme platyspondyly, and marked midface hypoplasia (Horton, 1993). The severe thoracic and abdominal malformations ultimately cause death through respiratory distress (Shah, 1973, Wynne-Davies, 1985, Webster, 1997). In the few individuals who have survived for several years with medical intervention, there are also deficiencies in central nervous system development (MacDonald, 1989). Consistent with the tissues affected in thanatophoric dysplasia, FGFR3 (c isoform) is primarily expressed in the central nervous system, in prebone cartilage rudiments and at the cartilaginous growth plates of bones (Peters, 1992, Peters, 1993).

Radiologically, features similar to those of homozygous achondroplasia are recognized in thanatophoric dysplasia patients (Langer, 1969). Although the skull is large (large calvariae) with frontal bossing, the facial bones and cranial base are small. The ribs and the scapulae are short. Platyspondyly is severe with wide intervertebral disc spacing, the iliac bones are short and squared, the acetabular roofs are flat, the sacrosciatic notches are short, the femora are shaped like telephone receivers, and the tubular bones are short, bowed, and cupped at their ends (Gorlin, 1997, Horton, 1993). Newborns with thanatophoric dysplasia have been placed in different phenotypic subgroups (Spranger, 1992). The classic form (type I) is characterized by curved short femurs with or without cloverleaf skull, whereas patients of the type II subgroup have slightly longer and straighter femurs and invariably fusion of all cranial sutures, resulting in cloverleaf skull (Young, 1973).

Histologically, in thanatophoric dysplasia there is a generalized disorganization of endochondral ossification at the bone growth plate (Rimoin, 1974), less proliferative and hypertrophic chondrocytes (Horton, 1993, Delezoide, 1997) and discrete areas of short but relatively normal growth plate architecture and fibrotic lesions are observed. These lesions seem to be associated with epiphyseal vascular canals near the growth plate. "Ossification tufts" which are mineralization extensions of the subchondral bone, are also characteristics of the disorder (Horton, 1988).

Thanatophoric dysplasia type I dwarfism has been shown to be caused by mutations at six different sites within FGFR3, but all reported cases of thanatophoric dysplasia type II result from the same Lys 650 to Glu point mutation in the tyrosine kinase domain of FGFR3 (Rousseau, 1995, Tavormina, 1995, Tavormina, 1995, Rousseau, 1996). Phosphorylation of the two activation loop residues corresponding to Tyr 647 and Tyr 648 of FGFR3 has been shown to be essential for activation of the tyrosine kinase activity and the biological activity of the related receptor FGFR1 (Mohammadi, 1996), suggesting that they would also be major sites of activating autophosphorylation in FGFR3. The spectrum of severity observed in patients with FGFR3 mutations is directly related to the degree of receptor activation (Naski, 1996, Webster, 1996).

There is thus a widely recognized need for, and it would be highly advantageous to have, an animal model for chondrodysplasia and in particular a mouse model for achondroplasia in which a mutated FGFR3 gene which causes gain of function is introduced into the mouse genome. Such a model can be exploited to gain better understanding of the disease and as an experimental model with which experimental therapy to chondrodysplasias, such as achondroplasia, can be exercised.

SUMMARY OF THE INVENTION

To test whether the human Gly 380 to Arg FGFR3 can cause micromelia in mice, as can be seen for human achondroplasia patients, a transgenic mice expressing the mutated human FGFR3 gene under the transcriptional control of the endogenic FGFR3 promoter was generated. In addition, transgenic mice having the mouse mutated cDNA (Gly 374 to Arg) were also generated to confirm the speculation that both mutated genes cause the same skeletal abnormalities.

Results presented here suggest that the molecular basis of achondroplasia is enhanced and prolonged post translational signal transduction through activated FGFR3, which is predicted to result in abnormal growth plate proliferation and final differentiation. It seems as if there is a delay in post-translational down regulation of FGFR3 in hypertrophic chondrocytes of mutant FGFR3 transgenic mice, with no alteration in transcriptional regulation.

According to one aspect of the present invention there is provided a genetically modified animal comprising a genetically modified fibroblast growth factor receptor gene integrated in at least one locus in its genome, the genetically modified fibroblast growth factor receptor gene encodes a modified fibroblast growth factor receptor protein, that when expressed results in an integral membrane protein having a gain of function.

According to another aspect of the present invention there is provided a transgenic animal model for chondrodysplasia expressing a modified fibroblast growth factor receptor protein from a transgenic construct including a modified fibroblast growth factor receptor gene, the protein being an integral membrane protein having a gain of function.

According to yet another aspect of the present invention there is provided a transgenic animal model for expression directed by a fibroblast growth factor receptor promoter sequence expressing a reporter gene from a transgenic construct including the fibroblast growth factor receptor promoter sequence.

According to further features in preferred embodiments of the invention described below, the modified fibroblast growth factor receptor protein causes a chondrodysplasia in the animal when expressed.

According to still further features in the described preferred embodiments the modified fibroblast growth factor receptor protein causes achondroplasia in the animal when expressed.

According to still further features in the described preferred embodiments the genetically modified fibroblast growth factor receptor gene is a transgene.

According to still further features in the described preferred embodiments the transgene is in a hetero- or homozygous form.

According to still further features in the described preferred embodiments, when expressed, the genetically modified fibroblast growth factor receptor gene is dominant-like over an equivalent native fibroblast growth factor receptor gene of the animal.

According to still further features in the described preferred embodiments the animal is null for an equivalent endogenous fibroblast growth factor receptor gene According to still further features in the described preferred embodiments the animal includes an active equivalent endogenous is fibroblast growth factor receptor gene.

According to still further features in the described preferred embodiments the genetically modified fibroblast growth factor receptor gene is expressed under a control of a promoter.

According to still further features in the described preferred embodiments the promoter is derived from an equivalent endogenous fibroblast growth factor receptor gene.

According to still further features in the described preferred embodiments the genetically modified fibroblast growth factor receptor gene includes at least one intron or a part thereof.

According to still further features in the described preferred embodiments the genetically modified fibroblast growth factor receptor gene includes at least two exons fused adjacent one another as in complementary DNA.

According to still further features in the described preferred embodiments the animal and the genetically modified fibroblast growth factor receptor gene are both of a single species.

According to still further features in the described preferred embodiments the animal and the genetically modified fibroblast growth factor receptor gene are of different species.

According to still further features in the described preferred embodiments the genetically modified fibroblast growth factor receptor gene is a genetically modified fibroblast growth factor receptor 3 gene.

According to still further features in the described preferred embodiments the genetically modified fibroblast growth factor receptor gene includes a point mutation.

According to still further features in the described preferred embodiments the genetically modified fibroblast growth factor receptor 3 gene includes a point mutation.

According to still further features in the described preferred embodiments the point mutation results in changing a Gly to Arg in codon 380, or its equivalent (homologous) codon (e.g., codon 374 in mouse FGFR3 gene), of the genetically modified fibroblast growth factor receptor 3 gene.

According to still further features in the described preferred embodiments the animal is a mouse.

According to still further features in the described preferred embodiments the gain of function is ligand independent signal transduction.

The present invention successfully addresses the shortcomings of the presently known configurations by providing a transgenic animal model of chondrodysplasias, thanatophoric dysplasia, achondroplasia or hypochondroplasia, in particular. The present invention provides the first transgenic gain of function animal model for any fibroblast growth factor receptor gene.

BRIEF DESCRIPTION OF THE DRAWINGS

The file of this patent contains at least one drawing executed in color. Copies of this patent with color drawings are provided to the Patent and Trademark Office with payment of the necessary fee. The invention herein described, by way of example only, with reference to the accompanying drawings, wherein:

FIGS. 5a–f demonstrate gross phenotype of newborn transgenic and non-transgenic mice. FIGS. 5a, 5c and 5e show the upper part of the body and FIGS. 5b, 5d and 5f show the lower part thereof. The mouse to the right (5e and 5f) is normal. The mouse in the center (5c and d) is heterozygote for the human mutated FGFR3 transgene. The mouse to the left (5a and 5b) is homozygous for that transgene.

FIGS. 9a–f demonstrate retardation in endochondral ossification. FIGS. 9a–d show histological analysis of proximal tibia and fingers structures of 15-days-old transgenic mice are shown. FIGS. 9a and 9b represent homozygous transgenic embryos. FIGS. 9c and 9d represent normal embryos. Chondrocytes maturation and proliferation is markedly abnormal in the transgenic embryos. While hypertrophic cells are present in the growth plate of normal tibia, no hypertrophic cells can be seen in mice homozygous for the transgene. In addition, less cells are evident. FIGS. 9e and 9f reveal that achondroplasia transgenic mice exhibit delayed chondrocyte differentiation. As shown here for the proximal femur secondary ossification center of a 2-months-old transgenic mice (9f), as compared to a 2-months-old normal control (9e), replacement of cartilage by bone and vascular invasion have not yet taken place. This delay in chondrocyte proliferation and differentiation leads to a decrease in growth plate thickness and as a result a decrease in resource for bone formation.

DESCRIPTION OF THE PREFERRED EMBODIMENTS

Figure 1A:
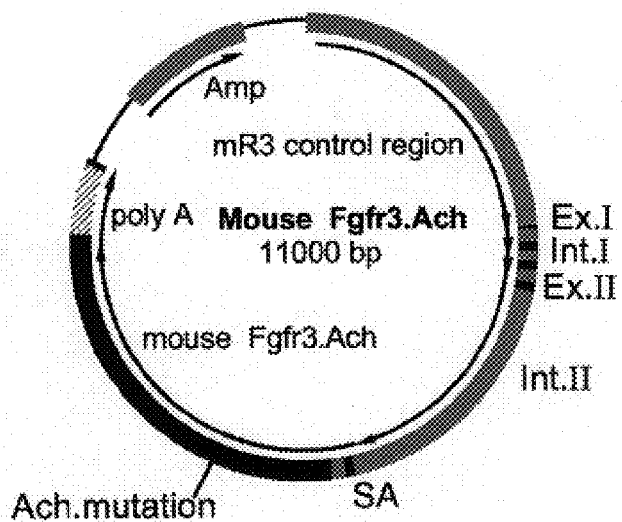
FIGS. 1a–c show the construction of the three transgenes employed herein. (1a) Map of the mutated mouse FGFR3 transgene construct. This construct was designed to encompass essential regulatory elements, including chondrocyte-specific activators in the promoter region and exon 1 with the extenuation of intron 1 and part of exon 2. (1b) Map of the mutated human FGFR3 transgene construct. This construct contains only the above promoter region and exon 1 to prove that intron 1 does not have any role in FGFR3 expression. (1c) Map of the mouse FGFR3 promoter/β-galactosidase transgene construct. This construct includes a truncated FGFR3 promoter (−282 to +1) exon 1 and intron 1. All the above mentioned regulatory elements are present within this region. SA—splice acceptor, Ex—exon, int—intron. The mutation is the Gly 380 to Arg achondroplasia mutation.

The present invention is of an animal model for chondrodysplasia which can be used to investigate the nature of chondrodysplasias at the molecular, biochemical, histological and skeletal level and which can be further used as a tool for screening, development and evaluation of drugs with a potential of relieving or abolishing chondrodysplasia syndromes and/or symptoms. In particular, the present invention is of a mouse model for achondroplasia, in which a G to A point mutation is introduced into the human or mouse FGFR3 gene, changing Gly to Arg in codon 380 or 374 thereof, respectively, which can be used to investigate the nature of achondroplasia at the molecular, biochemical, histological and skeletal level, and which can be further used as a tool for screening, development and evaluation of drugs with a potential of relieving or abolishing achondroplasia syndromes and symptoms.

The principles and operation of an animal model according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

While reducing the present invention to practice, micromelia was found in transgenic heterozygous and homozygous mice including at least one genetically modified (mutated) human or mouse FGFR3 transgene in varying degrees that appear to correlate with the dose and level of expression of the transgene. In addition, the heterogeneity in severity of phenotypes of heterozygous human achondroplasia patients and of transgenic mice probably reflects, to some extent, the absolute degree of FGFR3 activation, but additionally suggests that other genes are involved that modulate the dominant (in human) or dominant-like (in transgenic mice) effects of the mutated FGFR3. Different genetic background resulting in variable local gene expression levels of FGFs and downstream effectors might ultimately determine the severity of particular individuals (Mason, 1994).

The salient features of the human achondroplasia disorder are listed in the Background section above. Comparison of the abnormalities in the skeletal system of mutated FGFR3 transgenic mice, as listed in the Experimental Results section hereinbelow, to those observed in human patients clearly shows that they share remarkable similarity, regardless whether the mutated transgene is human or mouse derived. Furthermore, it is important to note that high expression of the mutated transgene (high copy number, homozygocity) typically results in death soon after birth due to respiratory insufficiency, similar to their homozygous human counterparts. In both cases, the short, capped ribs are most likely the cause of respiratory failure and death.

It is most important to emphasize that in both cases, mice models and human patients, the main phenotype is disproportionate dwarfism include shortening of proximal long bones relative to distal bones. Furthermore, the trunk length is normal and only in severe homozygous state it's slightly shorter. Kyphosis at the base of the head, narrowing of the trunk and bowing of long bones which are also clear definitive phenotypes of achondroplasia were discovered in the mice models of the present invention.

The biological basis of the human most common chondrodisplasias (i.e., thanatophoric dysplasia, achondroplasia and hypochondroplasia) seems to involve a defect in endochondral ossification, decrease of chondrocyte proliferation and differentiation to hypertrophic chondrocytes, combined with fibrosis and abnormal ossification.

Delay in endochondral growth, in conjunction with the apparently undisturbed periosteal bone formation, could explain the characteristic short, squat shape of the tubular bones. This phenomenon is reflected in the cupping at the growth zone as demonstrated in the rib or long bones clearance.

The data presented herein are consistent with the histological irregularities observed in human achondroplasia patients and homozygous newborns. The growth plate is shorter than normal especially in older mice and shortening is greater in homozygotes than in heterozygotes, extracellular matrix is abundant particularly in older mice, and vascular invasion occurs irregularly across the growth plate. Mineralized extensions of the subchondral bone might also be found in few foci. Severe homozygous newborn distal femur growth plates have much greater circumference, there is a definite shortage of chondrocytes which are irregularly arranged with a failure of columnization, adequate bars of calcified hypertrophic cells fail to form, and the ossification is sparse and irregular and may extend into the growth plate. Periosteal ossification is excessive and vascularization are also dispersed within the lower-hypertrophic zone. The following observations indicate that the rate of endochondral ossification is defective in the mutant transgenic mice according to the present invention.

As early as sixteen days of prenatal development one can detect inhibition in endochondral ossification. The tibial growth plate of a sixteen-days-old embryo is clearly diminished in size, and less cells are present, in each column suggesting a reduced cell proliferation rate. In addition, at this stage no lower hypertrophic cells are observed in the mutant mice growth plate, suggesting a delay in terminal differentiation.

Furthermore, in 2-months-old mutant transgenic mice a second ossification center within the proximal femur epiphysis is not yet detected, while in the control mice ossified bone already exists. Once more this data suggest a delay in terminal differentiation. Enhancing the expression of mutant FGFR3 (homozygous mice), creates many more stable dimers that may mimic the thanatophoric dysplasia phenotype.

The observation that less hypertrophic chondrocytes expressed collagen type X in transgenic growth plate suggests again that activation of the receptor interferes with terminal differentiation. This hypothesis is supported by previous data which demonstrate that application of FGF2 or FGF9 to rabbit chondrocytes or mice organ cultures prevented terminal differentiation and calcification accordingly (Kato, 1990)

Chondrocytes in the proliferative and upper-hypertrophic regions of transgenic mice growth plates stained positively for proliferating cell nuclear antigen (PCNA), a marker for dividing cells. Less cells were shown to be positive for PCNA by immunohistochemical staining of mutant mice growth plate sections. This suggests that activated FGFR3 may restrain cell proliferation.

Interestingly, blood vessels invasion into the growth plate which was observed in human is also found in the transgenic mice according to the present invention. At the moment no definite explanation is available. One possible mechanism might be auto induction of specific FGF ligands which in turn encourage ingrowth of blood vessels within the growth plate.

Thus, according to one aspect of the present invention, there is provided a genetically modified animal comprising a genetically modified fibroblast growth factor receptor gene integrated in at least one locus in its genome. The genetically modified fibroblast growth factor receptor gene encodes a modified fibroblast growth factor receptor protein, that when expressed results in an integral membrane protein having a gain of function. According to a preferred embodiment of the present invention, the modified fibroblast growth factor receptor protein causes a chondrodysplasia in the animal, thanatophoric dysplasia, achondroplasia or hypochondroplasia, in particular, when expressed.

According to another aspect of the present invention, there is provided a transgenic animal model for chondrodysplasia, thanatophoric dysplasia, achondroplasia or hypochondroplasia, in particular. The animal expresses a modified fibroblast growth factor receptor protein from a transgenic construct including a modified fibroblast growth factor receptor gene. The protein is an integral membrane protein having a gain of function.

According to another aspect of the present invention, there is provided a transgenic animal model for expression directed by a fibroblast growth factor receptor promoter sequence expressing a reporter gene from a transgenic construct including the fibroblast growth factor receptor promoter sequence.

As used herein in the specification and in the claims section below, the term "reporter gene" refers to a gene encoding a protein detectable by being capable of directing a fluorescent, chemiluminiscent or color reaction. β-galactosidase and luciferase are commonly used reporter genes.

As used herein in the specification and in the claims section below, the term "animal" refers to all mammals and their fetuses, but human, including, but not limited to, rodents such as mouse rats and guinea pigs, monkeys such as gorilla, chimpanzee, gibbon, rhesus, apes in particular, pigs, sheep, cattle, etc. The list provided is not limiting. However, the listed animals are frequently used to provide experimental models for human diseases and therefore particular knowledge has accumulated, rendering these animals presently advantageous over other animals, less frequently employed in scientific research. The term is therefore equivalent to the phrase "non-human mammal".

As used herein in the specification and in the claims section below, the term "chondrodysplasia" refers to cartilaginous and/or cartilage derived bone defects.

As used herein in the specification and in the claims section below, the term "achondroplasia" refers to cartilaginous and/or bone defect resulting in dwarfism.

As used herein in the specification and in the claims section below, the term "transgenic" refers to a procedure in which a nucleic acid sequence (typically including a gene and expression control elements and called a transgene) is integrated into at least one locus of a genome of an animal, such that it is transmittable along generations.

As used herein in the specification and in the claims section below, the term "gain of function" relates to any situation in which altered quantitative or qualitative functionality or time altered functionality (e.g., delayed, early) is experienced, except for complete loss of functionality.

As used herein in the specification and in the claims section below, the term "construct" refers to any vehicle suitable for transducing cells, including, but not limited to, viruses (e.g., bacoluvirus), phages, plasmids, phagemids, bacmids, cosmids, artificial chromosomes and the like.

As used herein in the specification and in the claims section below, the term "transduced" refers to the result of a process of inserting nucleic acids into cells or animals. The insertion may, for example, be effected by transformation, viral infection, injection, transfection, gene bombardment, electroporation or any other means effective in introducing nucleic acids into cells. Following transduction the nucleic acid is integrated in all or part, to the cell's genome.

As used herein in the specification and in the claims section below, the term "genetically modified" refers to a sequence alteration which results in altered expression as compared with a wild type equivalent sequence.

The sequence alteration may be natural or man-made. Preferably it is a mutation in a structural part of a gene, however, control sequence (e.g., promoter, enhancer) mutations are not excluded. The alteration can be insertion, deletion and/or substitution of one or more nucleotides in one or more locations.

As used herein in the specification and in the claims section below, the term "gene" refers to a nucleic acid sequence from which a protein can be expressed. Thus, a gene can include, for example, a complementary DNA sequence, a genomic DNA sequence or a mixed sequence of genomic DNA and cDNA. Additional sequences can be included, such as, but not limited to, polylinkers, selection sequences, reporter sequences and genetically modified sequences, such as, but not limited to sequence alterations, etc. The introns of the gene, can for example be modified, e.g., shortened, missing etc. However, the term gene as used herein further relates also to the control sequences flanking or residing within the nucleic acid sequence from which a protein can be expressed, in particular upstream (5') control sequences.

As used herein in the specification and in the claims section below, the term "fibroblast growth factor receptor" refers to a receptor which binds fibroblast growth factor, including, but not limited to, fibroblast growth factor receptor 1, fibroblast growth factor receptor 2, fibroblast growth factor receptor 3 and fibroblast growth factor receptor 4, the sequences of all of which from various species are published, see, for example Dionne, 1990, Wuchner, 1997 and Partanen, 1991.

According to a preferred embodiment of the present invention the genetically modified fibroblast growth factor receptor gene is a transgene present in the animal's genome in a single locus in one or more copies or in a plurality of loci. Each such loci including a transgene can independently be in a heterozygous or homozygous form.

In most cases according to the present invention, when expressed, the genetically modified fibroblast growth factor receptor gene is dominant-like over an equivalent (homologous) native fibroblast growth factor receptor gene of the animal. Dominance is typically attributed to one allele vs. another in a single locus. Here, however, the alleles, e.g., a transgene and its equivalent endogenous sequence, are of different loci (locations in the genome). Therefore, the genetic term "dominant" fails to apply. Yet, dominance results due to allele expression (or lack of expression). As such, it is indifferent to the loci from which expression takes place. The term "dominant-like" thus refers to an artificial situation in which a transgene is expressed from one locus whereas its equivalent endogenous gene is expressed from a second locus, wherein if the transgene would have been expressed from the second locus as well, it would have been dominant over the endogenous gene.

According to a preferred embodiment of the present invention the animal is null for its equivalent endogenous fibroblast growth factor receptor gene. Null animals derived by gene knock-out are know for FGFR1–3. One such animal, null for its endogenous FGFR3, and expressing a genetically modified FGFR3 transgene is demonstrated in the Examples section hereinbelow. Alternatively, the animal includes an active (expressed) equivalent endogenous fibroblast growth factor receptor gene.

As already mentioned, according to a preferred embodiment of the present invention, the genetically modified fibroblast growth factor receptor gene is expressed under a control of a promoter.

As used herein in the specification and in the claims section below, the term "promoter" refers to cis acting expression control sequences which are typically present upstream to protein encoding genes. However, such control sequences may also be present in throughout and in the 5' region of the gene itself, either in introns or exons. According to a preferred embodiment of the present invention, the promoter is derived from an equivalent endogenous fibroblast growth factor receptor gene, such that the expression pattern of the genetically modified gene would mimic that of the endogenous gene. However, constitutive promoters, e.g., viral or housekeeping gene promoters, or tissue specific promoters can alternatively be employed.

Two examples are shown in the examples section below in which human Gly 380 to Arg FGFR3 cDNA or mouse Gly 374 to Arg FGFR3 cDNA served as the genetically modified fibroblast growth factor receptor gene to form genetically modified mice. Thus, according to one embodiment of the present invention the animal and the genetically modified fibroblast growth factor receptor gene are both of a single species. In this way, the animal better suits as a model for a genetic disease associated with the genetic modification. Yet according to another embodiment of the present invention the animal and the genetically modified fibroblast growth factor receptor gene are of different species.

To serve as a model for achondroplasia, which, in human beings, is the result of a point mutation in the transmembrane domain of the fibroblast growth factor receptor 3, the genetically modified fibroblast growth factor receptor gene is preferably a fibroblast growth factor receptor 3 gene similarly modified to include the point mutation. Thus, it preferably includes a point mutation, the result of which is a change of Gly to Arg at codon 380 (of the human FGFR3 gene), or its equivalent (homologous) codon in other species, e.g., codon 374 in the mouse gene.

The present invention thus provides a transgenic animal model of chondrodysplasias, achondroplasia in particular. The present invention provides the first transgenic gain of function animal model for any fibroblast growth factor receptor gene. It can be used as a tool for testing novel therapies designed to combat chondrodysplasias such as achondroplasia and further as a means of developing genetically dwarf or miniaturized animals which will be useful as pets and for research.

Each of the various embodiments and aspects of the present invention as delineated hereinabove and as claimed in the claims section below finds experimental support in the Examples section that follows.

EXAMPLES

Reference is now made to the following examples, which together with the above descriptions, illustrate the invention in a non limiting fashion.

Materials and Experimental Methods

Targeting vectors: To generate a human mutant FGFR3 transgenic mice, a 3.5 kb human Gly 380 to Arg FGFR3 cDNA fragment encoding the c isoform of FGFR3 was inserted downstream of a 2.456 kb segment of the mouse FGFR3 promoter region and 1st exon (nucleotides −2293 to +163, FIG. 1b, SEQ ID NOs:1–3). The targeting vector was partially sequenced to confirm the mutated site at amino acid 380 and the introduction of an EcoRI site next to it by changing a GGCATCCTC nucleotide stretch (SEQ ID NO:18) to a GGAATTCTC nucleotide stretch (SEQ ID NO:7). The sequence GAATTC (SEQ ID NO:8) is an EcoRt site and the corresponding coded amino acids remain GIL (SEQ ID NO:9). Therefore, the expressed protein is not mutated due to the introduction of the EcoRI site.

Figure 1B:
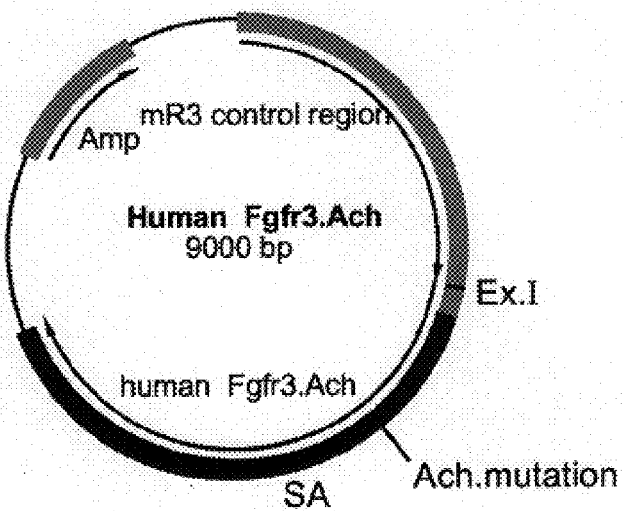

To generate the mouse mutant FGFR3 transgenic mice the mouse Gly 374 to Arg FGFR3 cDNA (codon 374 in mouse FGFR3 is homologous or equivalent to codon 380 in human FGFR3) was ligated to the same mouse promoter described above which also included the first intron, the second exon and 1.66 kb of the 2nd intron (5 kb, nucleotides −2293 to 2699), between a splicing acceptor sequence and the bovine growth hormone polyadenylation signal (FIG. 1a, SEQ ID NOS:4–6). The splice acceptor was included to create an artificial exon and thus circumvent alternative splicing. The polyadenylation/termination signals were added to increase expression efficiency.

Figure 1C:
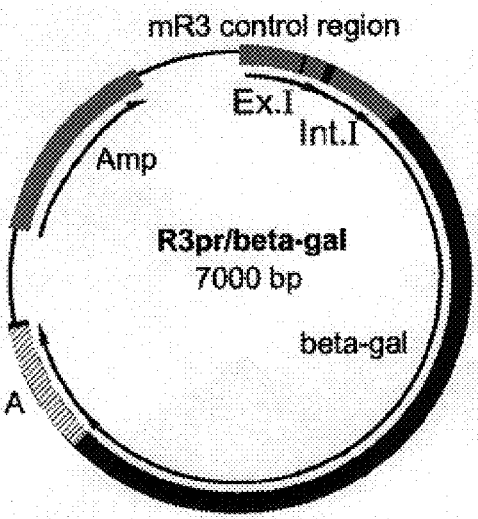
Figure 2A:
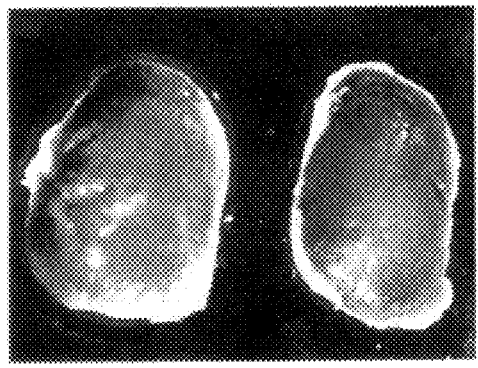
FIGS. 2a–f demonstrate β-galactosidase expression in different issues of a mouse FGFR3 promoter/β-galactosidase transgenic mice. (2a) rain, (2b) lung, (2c) liver, (2d) heart, (2e) ear (for cartilage) and (2f) sternum (also for cartilage). The β-galactosidase gene was not expressed in the transgenic mice heart.
Figure 2B:
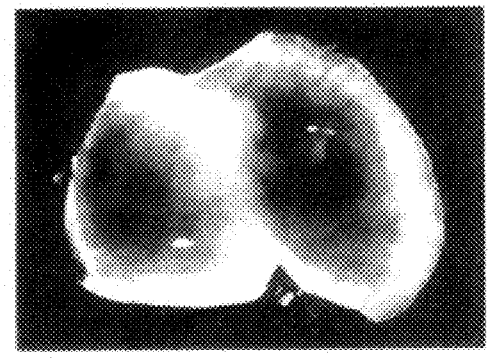
Figure 2C:
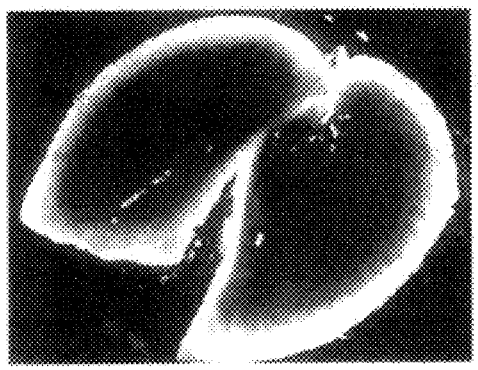
Figure 2D:
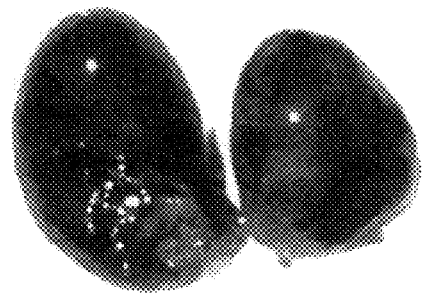
Figure 2E:
Figure 2F:
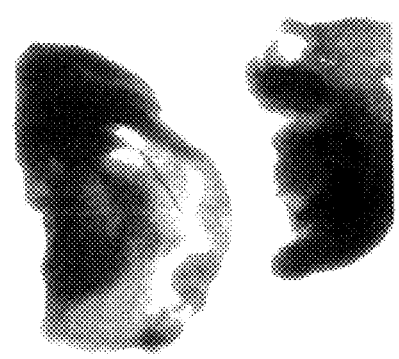

To generate the mouse expressing a β-galactosidase reporter transgene under the control of the mouse FGFR3 promoter a β-galactosidase reporter gene was ligated to a similar, yet shorter, control region which includes only the sites that were proven to be necessary for transcriptional regulation (nucleotides −282 to +570, FIG. 1c).

Generation of Transgenic Mice: The assembled transgenes were then microinjected into a pronuclei of CB6F1 fertilized eggs, and resultant FGFR3 transgenic mice were identified by PCR amplification and Southern blot analysis. For the human transgene (FIG. 1b) genomic tail DNA samples were digested with EcoRI or HindIII, and then probed with an EcoRI/EcoRI 1.1 Kb fragment derived from the human FGFR3 cDNA sequence. For PCR analysis, the human FGFR3 allele was detected using a sense oligonucleotide (5'-CCTGCGTCGTGGAGAAC-3', SEQ ID NO:10) and a antisense oligonucleotide (5'-GGACGCGTTGGACTCCAG-3', SEQ ID NO:11). This primer pair is specific to the human sequence and it amplifies a 610 bp fragment thereof. The mouse exogenic FGFR3 allele was detected using a sense oligonucleotide (5'-GGCTCCTTATTGGACTCGCC CGGAGCGAATGG-3', SEQ ID NO:12) and an antisense oligonucleotide (5'-CTGGCAGCACCACCAGCCACGCAGAGTGATGGG-3', SEQ ID NO:13). This primer pair specifically amplifies a 628 bp fragment of the mouse . The β-galactosidase gene can be detected by a sense primer (5'-GCGTTGGCAATTTAACCGCC-3', SEQ ID NO:14) and an antisense primer (5'-CAGTTTACCCGCTCTGCTAC-3', SEQ ID NO: 15). This primer pair amplifies a 429 bp fragment of the β-galactosidase gene. The PGKneo gene (included within the FGFR3 site of knockout mice, Deng, 1996) was detected using a sense oligonucleotide (5'-AGAGGCTATTCGGCTATGACTG-3', SEQ ID NO:16) and the antisense oligonucleotide (5'-TTCGTCCAGAT CATCCTGATC-3', SEQ ID NO:17), and was shown to amplify a 480 bp fragment thereof Transgene heterozygous mice were mated to produce transgene homozygous offspring. Eight clones showed the expected human transgene, two clones were recovered having the mouse exogenic transgene and nine clones had the β-galactosidase gene.

Western Blot Analysis: All protein extraction procedures were performed at 4° C. Brain and cartilage samples from control and transgenic mice were crashed under liquid nitrogen and homogenized in ice-cold buffer A (10 mM Hepes pH 7.9, 1.5 mM MgCl$_2$, 10 mM KCl, 0.5 mM DTT, 0.5 mM PMSF). Subsequently, centrifugation at 5000 cpm for 15 minutes was performed and protein extracts were recovered. The protein extracts were eluted by boiling in sample buffer (62.5 mM Tris-HCl pH 6.9, 2 mM EDTA, 3% SDS, 3.75% glycerol, and 180 mM, β-mercaptoethanol) for 5 minutes. Western blotting was performed using the enhanced chemiluminescence Western blotting reagents (Amersham Corp., Arlington Heights, Ill.) according to the conditions recommended by the supplier. Briefly, samples, 100 ag/lane were analyzed by 10% SDS-PAGE followed by electrophoretic transfer of the size separated proteins to nitrocellulose filters. The filters were first blocked with TBST (20 mM Tris, pH 7.6, 134 mM NaCl, 0.1% Tween-20) containing 5% Carnation nonfat dry milk for 2 hours and then incubated with the relevant polyclonal antibodies for 6 hours at 4° C. After three sequential washes in TBST, 15 minutes each, the filters were incubated with anti-rabbit peroxidase-conjugated secondary antibody (1:20,000 in TBST) for 1 hour at room temperature and then washed again as described above. Protein bands were detected by the enhanced chemiluminescence reaction. To confirm that equal amounts of protein were loaded in each lane the blots were stained with Ponso after the transfer.

Differential staining of cartilage and bone by alcian blue and alizarin red: Staining of cartilage and bone was done according to Inouye's protocol (Inouye, 1976) with some modification. Briefly, the samples were fixed in 95% ethanol for 1–2 days. Skin and viscera were removed. Then the samples were stained for 3–4 days by working solution containing 0.3 % alcian blue 8GS in 70% ethanol (1 volume); 0.1% alizarin red S in 95% ethanol (1 volume); acetic acid (1 volume); 70% ethanol (17 volumes). Skeletons were cleared in 1% KOH and glycerol, and stored in 100% glycerin.

Immunohistochemistry: Bone fragments were fixed with 4% paraformaldehde and then embedded in paraffin blocks. A polyclonal antibody raised against the C-terminal end of human FGFR3 was purchased from Sigma. After a 1 hour incubation of the sections with the specific antibody at room temperature (dilution 1:20) specific detection was achieved by peroxidase detection (not shown). Serial sections were counterstained with methyl green and negative controls were obtained by omitting the specific antibody. Higher antibody dilutions (1:50, 1:100 and 1:200) were tested on both control and FGFR3 transgenic mice sections. No signal was detected when dilution exceeded 1:50. A polyclonal antibody raised against Collagen type X was kindly provided by Dr. W. A. Horton. A polyclonal antibody raised against Collagen type II was purchased from Southern Biotech. Anti-proliferating cell nuclear antigen (PCNA) antibody was purchased from Signet. Detection was carried out essentially as recommended by the manufactures.

Immunofluorescence: The antibodies used in these experiments included a rabbit anti-mouse collagen X antibody (dilution 1:100), generously provided by Dr. W. A. Horton of the Department of Molecular and Medical genetics, Oregon Health Sciences University, Oreg. Polyclonal antibodies against collagen type II (dilution 1:200) and FGFR3 (dilution 1:200) were obtained from Southern Biotech and Sigma, respectively. The fluorescein-conjugated secondary antibodies (dilution 1:100) and the normal goat serum were purchased from Boehringer Mannheim Biochemicals (Indianapolis, Ind.). For immunofluorescence analysis 6 μm paraffin embedded sections of 1-day-old, 8-days-old and 70-days-old control and FGFR3 transgenic mice were used. The samples were preincubated with bovine hyaluronidase in PBS (1 mg/ml) for 45 minutes at 37° C. All subsequent incubations were performed at room temperature with PBS containing 0.05% saponin, 0.1% BSA, and 5% normal goat serum (NGS). The samples were incubated in PBS-saponin-BSA-NGS for 30 minutes to block non-specific binding, and then for 2 hours with the primary antibody. The samples were washed in PBS-saponin-BSA and incubated with a secondary antibody for 1 hours in the dark. After washing in PBS, the samples were mounted with FluorSave fluorescent mounting media (Calbiochem-Novabiochem Corp., La Jolla, Calif.). Samples were examined with a scanning laser confocal microscope with a krypton/argon laser using an optical slice thickness of 1–2 μm.

Clearance: For visualization of whole skeletons, mice were dissected free of skin, viscera and adipose tissue and fixed in 95% ethanol followed by acetone. Bone and cartilage were stained with 0.1% alizarin red S/0.3% alcian blue in 70% ethanol followed by clearing of tissues in potassium hydroxide in glycerol as described (McLeod, 1980).

Experimental Results

Generation and analysis of FGFR3-promoter-β-galactosidase transgenic mice: A construct containing a part of the promoter region and exon 1 and intron 1 of mouse FGFR3 (nucleotides −282 to +570) was ligated to a β-galactosidase reporter gene (FIG. 1c). The rational was to include chondrocyte-specific cis-acting regulatory elements which are located in the first exon and in the 160 bp of the promoter region adjacent the first exon. For transgenization the latter construct was microinjected into the pronuclear of mouse oocytes. Nine founders were detected and propagated and two lines were used for testing for β-galactosidase activity.

As shown in FIGS. 2a–f, X-gal staining revealed high expression of the reporter gene in brain, cartilage (sternum and ear), and liver tissues. Slightly lower expression was observed in lungs and no expression was detected in the heart of one-month-old mice. In newborns, higher expression was observed in the lungs and less in the liver (data not shown). The above results correlate to in vivo FGFR3 expression and hence it was concluded that the mouse FGFR3 promoter region employed is functional as expected therefrom in transgenic mice.

FGFR3 Transgenic Mice: Encouraged by the above results, human and mouse FGFR3 cDNAs containing the Gly 380 to Arg and Gly 374 to Arg mutations, respectively, were each ligated to the endogenic mouse FGFR3 promoter and first exon (see FIGS. 1b and 1a, respectively). In the mouse FGFR3 cDNA construct the first intron, second exon and half of the second intron derived from the mouse FGFR3 gene were also included (see FIG. 1a). A splicing acceptor sequence was introduced upstream to the FGFR3 mutated mouse cDNA sequence, and the bovine growth hormone polyadenylation signal was ligated to the 3'-end thereof (see FIGS. 1b and 1a).

Southern blots (FIG. 3a) or PCR detected the human or the mouse mutated FGFR3 transgene in 9 founder mice. All human and all mouse mutant FGFR3 transgenic mice founders contained a single integration site of their respective transgenes. Three clones were analyzed and showed identical features and therefore, unless otherwise indicated, one of the human mutated FGFR3 transgenic mice clones was chosen for further characterization of the present invention. All clones showed midface hypoplasia, normal or slight large skull with frontal bossing, normal-sized narrow trunk and proximal limb shortening (FIGS. 4a–e). It should be noted that the severity of phenotype varied among different individuals.

Mating between individuals belonging to each of the former transgenic mice mostly failed to produce homozygotes that could survive. It appeared that soon after birth they died from respiratory insufficiency. The homozygote newborns exhibited extremely short wide limbs, slight shorter narrow trunk, marked midface hypoplasia, large head and a very small rib cage as compared with heterozygotes and normal mice (FIGS. 5a–f and 6a–e). Except for skeletal abnormalities, autopsy showed no obvious gross or microscopic morphological abnormnaity as a cause of death although, it looks as if those individuals exhibit slight abdomen swelling.

Figure 3:
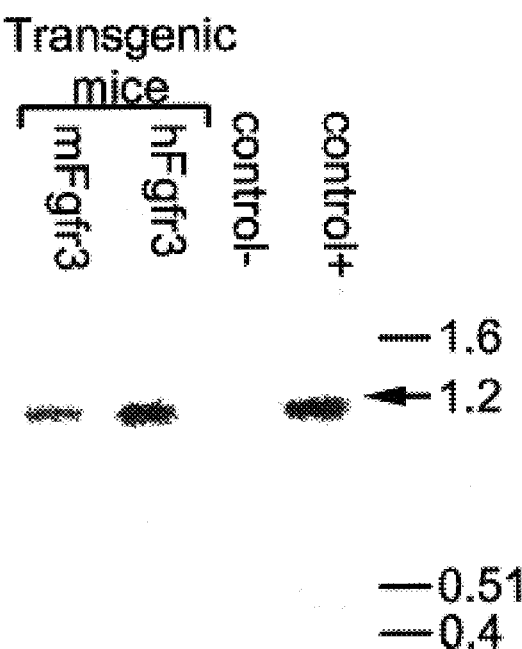
FIGS. 3a–b show southern and western blot analyses of normal and heterozygous human mutated FGFR3 transgenic mice (single locus transgene). (3a) Southern blot analysis of DNA isolated from tails of normal (control −) and transgenic mice. Those that show a 1.2 kb fragment are transgenic. Positions of marker fragments are indicated. Control +: Plasmid DNA which was used for transgenization. (3b) Western blot analysis of protein isolated from the above mentioned mice. Protein extracts were isolated from cartilage. 100 μg protein were loaded on each lane and FGFR3 was detected using an anti FGFR3 antibody to confirm the expression of the transgene. m=mouse. h=human.
Figure 3:
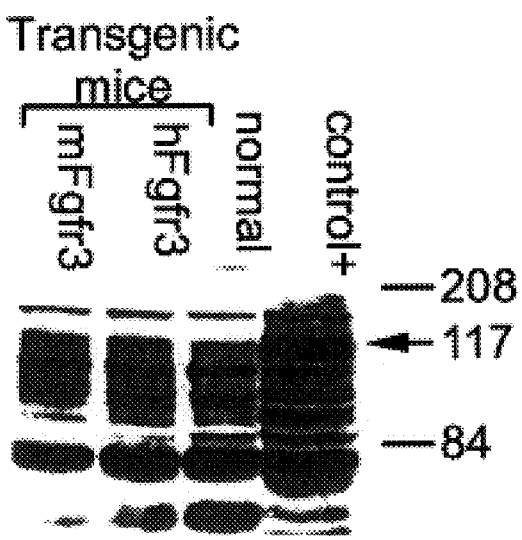
Figure 4A:
FIGS. 4a–e demonstrate subgross analysis of skeletons of 3-months-old transgenic mice. The mice were stained with alizarin red for bone, followed by alkaline digestion to allow visualization of the skeleton. Transgenic mice are shown on the right and normal littermates on the left. (4a) view of intact skeletons, showing a moderate rizomelic dwarfism of the heterozygous transgenic mouse, note that there is only a slight decrease in overall trunk length while, femur length was markedly reduced. The normal kyphosis present in the normal mouse is reduced in the transgenic one. (4b) details of head structures. (4c) transgenic mice have narrower rib cage. (4d) details of pelvis, hind, limbs and lumbosacral and tail vertebrae. Shortening of the femur and iliac bones and bowing of the tibiae is also evident. Metaphyseal flaring is also evident. (4e) scapula.
Figure 4B:
Figure 4C:
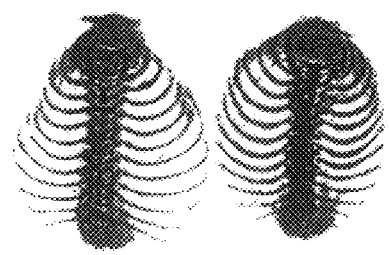
Figure 4D:
Figure 4E:
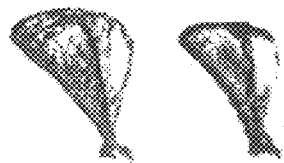
Figure 6A:
FIGS. 6a–e demonstrate skeletal parts of 19-days-old neonatal transgenic mice in quartets. The mice were stained with alizarin red for bone, followed by alkaline digestion to allow visualization of the skeleton. From the left the sequence is as follows: knockout mouse (null alleles), normal mouse, heterozygote human mutated FGFR3 transgenic mouse and homozygote human mutated FGFR3 transgenic mouse. (6a) Lateral view of head structures. The calvaria and mandibula are large but hypoplasia of the midface is evident in heterozygous and homozygous transgenic mice. (6b) Interior view of head structures. Note the angle and the radius of the foramen magnum. Skull base bones are smaller in the transgenic mice. (6c) Smaller rib cage in transgenic mice. Short, thick and capped tubular bones. (6d) Front limbs with ryzomelic shortening of long bones. Note the angle between the radius and the ulna. The scapula is much shorter in transgenic mice. (6e) Proximal hind limb shortening of transgenic individuals. The tibia is bowed and wider diaphses and flared metaphyses can be seen.
Figure 6B:
Figure 6C:
Figure 6D:
Figure 6E:

Western analysis of brain and cartilage cytoplasmic extracts prepared from mice heterozygous for mutated human FGFR3 show that the transgene is expressed in the above tissues in a manner corresponding to the gene copy number (FIG. 3b).

This was also confirmed by reversing the phenotype of FGFR3 null mice by the introduction of a single copy of the human mutated FGFR3 transgene. These mice were generated by mating homozygous or heterozygous FGFR3 knockout mice (received from Dr. C. Deng, Deng, 1996) with human mutated FGFR3 mice, heterozygote for the transgene.

It appears that the same severe skeletal abnormalities characterizing the above described homozygous transgenic newborns, can be identified in human mutated FGFR3 newborn mice that do not have active endogenic alleles (data not shown).

These findings demonstrate that simple over-expression of FGFR3 because of the mutation at codon 380 is not the cause for human achondroplasia, as the latter newborns although having only two FGFR3 alleles exhibit achondroplasia phenotypes. They further demonstrate that the quantity of mutated FGFR3 controls the severity of the disorder while the ratio of normal to mutated receptor is irrelevant.

Skeletal abnormalities: Gross examination of individuals heterozygous and homozygous for the human mutated FGFR3 transgene was further conducted by Radiography and Alizarin or Alizarin/Alcian blue staining of the bones. A comparison of normal mice and of their human mutated FGFR3 littermates showed (i) limb shortening particularly the proximal (rhizomelic) segments; (ii) unusual angle of limb bending; (iii) broader and denser limbs (wider diaphyses and metaphyses); (iv) bowing of limb bones in homozygotes only (especially the tibia and the fibula although, the fibula is less effected); (v) shorter middle finger (resembles the trident hand configuration); (vi) short, thick and capped tubular bones (smaller and narrower rib cage); (vii) larger skull with frontal bossing (large claveriae); (viii) smaller facial bones and skull base, including the foramen magnum (midface hypoplasia); (ix) tongue thrust, mandible is almost normally developed and seems even larger in homozygotes; (x) closing of the angle at the base of the cranium (90° instead of 120°); and (xi) substantially normal-size trunk, slightly smaller in homozygotes, yet characterized by spinal cord compression especially at the base of the skull and the lumbar region, pedicles which are short and thick and iliac wings which are short with narrower sacrosciatic notches and flat acetabular roofs (FIGS. 6a–e).

Figure 7:
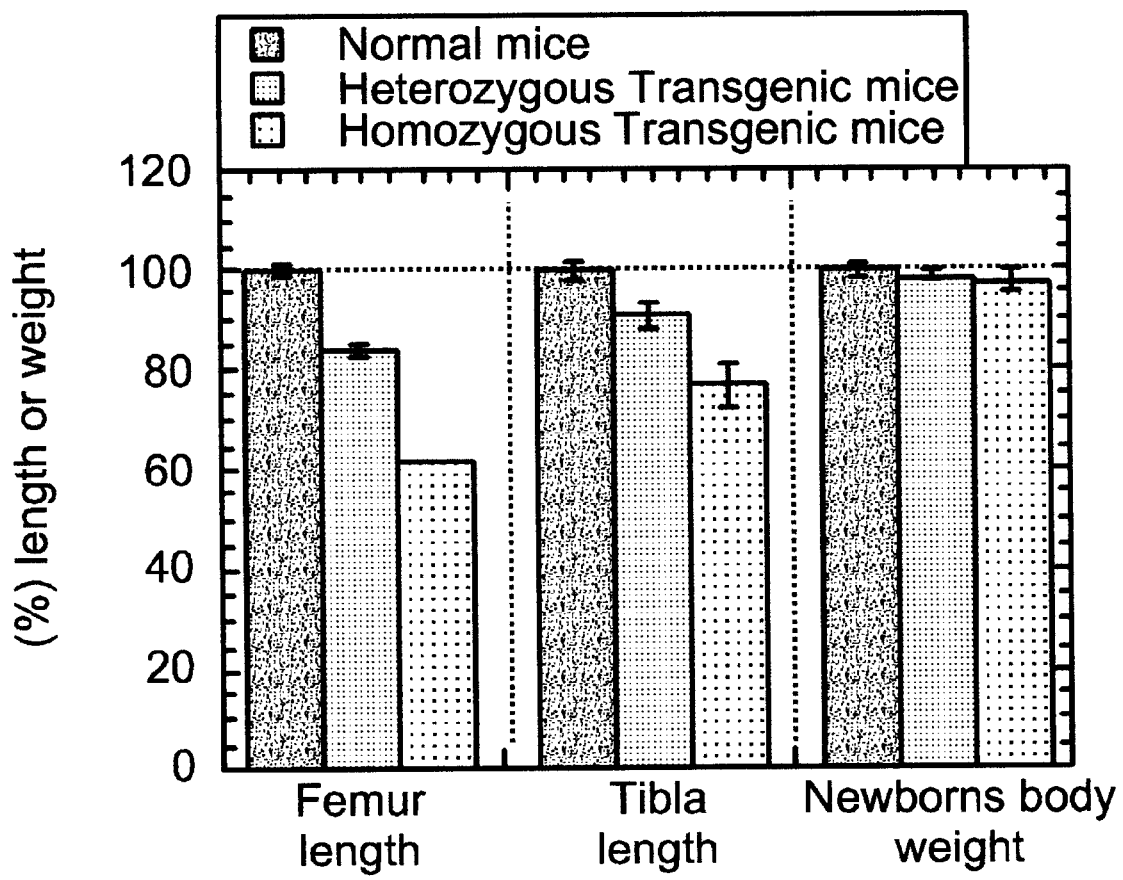
FIG. 7 demonstrates reduction in length of femur or tibia of newborn transgenic mice with no significant reduction in weight. The achondroplasia mutation leads to a significant decrease (16% for heterozygotes and 38% for homozygotes) in femur length compared to only 9% or 23% accordingly, in tibia length.

Precise measurements of long bone lengths between heterozygotes and non-transgenic littermates show a mean of 16% shortening of the femur, and a mean of 9% shortening of the tibia while, in homozygotes 38 % shortening of the femur, and 23% of the tibia is evident (FIG. 7). All long bones were significantly shorter (p<0.0001 for 3-months-old and p<0.00001 for 5-months-old heterozygote mice) than non-transgenic littermate controls (FIGS. 4a–e and 6a–e), whereas mean body weights of 18.65 grams for control mice and 19.2 grams for transgenic mice were not significantly different. As the mice grew older, the differences in bone length became more pronounced. Normalization of the bone lengths with body weight shows continued significant differences between transgenic and control mice for bone length per gram body weight. Furthermore, comparison of mutated FGFR3 transgenic newborns with non-transgenic littermates of exactly the same body weight continues to show a reduction in the size of long bones while no (in heterozygotes) or only slight (in homozygotes) trunk length reduction was seen. In addition, all homozygous transgenic newborn mice exhibit clear marked midface hypoplasia with direct correlation to long bone length reduction. Thus, the chondrodysplasia in mutated FGFR3 transgenic mice is not an artifact of gestation failure, but a clear disproportional dwarfism.

The following summarizes human mutated FGFR3 transgenic mice clearance features: large skull (within the norm) with frontal bossing; claveriae are large; facial bones and skull base are small including the foramen magnum; small jaw, especially the maxilla (tongue thrust); midface hypoplasia; scooped out nasal bridge; mandible is almost normally developed; proximal limb shortening (short extremities particularly in the proximal (rhizomelic) segments); bowing of the legs due to the overgrowth of the fibula relative to the tibia; micromelia with short thick and capped tubular bones; brachymetacarpalia; trident hands, short middle finger; wider diaphyses; flared metaphyses; spinal cord compression at the base of the skull, long normal-sized narrow trunk; narrowing of intervertebral distances from L1 to L5; squared iliac wings with narrow sacrosciatic notches; iliac bones are short and round with flat acetabular roofs; and lumbar lordosis. These conditions are recognizable at birth. Sexual development is normal. Final adult height ranges between 112 to 145 cm. Final adult height ranges between 112 to 145 cm.

Figure 8A:
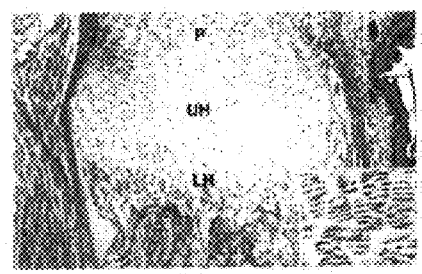
FIGS. 8a–i demonstrate histological analysis of transgenic and normal mice. (8a–c) Show proximal tibia growth plates of newborns, (8d–i) show proximal tibia growth plates of 3-months-old mice. The normal growth plate (FIGS. 8a, 8d, 8e and 8f) shows a typical zonal structure of differentiating chondrocytes. Proliferating chondrocytes (P) progressively enlarge to upper-hypertrophic chondrocytes (UP), and fuirther differentiate into terminally differentiated, lower-hypertrophic chondrocytes (LH). Age-matched growth-plates from heterozygous transgenic mice (FIGS. 8b, 8g, 8h and 8i) show less proliferative and hypertrophic cells, more intense staining with alcian-blue (8e and 8h) which suggests accumulation of proteoglycans in extracellular matrix, and vascular invasion within the upper-hypertrophic zone (8f and 8i).
Figure 8B:
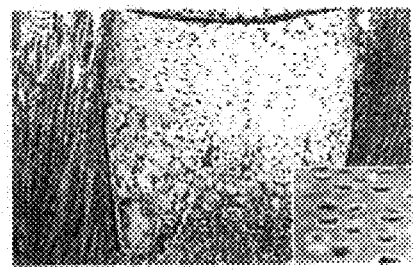
Figure 8C:
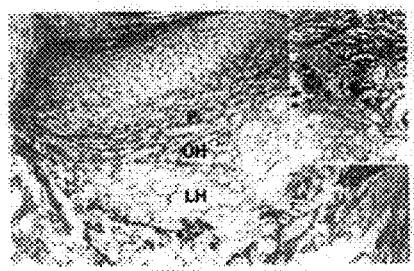
Figure 8D:
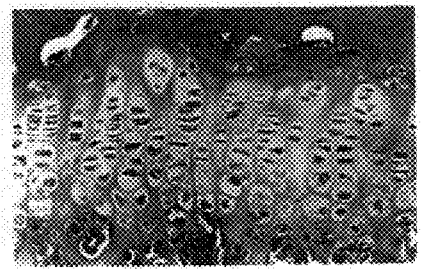
Figure 8E:
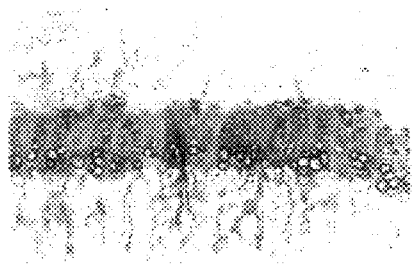
Figure 8F:
Figure 8G:
Figure 8H:
Figure 8I:

Histological analysis: Histological analysis of proximal tibia and distal femoral growth plates from 1-day, 1-month, 2-months and 3-months-old mice heterozygous for the human mutated FGFR3 transgene revealed shorter columns with less proliferative and hypertrophic cells (FIGS. 8a–i). Enhanced deposition and retention of extracellular matrix, particularly within the reserved zone is evident, some irregularly arranged chondrocytes were found along the columns, and foci of vascularization and transverse tunneling of the cartilage were identified. Homozygous newborn distal femur growth plates have much greater circumference, a definite shortage of chondrocytes which are irregularly arranged with a failure of columnization. Furthermore, in these mice, adequate bars of calcified hypertrophic cells fail to form, larger hypertrophic cells can be seen, and the ossification is sparse and irregular. Subchondral ossification may extend into the growth plate, separating the large hypertrophic cells from the proliferative ones (FIG. 8c). Vascularization foci and apoptotic centers are also dispersed within the hypertrophic zone.

Further analysis of 12-days-old (not shown), and 15-days-old embryos indicate that growth retardation is detected very early in limb development, from the stage of mesenchymal condensation. In day 15 the entire tibial growth plate is significantly diminished (FIGS. 9a–f). At this stage the reserved and proliferative zones are much smaller and hypertrophic chondrocytes are absent in homozygous transgenic embryos. This suggest that the delay in chondrocyte maturation is not a property of growth plate chondrocytes only, but rather a result of FGFR3 uncontrolled activation in all the cells that express this receptor, including chondrifying mesenchymal cells (pre-cartilage rudiments). The severe skeletal abnormal phenotype of homozygous transgenic embryos is apparent from day 14 of prenatal development onwards.

Figure 10A:
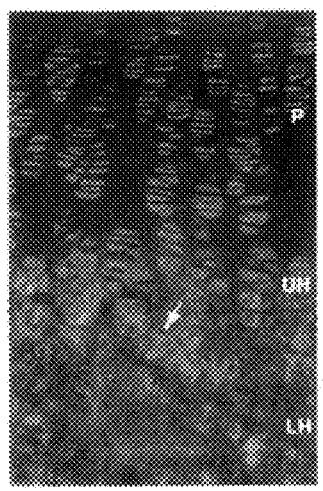
FIGS. 10a–f demonstrate the expression of FGFR3 (10a and 10b), proliferating cell nuclear antigen (PCNA, 10c and 10d), and collagen type X (10e and 10f). 8-days-old normal (10a and 10e) and heterozygous transgenic mice (10b and 10f) growth-plates were labeled by immunofluorescence for FGFR3 and X type collagen, which serves as a specific marker in the chondrocyte differentiation process. Intracellular expression of X type collagen is characteristic of upper-hypertrophic chondrocytes, whereas the densc, pericellular matrix labeling shown in red is found solely in the lower-hypertrophic zone. Note (10b) that higher levels of FGFR-3 expression are detected in the upper- and lower-hypertrophic cells in the transgenic mice growth plate, whereas, only upper-hypertrophic cells are stained in the normal control. This is consistent with the observation of Delezoide and her colleagues (Delezoide, 1997) who have recently demonstrated increased FGFR3 protein, suggesting post-translational stabilization of FGFR3, within the growth plate of thanatophoric dysplasia patients. A decrease in collagen type X and PCNA expression can be seen in the relevant areas of the transgenic mouse growth-plates.
Figure 10B:
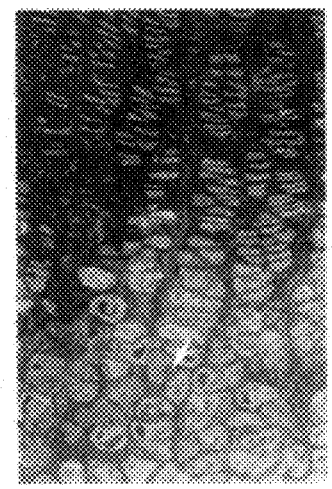

Immunocytochemical and in-situ hybridization analyses: Staining of normal and transgenic mice growth plate sections with an anti-FGFR3 antibody revealed a more intense signal in the reserved, lower-proliferative and upper-hypertrophic regions of mutated FGFR3 mice growth plates (FIGS. 10a–b). In addition, delayed down regulation of the receptor is observed, with most hypertrophic cells strongly stained for the receptor. Similarly, staining of the perichondrium was stronger and more homogeneous in the transgenic mice than in the age-matched control mice (data not shown). The immunoreactive material was observed only in the cytoplasm of hypertrophic cells. The above results suggest that the Gly 380 to Arg mutation did not alter FGFR3 RNA transcription but rather stabilized the activated FGFR3.

Figure 10C:
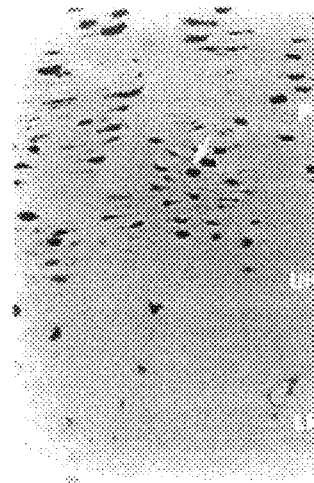
Figure 10D:
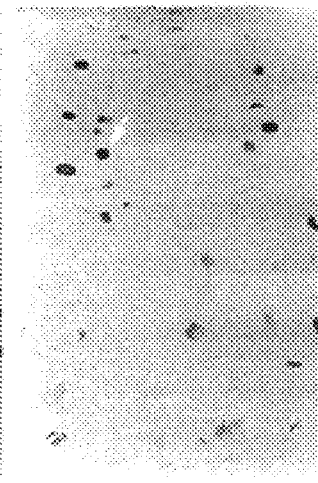

Since less cells can be detected per column, it is speculated that in addition to other processes, this might result from decrease in chondrocytes proliferation. To test this possibility, the proximal tibia growth plate of 8-days-old mice was stained with an antibody that detects the cell proliferation marker proliferating cell nuclear antigen (PCNA). Significant differences in the quantity of proliferating chondrocytes were detected upon comparing transgenic mice derived growth plate sections with those from normal mice (FIGS. 10c–d). As shown, growth plates isolated from 8-days-old transgenic mice exhibit less PCNA-expressing cells than those of corresponding wild-type control mice. Furthermore, in control growth plate sections there is strong staining by PCNA antibody in the maturation zone, whereas staining of transgenic mice sections reveals less intense signal and fewer PCNA-producing cells within that zone.

The FGF receptor family is made up of four distinct genes (FGFR1 through FGFR4). Together, the FGFR-FGF complex stimulates differentiation, chemotaxis, angiogenesis, mitogenesis, and cell survival, and regulates development, growth, and homeostasis. To test the possibility that prolonged expression of FGFR3 might influence the expression of FGFR-1 and/or FGFR-2 within the growth plate, tibial growth plates of 8-days-old mice were immunostained with specific antibodies that specifically detect the above receptors. The results show that FGFR1 is expressed in the hypertrophic chondrocytes of control and transgenic mice, while FGFR2 expression could not be detected at all. Thus, it appears that there is no loss in FGFR1 or FGFR2 expression in response to enhance and prolonged expression of FGFR3 during endochondral ossification.

Figure 10E:
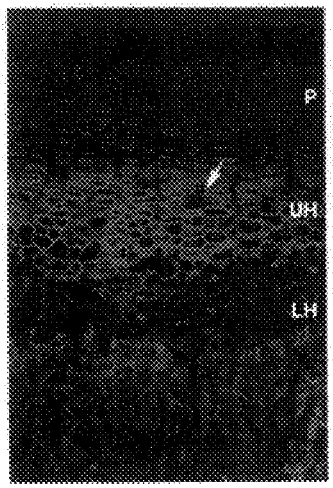
Figure 10F:
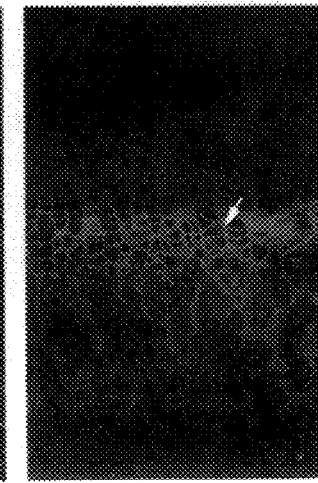

To assess the impact of the achondroplasia mutation on cartilage matrix markers molecular genetic markers corresponding to collagens were employed. These genes have been shown to play an important role in maintaining the mass, shape, and strength of bone tissue (Van der Rest, 1991, Erlebacher, 1995). The expression pattern of collagen type X in mutated FGFR3 transgenic mice highly corresponds the decreased column size mentioned earlier. Collagen type X is strongly expressed in hypertrophic chondrocytes and is used as a marker for these cells (FIGS. 10e–f). In mutant FGFR3 three-months-old mice, a thinner expression band can be observed and is proportional to the size of the hypertrophic zone. Extra-cellular collagen type II expression in the growth plates of mutant FGFR3 mice also showed lower levels than control mice.

Histology: Alcian blue staining can detect the presence of proteoglycans within the growth plate. A strong signal was observed only when mutant transgenic mice sections were stained (FIGS. 8e–h). This implies that Gly 380 to Arg mutated FGFR3 causes over-expression of sulfated proteoglycans.

Further observation under fluorescence microscopy of two months old mice growth plate sections revealed striking differences in matrix calcification/mineralization properties between control and transgenic mice. Lesions that appear very similar to the mineralized bone matrix were seen between the proliferative and the hypertrophic zones in some areas, suggesting that the achondroplasia transgenic mice exhibit "ossification tufts" which are mineralization extensions of the subchondral bone associated with achondroplasia and thanatophoric dysplasia patients (Langer, 1967, Morgan, 1980, Gorlin, 1997, Lewanda, 1996, Horton, 1993, and Sharrard, 1973).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES

Andersen, P. E. J., and Hauge, M. (1989). Congenital generalized bone dysplasia: a clinical, radiological, and epidemiological survey. J. Med. Genet., 26, 37–44.

Bargmann, C. I., Hung, M.-C. and Weinberg, R. A. (1986). Multiple independent activations of the neu oncogene by a point mutation altering the trans-membrane domain of p185. Cell, 45, (5) 649–657.

Basilico, C. and Moscatelli, D. (1992). The FGF family of growth factors and oncogenes. Adv. Cancer Res., 59, 115–165.

Bellus, G. A., McIntosh, I., Smith, E. A., Aylsworth, A. S., Kaitila, I., Horton, W. A., Greenhaw, G. A., Hecht, J. T., and Francomano, C. A. (1995). A recurrent mutation in the tyrosine kinase domain of fibroblast growth factor receptor 3 causes hypochondroplasia. Nature Genet., 10, 357–359.

Bellus, G. A., Hefferon, T. W., Ortiz, d. L., R. I., Hecht, J. T., Horton, W. A., Mashado, M., KAITILA, I., McIntosh, I. and Francomano, C. A. (1995). Achondroplasia is defined by recurrent G380R mutations of FGFR3. Am. J. Hum. Genet., 368–373.

BG, C. and al., e. (1997). Chimeric analysis of Fgfr1 function: a role for FGFR1 in morphogenetic novement through the primitive streak. Development, 124, (14) 2829–2841.

Bonaventure, J., Rousseau, F., Legeai-Mallet, L., Merrer, M. L., Munnich, A., and Maroteaux, P. (1996). Common mutations in the fibroblast growth factor receptor 3 gene account for achondroplasia, hypochondroplasia and thanatophoric dwarfism. Am. J. Med. Genet., 63, 148–154.

Chin, Y. E., Kitagawa, M., Kuida, K., Flavell, R. A. and Fu, X.-Y. (1997). Activation of the STAT signaling pathway can cause expression of caspase 1 and apoptosis. Mol. Cell. Biol., 17, (9) 5328–5337.

Coffin, J. D., R. Z. Florkiewicz, J. Neumann, T. Mort-Hopkins, G. W. Dom, P. Lightfoot, et al. (1995). Abnormal bone growth and selective translational regulation in FGF-2 transgenic mice. Mol. Biol. Cell., 6, 1861–1873.

Colvin, J. S. and al., e. (1996). Skeletal overgrowth and deafness in mice lacking FGFR3. Nat. Genet., 12, 390–397.

Delezoide, A.-L., Benoist, C. L., Legcai-Mallet, L., Brice, P., Senee, V., Yayon, A., Munnich, A., Vekemans, M. and Bonaventure, J. (1997). Abnormal FGFR3 expression in cartilage of thanatophoric dysplasia fetuses. Human Molecular Genetics, 6, (11) 1899–1906.

Deng, C., Wynshaw-Boris, A., Zhou, F., Kuo, A., and Leder, P. (1996). Fibroblast growth factor receptor 3 is a negative regulator of bone growth. Cell, 84, 911–921.

Dionne, C., Crumley, G., Bellot, F., Kaplow, J., Searfoss, G., Ruta, M., Burgess, W., Jaye, M. and Schlessinger, J. (1990). Cloning and expression of two distinct high-affinity receptors cross-reacting with acidic and basic FGFs. EMBO J., 9, 2685–2692.

Erlebacher, A., Filvaroff, E. H., Gitelman, S. E. and Derynck, R. (1995). Toward a molecular understanding of skeletal development. Cell, 80, 371–378.

Friesel, R. E. and Maciag, T. (1995). Molecular mechanisms of angiogenesis: fibroblast growth factor signal transduction. FASEB J., 9, 919–925.

Gorlin, R. J. (1997). Fibroblast growth factors, their receptors and receptor disorders. J. Cranio-Maxillofacial Surg., 25, 69–79.

Horton, W. A. and Hecht, J. T. (1993). The Chondrodysplasias. Connective tissue and its heritable disorders, (Chapter 24) 641–675.

Horton, W. A., Hood, O. J., Mashado, M. A. and Campbell, D. (1988). Growth plate cartilage studies in achondroplasia. "Human Achondroplasia, a multidisciplinary approach", 81–89.

Iannotti, J. P., Goldstein, S., Kuhn, J., Lipiollo, L. and Kaplan, F. S. (1994). Growth plate and bone development. In Simon, S. R. (ed.) Orthopaedic Basic Science. American Academy of Orthopaedic Surgeons, Rosemont, Ill., 185–217.

Jannotti, J. P., Goldstein, S., Kuhn, J., Lipiello, L. and Kaplan, F. S. (1994). Growth plate and bone development. In Simon, S. R. (ed.), Orthopaedic Basic Science. American academy of Orthopaedic Surgeons, Rosemont, Ill., 185–217.

Ikegawa, S. and al., e. (1995). Mutations of the FGFR3 gene in one familial and six sporadic cases of achondroplasia in Japanese patients. Hum. Genet., 96, (3) 309–311.

Inouye, M. (1976). Differential staining of cartilage and bone in fetal mouse skeleton by alcian blue and alizarin red S. Cong. Anom., 16, 171–173.

Jaye, M., Schiessinger, J. and Dionne, C. A. (1992). Fibroblast growth factor receptor tyrosine kinases: molecular analysis and signal transduction. Biochim. Biophys. Acta, 1135, 185–199.

Johnson, D. E. and Williams, L. T. (1993). Structural and functional diversity in the FGF receptor multigene family. Adv. Cancer Res., 60, 1–41.

Kato, Y., Iwamoto, M. and (1990). Fibroblast growth factor is an inhibitor of chondrocyte terminal differentiation. J. Biol. Chem., 265, 5903–5909.

Keegan, K., Johnson, D., Williams, L. and Hayman, M. (1991). Isolation of an additional member of the fibroblast growth factor receptor family, FGFR 3. Proc. Natl. Acad. Sci. USA, 88, 1095–1099.

Langer, L. O., Jr., Spranger, J. W., Greinacher, I. and al., e. (1969). Thanatophoric dysplasia. Radiology, 92, 285–294.

Langer, L. O. J., Baumann, P. A. and Gorlin, R. J. (1967). Achondroplasia. Am. J. Roentgenol., 100, 12–26.

Lewanda, A. F., Meyers, G. A. and Jabs, E. W. (1996). Craniosynstosis and skeletal dysplasias: Fibroblast growth factor receptor defects. Proc. Assoc. Am. Phys., 108, 19–24.

MacDonald, I. M., A. G. Hunter, P. M. Macleod, and S. B. MacMurray. (1989). Growth and development in thanatophoric dysplasia. Am. J. Med. Genet, 33, 508–512.

Mason, I. J. (1994). The ins and outs of FGFs. Cell, 78, (4) 547–552.

Maynard, J. A., Ippolito, E. G., Ponseti, I. V. and Mickelson, M. R. (1981). Histochemistry and ultrastructure of the growth plate in achondroplasia. J. Bone Joint Surg., 63, 969–979.

McKusick, V. A., Kelly, T. E., and Dorst, J. P. (1973). Observations suggesting allelism of the achondroplasia and hypochondroplasia genes. J. Med. Genet., 10, 11–16.

McLeod, M. J. (1980). staining of cartilage and bone in whole mouse fetuses by alcian blue and alizarin red S. Teratology, 22, (3) 299–301.

Mohammadi, M., I. Dikie, A. Sorokin, W. H. Burgess, M. Jaye, and J. Schlessinger (1996). Identification of six novel autophosphorylation sites on the fibroblast growth factor receptor I and elucidation of their importance in receptor activation and signal transduction. Mol. Cell. Biol., 16, 977–989.

Morgan, D. F. and Young, R. F. (1980). Spinal neurological complications of achondroplasia. J. Neurosurg., 52, 463–472.

Muenke, M. and Schell, U. (1995). Fibroblast-growth-factor receptor mutations in human skeletal disorders. Trends Genet., 11, 308–313.

Naski, M. C., Wang, Q., Xu, J., and Ornitz, D. M. (1996). Graded activation of FGFR3 by mutations causing achondroplasia and thanatophoric dysplasia. Nature Genet., 13, 233–237.

Park, W.-J., Bellus, G. A. and Jabs, E. W. (1995). Mutations in fibroblast growth factor receptors: Phenotypic consequences during eukaryotic development. Am. J. Hum. Genet., 57, 748–754.

Park, W. J., Bellus, G. A. and Jabs, E. W. (1995). Mutations in fibroblast growth factor receptors: phenotypic consequences during eukaryotic development. Am. J. Hum. Genet., 57, 748–754.

Partanen, J., Makela, T., Earola, E., Korhonen, J., Hirronen, D., Clnesson-Welsh, L., and Alitalo, K. (1991). A novel FGFR4 with distinct expression patern. EMBO J., 10, 1347–1354.

Perez-Castro, A. V., J., W. and R., A. M. (1995). Genomic organization of the mouse Fgfr3 gene. Genomics, 30, 157–162.

Perez-Castro, A.V., J., W. and R., A. M. (1997). Genomic organization of the human FGFR3 gene and comparative sequence analysis with the mouse Fgfr3 gene. Genomics, 41, (1) 10–16.

Peters, K., D. Ornitz, S. Werner, and L. Williams. (1993). Unique expression pattern of the FGF receptor 3 gene during mouse organogenesis. Dev. Biol., 155, 423–430.

Peters, K. G., Werner, S., Chen, G. and Williams, L. T. (1992). Two FGF receptor genes are differentially expressed in epithelial and mesenchymal tissues during limb formation and organogenesis in the mouse. Development, 114, 233–243.

Ponseti, I. V. (1970). Skeletal growth in achondroplasia. J. Bone Joint Surg., 52A, 701–716.

Prinos, P., Kilpatrick, N. W. and Tsipouros, P. (1995). A common FGFR3 gene mutation in hypochondroplasia. Hum. Mol. Genet., 4, (11) 2097–2101.

Rimoin, D. L. (1974). Histopathology and ultrastructure of cartilage in the chondrodystrophies. Birth defects Original Article Series, 10, 1–18.

Rimoin, D. L., Hughes, G. N., Kaufman, R. L., Rosenthal, R. E., McAlister, W. H. and Silberberg, R. (1970). Endochondral ossification in achondroplastic dwarfism. N. Eng. J. Med., 183, (14) 728–735.

Rousseau, F., Saugier, P., Le Merrer, M. Munnich, A., Delezoide, A. L., Maroteaux, P., Bonaventure, J., Narcy, F., and Sanak, M. (1995). Stop codon FGFR3 mutations in thanatophoric dwarfism type 1. Nature Genet., 10, 11–12.

Rousseau, F., Ghozzi, V., Delezoide, A. L., Legeai-Mallet, L. (1994). Mutations in the gene encoding Fgfr3 in achondroplasia. Nature, 371, (6494) 252–254.

Rousseau, F. et al. (1996). Missense FGFR3 mutations create cysteine residues in TD1. Hum. Mol. Genet., 5, (4) 509–512.

Shah, K. R. A., and A. H. Cameron. (1973). Thanatophoric dwarfism. J. Med. Genet., 10, 243–252.

Sharrard, W. J. W. (1973). Cartilaginous dysplasias with abnormal maturation of growth plate chondroblasts. Paediatric orthopaedics and fractures, Blackwell scientific publications, 59–63.

Shiang, R., Thompson, L. M., Zhu, Y. Z., Church, D. M., Fielder, T. J., Bocian, M., Winokur, S. T., and Wasmuth, J. J. (1994). Mutations in the transmembrane domain of FGFR3 cause the most common genetic form of dwarfism, achondroplasia. Cell, 78, 335–342.

Sillence, D. O., Horton, W. A. and Rimoin, D. L. (1979). Morphologic studies in the skeletal dysplasias. Am. J. Pathol., 96, 813–870.

Sommer, A., Young-Wee, T. and Frye, T. (1987). Achondroplasia-hypochondroplasia complex. Am. J. Med. Genet., 26, 949–957.

Spranger, J. (1992). International classification of osteochondrodysplasias. Eur. J. Ped., 151, 407–415.

Stanescu, R., Stanescu, V., and Moroteaux, P. (1990). Homozygous achondroplasia: morphologic and biochemical study of cartilage. Am. J. Med. Genet., 2 7, 412–4201.

Stemberg, M. J. E. and Gullick, W. J . (1989). Neu receptor dimerization. Nature, 339, (6226) 587.

Stoilov, I., Kilpatrick, M. W., and Tsipouras, P. (1995). Possible genetic heterogeneity in hypochondroplasia. J. Med. Genet., 45, 492–493.

Su, W.-C. S., M, K., Xue, N., Xie, B., Garofalo, S., Cho, J., Deng, C., Horton, W. A. and Fu, X. Y. (1997). Activation of Stat1 by mutant fibroblast growth-factor receptor in T. D. type 33 dwarfism. Nature, 386, 288–292.

Superti-Furga, A., Eich, G., Bucher, H. U., Wisser, J., Giedion, A., Gitzelmann, R., and Steinmann, B. (1995). A glycine 375-to-cysteine substitution in the transmembrane domain of the fibroblast growth factor receptor-3 in newborns with achondroplasia. Eur. J. Ped., 154, 215–219.

Tavormina, P. L., D. L. Rimoin, D. H. Cohn, Y. Z. Zhu, R. Shiang, and J. J. Wasmuth (1995). Another mutation that results in the substitution of an unpaired cysteine residue in the extracellular domain of FGFR3 in thanatophorc dysplasia type I. Hu man Mol. Genet., 4, 2175–2177.

Tavormina, P. L., Shiang, R., Thompson, L. M., Zhu, Y. Z., Wilkin, D. J., Lachman, R. S., Wilcox, W. R., Rimoin, D. L., Cohn, D. H., and Wasmuth, J. J. (1995). Thanatophofic dysplasia (types I and II) caused by distinct mutations in fibroblast growth factor receptor 3. Nature Genet., 9, 321–328.

Thompson, L. M., Raffioni, S., Wasmuth, J. J. and Bradshaw, R. (1997). Chimeras of the n ative form of achondroplasia mutant (G375C) of human FGFR3 induce ligand dependent differentiation of PC12 cells. Mol. Cell. Biol., 1G7, (7) 4169–4177.

Van der Rest, M. and Garrone, R. (1991). Collagen family of proteins . FASEB J., 5, 2814–2823.

Webster, M. K., D'avis P. Y., Robertson S. C., and Donoghue D. J. (1996). Profound ligand-independent kinase activation of fibroblast FGFR3 by the activation loop mutation responsible for a lethal skeletal dysplasia, thanatophoric dysplasia type II. Mol. Cell. Biol., 16, (8) 4081–4087.

Webster, M. K. and Donoghue, D. J. (1996). constitutive activation of FGFR3 by the transmembrane domain point mutation found in achondroplasia. Embo J., 15, (3) 520–527.

Webster, M. K. and Donoghue, D. J. (1997). FGFR activation in skeletal disorders: too much of a good thing. Trends Genet., 13, 178–182.

Wuchner, C., Hilbert, K., Zabel, B., and Winterpacht, A. (1997) Human FGFR3 gene: genomic sequence and primer set information for gene analysis. Hum. Genet., 100, 215–219.

Wynne-Davies, R. (1986). pseudoachondroplasia: clinical diagnosis at different ages and comparison of autosomal dominant and recessive types. A review of 32 patients. J. Med. Genet., 23, (5) 425–434.

Xu, X. et al. (1998). FGFR2-mediated reciprocal regulation loop between FGF8 and FGFIO is essential for limb induction. Development, 125, (4) 753–765.

Young, R. S., Pochachevsky, R., Leonidas, J. C. and al., e. (1973). Thanatophoric dwarfism and cloverleaf skull. Radiology, 106, 401–406.

What is claimed is:

1. A transgenic mouse whose genome comprises a nucleic acid construct, wherein the construct comprises a DNA segment consisting of nt 264–2719 of the sequence disclosed in SEQ ID NO 2 and said DNA segment comprises the promoter region and 1st exon of the mouse fibroblast growth factor receptor 3 (FGFR3) gene operatively linked to a DNA fragment encoding a mutant of the c form of human FGFR3 wherein the Glycine residue at position 380 is substituted with Arginine, and wherein said transgenic mouse exhibits the characteristics of human achondroplasia that include, shortening of the limbs, midface hypoplasia, and large skull.

2. The transgenic mouse of claim 1, wherein the transgene is in a hetero- or homo-zygous form.

3. The transgenic mouse of claim 1, wherein the transgenic mouse is a model for human achondroplasia.

4. The transgenic mouse of claim 1, wherein both alleles of the endogenous FGFR3 gene of the transgenic mouse have been inactivated such that said endogenous FGFR3 gene does not produce FGFR3 protein.

5. The transgenic mouse of claim 1, wherein the mouse produces endogenous active FGFR3 protein.

6. A transgenic mouse whose genome comprises a nucleic acid construct, wherein the construct comprises a DNA segment consisting of nt 264–5255 of the sequence disclosed in SEQ ID NO 2 and said DNA segment comprises the promoter region, first exon, first intron, second exon, and 1.66 kb 5' sequences of the mouse FGFR3 gene operatively linked to a DNA fragment encoding a mutant of the murine FGFR3 wherein the Glycine residue at position 374 is substituted with Arginine, and wherein said transgenic mouse exhibits the characteristics of human achondroplasia that include, shortening of the limbs, midface hypoplasia, and large skull.

7. The transgenic mouse of claim 6, wherein the transgene is in a hetero- or homozygous form.

8. The transgenic mouse of claim 6, wherein the transgenic mouse is a model for human achondroplasia.

9. The transgenic mouse of claim 6, wherein the mouse produces endogenous active FGFR3 protein.

* * * * *